United States Patent
Yu et al.

(10) Patent No.: US 10,935,544 B2
(45) Date of Patent: Mar. 2, 2021

(54) GLYCAN ARRAYS AND METHOD OF USE

(71) Applicant: OBI Pharma, Inc., Taipei (TW)

(72) Inventors: Peiwen Yu, Taipei (TW); Wei-Chien Tang, Taipei (TW); Shu-Yi Lin, Taipei (TW); Cheng-Chi Wang, Taipei (TW)

(73) Assignee: OBI PHARMA, INC., Taipei (TW)

( * ) Notice: Subject to any disclaimer, the term of this patent is extended or adjusted under 35 U.S.C. 154(b) by 1106 days.

(21) Appl. No.: 15/255,996

(22) Filed: Sep. 2, 2016

(65) Prior Publication Data

US 2017/0067885 A1 Mar. 9, 2017

Related U.S. Application Data

(60) Provisional application No. 62/214,779, filed on Sep. 4, 2015.

(51) Int. Cl.
G01N 33/574 (2006.01)
G01N 33/53 (2006.01)

(52) U.S. Cl.
CPC ... *G01N 33/5308* (2013.01); *G01N 33/57484* (2013.01); *G01N 33/57488* (2013.01); *G01N 2400/02* (2013.01); *G01N 2400/38* (2013.01); *G01N 2500/04* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| RE30,985 E | 6/1982 | Cartaya |
| 4,419,446 A | 12/1983 | Howley et al. |
| 4,522,811 A | 6/1985 | Eppstein et al. |
| 4,560,655 A | 12/1985 | Baker |
| 4,601,903 A | 7/1986 | Frasch |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,849,222 A | 7/1989 | Broaddus |
| 4,927,762 A | 5/1990 | Darfler |
| 4,943,533 A | 7/1990 | Mendelsohn et al. |
| 4,965,199 A | 10/1990 | Capon et al. |
| 4,975,278 A | 12/1990 | Senter et al. |
| 5,004,697 A | 4/1991 | Pardridge |
| 5,057,540 A | 10/1991 | Kensil et al. |
| 5,061,620 A | 10/1991 | Tsukamoto et al. |
| 5,100,669 A | 3/1992 | Hyon et al. |
| 5,112,596 A | 5/1992 | Malfroy-Camine |
| 5,122,469 A | 6/1992 | Mather et al. |
| 5,212,290 A | 5/1993 | Vogelstein et al. |
| 5,264,365 A | 11/1993 | Georgiou et al. |
| 5,268,164 A | 12/1993 | Kozarich et al. |
| 5,500,362 A | 3/1996 | Robinson et al. |
| 5,506,206 A | 4/1996 | Kozarich et al. |
| 5,508,192 A | 4/1996 | Georgiou et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg et al. |
| 5,571,894 A | 11/1996 | Wels et al. |
| 5,580,717 A | 12/1996 | Dower et al. |
| 5,587,458 A | 12/1996 | King et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,648,237 A | 7/1997 | Carter |
| 5,661,016 A | 8/1997 | Lonberg et al. |
| 5,686,416 A | 11/1997 | Kozarich et al. |
| 5,733,743 A | 3/1998 | Johnson et al. |
| 5,804,396 A | 9/1998 | Plowman |
| 5,814,344 A | 9/1998 | Tice et al. |
| 5,821,337 A | 10/1998 | Carter et al. |
| 5,840,523 A | 11/1998 | Simmons et al. |
| 5,869,046 A | 2/1999 | Presta et al. |
| 5,891,996 A | 4/1999 | Mateo de Acosta Del Rio et al. |
| 6,004,940 A | 12/1999 | Marasco et al. |
| 6,027,888 A | 2/2000 | Georgiou et al. |

(Continued)

FOREIGN PATENT DOCUMENTS

| | | |
|---|---|---|
| CN | 1871025 A | 11/2006 |
| CN | 103108654 A | 5/2013 |

(Continued)

OTHER PUBLICATIONS

Carbohydrate Microarrays (Yann Chevolot, editor Humana Press) (Year: 2012).*
Büll, Christian, et al. "Sialic acid blockade suppresses tumor growth by enhancing T-cell—mediated tumor immunity." Cancer Research 78.13 (2018): 3574-3588.
Chuang, Po-Kai, et al. "Signaling pathway of globo-series glycosphingolipids and β1, 3-galactosyltransferase V (β3GalT5) in breast cancer." Proceedings of the National Academy of Sciences 116.9 (2019): 3518-3523.
International Search Report/Written Opinion dated Oct. 18, 2019 in counterpart application PCT/US2019/035168, 13 pages.
International Search Report dated Dec. 3, 2019 in counterpart application PCT/US2019/039414, 5 pages.

(Continued)

*Primary Examiner* — Christopher M Gross
(74) *Attorney, Agent, or Firm* — Prosyla Group, PC

(57) ABSTRACT

The invention relates to linkers and methods for generating arrays with linkers. The invention also relates to methods for identifying agents that bind to various types of molecules on the arrays and to defining the structural elements of the molecules on the arrays that bind to those agents. The arrays and methods provided herein may be used for epitope identification, drug discovery and as analytical tools. The invention provides useful glycans and epitope determinants that are useful in detecting, diagnosing, recurrence monitoring and preventing cancer.

29 Claims, 21 Drawing Sheets

(56) References Cited

U.S. PATENT DOCUMENTS

| | | |
|---|---|---|
| 6,083,715 A | 7/2000 | Georgiou et al. |
| 6,265,150 B1 | 7/2001 | Terstappen et al. |
| 6,329,173 B1 | 12/2001 | Marasco et al. |
| 6,524,584 B2 | 2/2003 | Kensil |
| 6,544,952 B1 | 4/2003 | Danishefsky et al. |
| 6,703,019 B1 | 3/2004 | Malfroy-Camine |
| 7,595,292 B2 | 9/2009 | Brocchini et al. |
| 8,268,969 B2 | 9/2012 | Wong et al. |
| 9,850,473 B2 | 12/2017 | Wang |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0129186 A1 | 7/2003 | Beliveau et al. |
| 2003/0153492 A1 | 8/2003 | Danishefsky et al. |
| 2003/0162695 A1 | 8/2003 | Schatzberg et al. |
| 2004/0018194 A1 | 1/2004 | Francisco et al. |
| 2004/0131692 A1 | 7/2004 | Kreuter et al. |
| 2004/0204354 A1 | 10/2004 | Nelson et al. |
| 2004/0208884 A1 | 10/2004 | Danishefsky et al. |
| 2004/0229310 A1 | 11/2004 | Simmons |
| 2004/0247608 A1 | 12/2004 | Krantz et al. |
| 2005/0048572 A1 | 3/2005 | Reilly et al. |
| 2005/0089473 A1 | 4/2005 | Black et al. |
| 2005/0124533 A1 | 6/2005 | Schatzberg et al. |
| 2006/0035267 A1 | 2/2006 | Livingston et al. |
| 2007/0059769 A1 | 3/2007 | Blixt et al. |
| 2009/0317411 A1 | 12/2009 | Wong et al. |
| 2010/0136042 A1 | 6/2010 | Wong et al. |
| 2010/0166790 A1 | 7/2010 | Agadjanyan et al. |
| 2010/0286035 A1 | 11/2010 | Ohtaki et al. |
| 2011/0117009 A1 | 5/2011 | Kratz et al. |
| 2012/0237532 A1 | 9/2012 | Olbrich et al. |
| 2012/0294859 A1 | 11/2012 | Goletz et al. |
| 2012/0321583 A1 | 12/2012 | Yurkovetskiy et al. |
| 2012/0328646 A1 | 12/2012 | Wong et al. |
| 2013/0095173 A1 | 4/2013 | Danishefsky et al. |
| 2013/0232589 A1 | 9/2013 | Papkoff et al. |
| 2014/0363455 A1 | 12/2014 | Stull et al. |
| 2015/0030669 A1 | 1/2015 | Platscher et al. |
| 2015/0087814 A1 | 3/2015 | Wang et al. |
| 2015/0297696 A1 | 10/2015 | Yu et al. |
| 2015/0316556 A1 | 11/2015 | Hardt et al. |
| 2015/0344551 A1 | 12/2015 | Wong et al. |
| 2016/0074522 A1 | 3/2016 | Okuda et al. |
| 2016/0102151 A1 | 4/2016 | Wong et al. |
| 2016/0339089 A1 | 11/2016 | Yu et al. |
| 2017/0067885 A1 | 3/2017 | Yu et al. |
| 2017/0101462 A1 | 4/2017 | Yu et al. |
| 2017/0283488 A1 | 10/2017 | Yu et al. |
| 2017/0283489 A1 | 10/2017 | Bosio et al. |
| 2017/0304419 A1 | 10/2017 | Yu et al. |
| 2017/0335281 A1 | 11/2017 | Loew et al. |
| 2018/0028629 A1 | 2/2018 | Yu et al. |
| 2018/0193481 A1 | 7/2018 | Chang et al. |
| 2018/0208915 A1 | 7/2018 | Kawaguchi et al. |
| 2018/0339061 A1 | 11/2018 | Yu et al. |

FOREIGN PATENT DOCUMENTS

| | | |
|---|---|---|
| EP | 0404097 A2 | 12/1990 |
| EP | 1391213 A1 | 2/2004 |
| EP | 2993182 A1 | 3/2016 |
| JP | 2006-507233 A | 3/2006 |
| KR | 10-2012-0014238 A | 2/2012 |
| WO | WO 87/00195 A1 | 1/1987 |
| WO | WO 90/03184 A1 | 4/1990 |
| WO | WO 90/03430 A1 | 4/1990 |
| WO | WO 91/00360 A1 | 1/1991 |
| WO | WO 91-10741 | 7/1991 |
| WO | WO 92/00373 A1 | 1/1992 |
| WO | WO 92/09690 A2 | 6/1992 |
| WO | WO 93/01161 A1 | 1/1993 |
| WO | WO 93/06213 A1 | 4/1993 |
| WO | WO 93/007861 A1 | 4/1993 |
| WO | WO 93/08829 A1 | 5/1993 |
| WO | WO 93/16185 A2 | 8/1993 |
| WO | WO 94/04690 A1 | 3/1994 |
| WO | WO 94/011026 A2 | 5/1994 |
| WO | WO 95/011010 A1 | 4/1995 |
| WO | WO 96/07754 A1 | 3/1996 |
| WO | WO 96/11711 A1 | 4/1996 |
| WO | WO 96/30347 A1 | 10/1996 |
| WO | WO 96-33735 | 10/1996 |
| WO | WO 96/33978 A1 | 10/1996 |
| WO | WO 96/33980 A1 | 10/1996 |
| WO | WO 96-34096 | 10/1996 |
| WO | WO 96/40210 A1 | 12/1996 |
| WO | WO 97/38983 A1 | 10/1997 |
| WO | WO 98-24893 | 6/1998 |
| WO | WO 98/36772 A1 | 8/1998 |
| WO | WO 98/43960 A1 | 10/1998 |
| WO | WO 99/06378 A1 | 2/1999 |
| WO | WO 99/06396 A1 | 2/1999 |
| WO | WO 99/09016 A1 | 2/1999 |
| WO | WO 99/042130 A1 | 8/1999 |
| WO | WO 2000/41720 A1 | 7/2000 |
| WO | WO 2000/48630 A1 | 8/2000 |
| WO | WO-2000/49412 A1 | 8/2000 |
| WO | WO 2003/015796 A1 | 2/2003 |
| WO | WO 2003/043583 A2 | 5/2003 |
| WO | WO 2003/077945 A1 | 9/2003 |
| WO | WO 2004/011476 A1 | 2/2004 |
| WO | WO 2004/032828 A2 | 4/2004 |
| WO | WO 2005/007197 A2 | 1/2005 |
| WO | WO 2006/105152 A2 | 10/2006 |
| WO | WO 2006/134423 A2 | 12/2006 |
| WO | WO 2007/026190 A2 | 3/2007 |
| WO | WO 2007/044515 A1 | 4/2007 |
| WO | WO 2009-035494 | 3/2009 |
| WO | WO 2009/126737 A2 | 10/2009 |
| WO | WO-2011/156774 A2 | 12/2011 |
| WO | WO 2014-107652 | 7/2014 |
| WO | WO-2014/178195 A1 | 11/2014 |
| WO | WO 2015/143123 A2 | 9/2015 |
| WO | WO 2015-157629 | 10/2015 |
| WO | WO 2015-159118 | 10/2015 |
| WO | WO 2016/026742 A1 | 2/2016 |
| WO | WO 2016/044326 A1 | 3/2016 |
| WO | WO 2016/118961 A1 | 7/2016 |
| WO | WO 2016/123593 A1 | 8/2016 |
| WO | WO 2017/041027 A1 | 3/2017 |
| WO | WO 2017/062792 A1 | 4/2017 |
| WO | WO 2017/172990 A1 | 10/2017 |
| WO | WO 2018/002640 A2 | 1/2018 |
| WO | WO 2018/022933 A1 | 2/2018 |
| WO | WO 2018/023121 A1 | 2/2018 |
| WO | WO 2018/094414 A1 | 5/2018 |

OTHER PUBLICATIONS

Ragupathi, Govindaswami, et al. "A novel and efficient method for synthetic carbohydrate conjugate vaccine preparation: synthesis of sialyl Tn-KLH conjugate using a 4-(4-N-maleimidomethyl) cyclohexane-1-carboxyl hydrazide (MMCCH) linker arm." Glycoconjugate Journal 15.3 (1998): 217-221.

Abrahmsén et al, "Analysis of signals for secretion in the staphylococcal protein A gene," EMBO J., Dec. 30, 1985, 4(13B):3901-3906.

Allen, P. Z. et al Immunochemical Studies on a Sophorosyl-Azoprotein Conjugate, Biochemistry, 1967, 6(10), 3029-3036.

Arié et al., "Chaperone function of FkpA, a heat shock prolyl isomerase, in the periplasm of *Escherichia coli*," Mol. Microbiol., Jan. 2001, 39(1):199-210.

Avery, Oswald et al., Chemo-Immunological Studies on Conjugated Carbohydrate-Proteins, J. Exp. Med., 1929, 50, 533-550.

Bachmann, Cellular and Molecular Biology, vol. 2, Chapter 72: Derivations and Genotypes of Some Mutant Derivatives of *Escherichia coli* K-12, Neidhardt et al., eds., 1987, pp. 1190-1219, American Society for Microbiology, Washington, D.C.

(56) References Cited

OTHER PUBLICATIONS

Baldwin et al., "Monoclonal antibodies in cancer treatment," Lancet, Mar. 15, 1986, 327(8481):603-605.
Barbas et al., "Assembly of combinatorial antibody libraries on phage surfaces: the gene III site," Proc. Natl. Acad. Sci. U.S.A., Sep. 15, 1991, 88(18):7978-7982.
Barbas, C.F. et al., "Semisynthetic combinatorial antibody libraries: a chemical solution to the diversity problem" Proc. Natl. Acad. Sci. USA, May 15, 1992, 89(10): 4457-4461.
Barbas et al., "In vitro evolution of a neutralizing human antibody to human immunodeficiency virus type 1 to enhance affinity and broaden strain cross-reactivity," Proc. Nat. Acad. Sci. U.S.A., Apr. 26, 1994, 91(9):3809-3813.
Barnes et al., "Methods for growth of cultured cells in serum-free medium," Anal. Biochem., Mar. 1, 1980, 102(2):255-270.
Bass et al., "Hormone phage: an enrichment method for variant proteins with altered binding properties," Proteins, 1990, 8(4):309-314.
Berenbaum, M. C., What is Synergy?, Pharmacol. Rev. 41(2) :93-141, 1989.
Bergman, Jan, and Lennart Venemalm. "Efficient synthesis of 2-chloro-, 2-bromo-, and 2-iodoindole." The Journal of Organic Chemistry 57.8 (1992): 2495-2497.
Bhaskar, Vinay, et al. "E-selectin up-regulation allows for targeted drug delivery in prostate cancer." Cancer Research 63.19 (2003): 6387-6394.
Bird, R.E., et al., "Single-chain antigen-binding proteins" Science Oct. 21, 1988; 242(4877):423-426.
Bliss, C.I., The Calculation of Microbial Assays, Bacterial. Rev. 20:243-258, 1956.
Bobo et al., "Convection-enhanced delivery of macromolecules in the brain," Proc. Natl. Acad. Sci. U.S.A., Mar. 15, 1994, 91(6) 2076-2080.
Boerner et al., "Production of antigen-specific human monoclonal antibodies from in vitro-primed human splenocytes," J. Immunol., Jul. 1, 1991, 147(1):86-95.
Borisy, Alexis et al., Systematic Discovery of Multicomponent Therapeutics, Proc. Natl. Acad. Sci. 100(13):7977-7982, 2003.
Bothmann et al., "The periplasmic *Escherichia coli* peptidylprolyl cis,trans-isomerase FkpA. I. Increased functional expression of antibody fragments with and without cis-prolines," J. Biol. Chem., Jun. 2, 2000, 275(22):17100-17105.
Bowie, Ju et al., Deciphering the Message in Protein Sequences: Tolerance to Amino Acid Substitutions, Science, 247: 1306-1310 (1990).
Bremer, E. G., et al. "Characterization of a glycosphingolipid antigen defined by the monoclonal antibody MBr1 expressed in normal and neoplastic epithelial cells of human mammary gland." Journal of Biological Chemistry 259.23 (1984): 14773-14777.
Brennan et al., "Preparation of bispecific antibodies by chemical recombination of monoclonal immunoglobulin G1 fragments," Science, Jul. 5, 1985, 229(4708):81-83.
Brodeur et al., Monoclonal Antibody Production Techniques and Applications, Chapter 4: Mouse-Human Myeloma Partners for the Production of Heterohybridomas, Schook, ed., 1987, pp. 51-63, Marcel Dekker, Inc., New York.
Carter et al., "High level *Escherichia coli* expression and production of a bivalent humanized antibody fragment," Nature Biotechnology, Feb. 1992, 10(2):163-167.
Carter et al., "Humanization of an anti-p185$^{HER2}$ antibody for human cancer therapy," Proc. Natl. Acad. Sci. U.S.A., May 15, 1992, 89(10):4285-4289.
Casset, Florence, et al. "A peptide mimetic of an anti-CD4 monoclonal antibody by rational design." Biochemical and Biophysical Research Communications 307.1 (2003): 198-205.
Chang et al., "Potent immune-modulating and anticancer effects of NKT cell stimulatory glycolipids," Proc. Natl. Acad. Sci. USA, Jun. 19, 2007, 104(25):10299-10304.

Chang et al., "Expression of Globo H and SSEA3 in breast cancer stem cells and the involvement of fucosyl transferases 1 and 2 in Globo H synthesis," Proc. Natl. Acad. Sci. U.S.A., Aug. 19, 2008, 105(33):11667-11672.
Chen et al., "Chaperone activity of DsbC," J. Bio. Chem., Jul. 9, 1999, 274(28):19601-19605.
Chen et al., "Selection and analysis of an optimized anti-VEGF antibody: crystal structure of an affinity-matured Fab in complex with antigen," J. Mol. Biol., Nov. 5, 1999, 293(4):865-881.
Chen et al., "Selective killing of transformed cells by cyclin/cyclin-dependent kinase 2 antagonists," Proc. Natl. Acad. Sci. U.S.A., Apr. 13, 1999, 96(8):4325-4329.
Chen, Wei, et al. "Determination of thiols and disulfides via HPLC quantification of 5-thio-2-nitrobenzoic acid." Journal of Pharmaceutical and Biomedical Analysis 48.5 (2008): 1375-1380.
Cheung, Sarah et al., Stage-Specific Embryonic Antigen-3 (SSEA-3) and β3GalT5 are cancer specific and Significant Markers for Breast Cancer Stem Cells, PNAS, Jan. 26, 2016, vol. 113, No. 4, pp. 960-965.
Chothia et al., "Canonical structures for the hypervariable regions of immunoglobulins," J. Mol. Biol., Aug. 20, 1987, 196(4):901-917.
Chou, Ting-Chao and Talalay, Paul, A Simple Generalized Equation for the Analysis of Multiple Inhibitions of Michaelis-Menten Kinetic Systems, J. Biol. Chem. 252:6438-6442, 1977.
Chou, T. C. and Talalay, P., Quantitative Analysis of Dose-Effect Relationships: The Combined Effects of Multiple Drugs or Enzyme Inhibitors. Adv. Enzyme Regul. 22:27-55, 1984.
ClinicalTrials.gov [Internet]. Bethesda (MD): National Library of Medicine (US). Jan. 24, 2012-. Trial of Active Imunotherapy with Globo H-KLH (OPT-822) in Metastatic Breast Cancer Subjects); Jan. 24, 2012 [cited Oct. 11, 2017]; [about 7 screens]. Available from: https:clinicaltrials.gov/ct2/show/NCT01516307.
Clynes, Raphael, et al. "Fc receptors are required in passive and active immunity to melanoma." Proceedings of the National Academy of Sciences 95.2 (1998): 652-656.
Colman, P.M., "Effects of amino acid sequence changes on antibody-antigen interactions," Research in Immunology 145:33-36, 1994.
Cunningham et al., "High-resolution epitope mapping of hGH-receptor interactions by alanine-scanning mutagenesis," Science, Jun. 2, 1989, 244(4908):1081-1085.
Cuzick, J., et al. "Overview of the main outcomes in breast-cancer prevention trials." The Lancet 361.9354 (2003): 296-300.
De Pascalis, Roberto, et al. "Grafting of "abbreviated" complementarity-determining regions containing specificity-determining residues essential for ligand contact to engineer a less immunogenic humanized monoclonal antibody." The Journal of Immunology 169.6 (2002): 3076-3084.
Doronina, Svetlana O., et al. "Development of potent monoclonal antibody auristatin conjugates for cancer therapy." Nature Biotechnology 21.7 (2003): 778-784.
Embleton et al., "In-cell PCR from mRNA: amplifying and linking the rearranged immunoglobulin heavy and light chain V-genes within single cells," Nucl. Acids Res., Aug. 11, 1992, 20(15):3831-3837.
Engels et al., "Gene synthesis [new synthetic methods (77)]," Angew. Chem. Int. Ed. Engl., Jun. 1989, 28(6):716-734.
Evans, T. R. J., and S. B. Kaye. "Vaccine therapy for cancer—fact or fiction?" Q J Med 92.6 (1999): 299-307.
Extended European Search Report, Application No. 15842660.1, dated Mar. 12, 2018, 9 pages.
Fielder, R. J. et al., an Immunogenic Polysaccharide-Protein Conjugate, J. Immunol.,.1970, 105(1), 265-267.
Fitzgerald, Jonathan et al., Systems Biology and Combination Therapy in the Quest for Clinical Efficacy, Nature Chem. Biol. 2(9):458-466, 2006.
Francisco, Joseph A., et al. "cAC10-vcMMAE, an anti-CD30-monomethyl auristatin E conjugate with potent and selective anti-tumor activity." Blood 102.4 (2003): 1458-1465.
Galfrè et al., "Preparation of monoclonal antibodies: strategies and procedures," Methods Enzymol., 1981, 73(Pt B):3-46.
Gazzano-Santoro, Hélène, et al. "A non-radioactive complement-dependent cytotoxicity assay for anti-CD20 monoclonal antibody." Journal of Immunological Methods 202.2 (1997): 163-171.

(56) References Cited

OTHER PUBLICATIONS

Gilewski, Teresa et al., Immunization of Metastatic Breast Cancer Patients with a Fully Synthetic Globo H Conjugate: A Phase I Trial, Proc Natl Acad Sci USA 98:3270-3275, 2001.
Gill et al., "Direct brain infusion of glial cell line-derived neurotrophic factor in Parkinson disease," Nature Med., May 2003, 9(5):589-595 and Addendum from Apr. 2006, 12(4):479.
Goding, Monoclonal Antibodies: Principles and Practice 2nd ed., Chapter 3: Production of Monoclonal Antibodies, 1986, pp. 59-103, Academic Press, London.
Goebel, Walther et al., Chemo-immunological Studies on Conjugated Carbohydrate-Proteins, J. Exp. Med., 1929, 50, 521-531.
Gonnet, GH et al., Exhaustive Matching of the Entire Protein Sequence Database, Science 256: 1443-1445 (1992).
Graham et al., "Characteristics of a human cell line transformed by DNA from human adenovirus type 5," J. Gen. Virol., Jul. 1977, 36(1):59-72.
Gram et al., "In vitro selection and affinity maturation of antibodies from a naive combinatorial immunoglobulin library," Proc. Natl. Acad. Sci. U.S.A., Apr. 15, 1992, 89(8):3576-3580.
Greco, William et al., The Search for Synergy: A Critical Review From a Response Surface Perspective, Pharmacol. Rev. 47(2) :331-385, 1995.
Griffiths et al., "Human anti-self antibodies with high specificity from phage display libraries," EMBO J., Feb. 1993, 12(2):725-734.
Gruber et al., "Efficient tumor cell lysis mediated by a bispecific single chain antibody expressed in *Escherichia coli*," J. Immunol., Jun. 1, 1994, 152(11):5368-5374.
Guss et al., "Structure of the IgG-binding regions of streptococcal protein G," EMBO J., Jul. 1986, 5(7):1567-1575.
Ham, Richard et al., Media and Growth Requirements, Meth. Enz 58, 44-93 (1979).
Hara et al., "Overproduction of penicillin-binding protein 7 suppresses thermosensitive growth defect at low osmolarity due to an spr mutation of *Escherichia coli*," Microbial Drug Resistance, Spring 1996, 2(1):63-72.
Harris, J. Robin, et al. "Keyhole limpet hemocyanin (KLH), II: Characteristic reassociation properties of purified KLH1 and KLH2." Micron 28.1 (1997): 43-56.
Harris, J. R., and J. Mark 1. "Keyhole limpet hemocyanin (KLH): a biomedical review." Micron 30.6 (1999): 597-623.
Hawkins et al., "Selection of phage antibodies by binding affinity. Mimicking affinity maturation," J. Mol. Biol., 1992, 226(3):889-896.
Heffernan, Michael J., et al. "In vivo efficacy of a chitosan/IL-12 adjuvant system for protein-based vaccines." Biomaterials 32.3 (2011): 926-932.
Hernández-Ledesma, Blanca, Chia-Chien Hsieh, and O. Ben. "Lunasin, a novel seed peptide for cancer prevention." Peptides 30.2 (2009): 426-430.
Himmelspach, K. et al., Use of 1-(m-aminophenyl)flavazoles for the Preparation of Immunogens with Oligosaccharide Determinant Groups, Eur. J. Immunol., 1971, 1(2), 106-112.
Hinman et al., "Preparation and characterization of monoclonal antibody conjugates of the calicheamicins: a novel and potent family of antitumor antibiotics," Cancer Res., Jul. 15, 1993, 53(14):3336-3342.
Hirano, Fumiya, et al. "Blockade of B7-H1 and PD-1 by monoclonal antibodies potentiates cancer therapeutic immunity." Cancer Research 65.3 (2005): 1089-1096.
Hogrefe, H.H. et al., "A bacteriophage lambda vector for the cloning and expression of immunoglobulin Fab fragments on the surface of filamentous phage" Gene, 1993, 128(1): 119-126.
Holliger et al., "'Diabodies': small bivalent and bispecific antibody fragments," Proc. Natl. Acad. Sci. U.S.A., Jul. 15, 1993, 90(14):6444-6448.
Holm, Patrik, Rozbeh Jafari, and Birgitta E. Sundström. "Functional mapping and single chain construction of the anti-cytokeratin 8 monoclonal antibody TS1." Molecular Immunology 44.6 (2007): 1075-1084.
Hoogenboom et al., "By-passing immunisation: Human antibodies from synthetic repertoires of germline VH gene segments rearranged in vitro," J. Mol. Biol., Sep. 20, 1992, 227(2):381-388.
Hoogenboom et al., "Multi-subunit proteins on the surface of filamentous phage: methodologies for displaying antibody (Fab) heavy and light chains," Nucl. Acids Res., Aug. 11, 1991 19(15):4133-4137.
Huang, Cheng-Yuan et al., Carbohydrate Microarray for Profiling the Antibodies Interacting with Globo H Tumor Antigen, Proc Natl Acad Sci, 103:15-20, 2006.
Huston, James et al, "Protein Engineering of Antibody Binding Sites: Recovery of Specific Activity in an Anti-Digoxin Single-Chain Fv Analogue Produced in *Escherichia Coli*" Proc. Natl. Acad. Sci. USA, 1988, 85:5879-5883.
International Search Report dated Jan. 8, 2016 in counterpart application PCT/IB2014/002744, 3 pages.
International Search Report and Written Opinion of the International Searching Authority, from corresponding International Patent Application No. PCT/US2015/050270, dated Dec. 15, 2015, 14 Pages.
International Search Report and Written Opinion dated Jul. 7, 2017, from corresponding International Patent Application No. PCT/US2017/024853, by Yu, Cheng-Der Tony et al., "Antibodies, Pharmaceutical Compositions and Methods", filed Mar. 29, 2017, 21 pages.
International Search Report/Written Opinion dated Oct. 31, 2017 in counterpart PCT Application No. PCT/US2017/044244, 13 pages.
International Search Report dated Nov. 28, 2017 in counterpart application PCT/US2017/044713, 6 pages.
International Search Report/Written Opinion dated Mar. 12, 2018 in counterpart PCT Application No. PCT/US17/062886, 22 pages.
Jackson et al., "In vitro antibody maturation: Improvement of a high affinity, neutralizing antibody against IL-1β," J. Immunol., Apr. 1, 1995, 154(7):3310-3319.
Jeon, Insik et al., A Practical Total Synthesis of Globo-H for Use in Anticancer Vaccines, J. Org. Chem., 2009, 74(21), pp. 8452-8455.
Jones et al., "Rapid PCR-cloning of full-length mouse immunoglobulin variable regions," Nature Biotechnol., Jan. 1991, 9(1):88-89.
Jones, "Analysis of polypeptides and proteins," Adv. Drug Delivery Rev., Jan.-Apr. 1993, 10(1):29-90.
Kam et al., "Carbon nanotubes as multifunctional biological transporters and near-infrared agents for selective cancer cell destruction," Proc. Natl. Acad. Sci. U.S.A., Aug. 16, 2005, 102(33):11600-11605.
Kannagi, Reiji, et al. "Stage-specific embryonic antigens (SSEA-3 and -4) are epitopes of a unique globo-series ganglioside isolated from human teratocarcinoma cells." EMBO Journal 2.12 (1983): 2355-2361.
Klussman, Kerry, et al. "Secondary mAb-vcMMAE conjugates are highly sensitive reporters of antibody internalization via the lysosome pathway." Bioconjugate chemistry 15.4 (2004): 765-773.
Komenaka, Ian, Heidi Hoerig, and Howard L. Kaufman "Immunotherapy for melanoma." Clinics in Dermatology 22.3 (2004): 251-265.
Konecny, G. et al., Drug Interactions and Cytotoxic Effects of Paclitaxel in Combination with Carboplatin, Epirubicin, Gemcitabine or Vinorelbine in Breast Cancer Cell Lines and Tumor Samples, Breast Cancer Res. and Treatment 67:223-233, 2001.
Kontermann, "Intrabodies as therapeutic agents," Methods, Oct. 2004, 34(2):163-170.
Kostelny et al., "Formation of a bispecific antibody by the use of leucine zippers," J. Immunol., Mar. 1, 1992, 148(5):1547-1553.
Kozbor, "A human hybrid myeloma for production of human monoclonal antibodies," J. Immunol., Dec. 1984, 133(6):3001-3005.
Kufer, Peter, et al. "A revival of bispecific antibodies." Trends in biotechnology 22.5 (2004): 238-244.
Lee et al "Immunogenicity study of Globo H analogues with modification at the reducing or nonreducing end of the tumor antigen" Journal of the American Chemical Society, (2014) 136(48), 16844-16853.

(56) References Cited

OTHER PUBLICATIONS

Lehninger, Biochemistry: The Molecular Basis of Cell Structure and Function, 2nd ed., 1975, pp. 73-75, Worth Publishers, New York.

Leung et al., "A method for random mutagenesis of a defined DNA segment using a modified polymerase chain reaction," Technique—A Journal of Methods in Cell and Molecular Biology, Aug. 1989, 1(1):11-15.

Lindmark et al., "Binding of immunoglobulins to protein A and immunoglobulin levels in mammalian sera," J. Immunol. Meth., Aug. 12, 1983, 62(1):1-13.

Liu et al., "Eradication of large colon tumor xenografts by targeted delivery of maytansinoids," Proc. Natl., Acad. Sci. U.S.A., Aug. 6, 1996, 93(16):8618-8623.

Liu, Gui, et al. "QS-21 structure/function studies: effect of acylation on adjuvant activity." Vaccine 20.21-22 (2002): 2808-2815.

Lloyd, Kenneth, "Tumor Antigens Known to be Immunogenic in Man" in Specific Immunotherapy of Cancer with Vaccines, 1993, 690, 50-58.

Lode et al., "Targeted therapy with a novel enediyne antibiotic calicheamicin θI1 effectively suppresses growth and dissemination of liver metastases in a syngeneic model of murine neuroblastoma," Cancer Res., Jul. 15, 1998, 58(14):2925-2928.

Lou, et al., Stage-specific embryonic antigent-4 as a potential therapeutic target in glioblastoma multiforms and other cancers. Proc Natl Acad Sci USA 2014, 111(7):2482-7.

Lucas, A.H. et al., Carbohydrate Moieties as Vaccine Candidates: Meeting Summary, Vaccine, vol. 28(4), Jan. 2010, pp. 1121-1131.

Mandler et al., "Immunoconjugates of geldanamycin and anti-HER2 monoclonal antibodies: antiproliferative activity on human breast carcinoma cell lines," J. Nat. Cancer Inst., Oct. 4, 2000, 92(19):1573-1581.

Mandler et al., "Modifications in synthesis strategy improve the yield and efficacy of geldanamycin-herceptin immunoconjugates," Bioconjugate Chem., Jul.-Aug. 2002, 13(4):786-791.

Mandler et al., "Synthesis and evaluation of antiproliferative activity of a geldanamycin-Herceptin™ immunoconjugate," Bioorganic & Med. Chem. Letters, May 15, 2000, 10(10):1025-1028.

Mao, Shenlan, et al. "Phage-display library selection of high-affinity human single-chain antibodies to tumor-associated carbohydrate antigens sialyl Lewisx and Lewisx." Proceedings of the National Academy of Sciences 96.12 (1999): 6953-6958.

Mao, Weiguang, et al. "EphB2 as a therapeutic antibody drug target for the treatment of colorectal cancer." Cancer Research 64.3 (2004): 781-788.

Marasco et al., "Design, intracellular expression, and activity of a human anti-human immunodeficiency virus type 1 gp120 single-chain antibody," Proc. Natl. Acad. Sci. U.S.A., Aug. 15, 1993, 90(16):7889-7893.

Marasco, "Intrabodies: turning the humoral immune system outside in for intracellular immunization," Gene Therapy, Jan. 1997, 4(1):11-15.

Martineau, R.S. et al., Immunochemical Studies on a Panosyl-Azoprotein conjugate, Immunochemistry, vol. 8, 705-718, 1971.

Mather et al., "Culture of testicular cells in hormone-supplemented serum-free medium," Annals N.Y. Acad. Sci., 1982, 383:44-68.

Mather, "Establishment and characterization of two distinct mouse testicular epithelial cell lines," Biol. Reprod., Aug. 1980, 23(1):243-252.

Matsuda, F. et al., "Structure and physical map of 64 variable segments in the 3' 0.8-megabase region of the human immunoglobulin heavy-chain locus." Nature Genet., 1993, 3: 88-94.

McCafferty et al., "Phage antibodies: Filamentous phage displaying antibody variable domains," Nature, Dec. 6, 1990, 348:552-554.

Miller, Kathy, et al. "Design, construction, and in vitro analyses of multivalent antibodies." The Journal of Immunology 170.9 (2003): 4854-4861.

Milstein, C & Cuello, AC, Hybrid Hydridomas and their use in immunohistochemistry, Nature 305, 537-540, Oct. 1993.

Morimoto et al., "Single-step purification of F(ab')2 fragments of mouse monoclonal antibodies (immunoglobulins G1) by hydrophobic interaction high performance liquid chromatography using TSKgel Phenyl-5PW," J. Biochem. Biophys. Meth., Mar. 1992, 24(1-2):107-117.

Munson et al., "Ligand: a versatile computerized approach for characterization of ligand-binding systems," Anal. Biochem., Sep. 1, 1980, 107(1):220-239.

Neuberger et al., "Recombinant antibodies possessing novel effector functions," Nature, Dec. 13-19, 1984, 312(5995):604-608.

Niculescu-Duvaz et al., "Antibody-directed enzyme prodrug therapy (ADEPT): A review," Adv. Drg. Del. Rev., Jul. 7, 1997, 26(2-3):151-172.

Nikula, Kristen et al., Animal Models of Chronic Bronchitis and Their Relevance to Studies of Particle-Induced Disease, Inhal. Toxicol. 4(12): 123-153, 2000.

Office Action issued in corresponding Taiwan patent application No. 103131876, dated Dec. 26, 2016, 7 pages.

Orlandi et al., "Cloning immunoglobulin variable domains for expression by the polymerase chain reaction," Proc. Natl. Acad. Sci. U.S.A., May 1989, 86(10):3833-3837.

Ørum et al., "Efficient method for constructing comprehensive murine Fab antibody libraries displayed on phage." Nucleic Acids Res., Sep. 25, 1993, 21(19):4491-4498.

Oxenius, Annette, et al. "CpG-containing oligonucleotides are efficient adjuvants for induction of protective antiviral immune responses with T-cell peptide vaccines." Journal of Virology 73.5 (1999): 4120-4126.

Papanastassiou et al., "The potential for efficacy of the modified (ICP 34.5-) herpes simplex virus HSV1716 following intratumoural injection into human malignant glioma: a proof of principle study," Gene Therapy, Mar. 2002, 9(6):398-406.

Paul, William E. "Structure and Function of Immunoglobulins, Fundamental Immunology." Chapter 9 (1993), 3rd Edition: 292-295.

Pearson, William, Using the FASTA Program to Search Protein and DNA Sequence Databases, Methods Mol. Biol. 243:307-331, 1994.

Pegram, Mark et al., Inhibitory Effects of Combinations of HER-2/neu Antibody and Chemotherapeutic Agents Used for Treatment of Human Breast Cancers, Oncogene 18:2241-2251, 1999.

Pegram, Mark et al., Rational Combinations of Trastuzumab With Chemotherapeutic Drugs Used in the Treatment of Breast Cancer, J. of the Nat. Cancer Inst. 96(10):739-749, 2004.

Plückthun, "Mono- and bivalent antibody fragments produced in *Escherichia coli*: Engineering, folding and antigen binding," Immunol. Rev., Dec. 1992, 130:151-188.

Plückthun, Handbook of Experimental Pharmacology, vol. 113: The Pharmacology of Monoclonal Antibodies, Chapter 11: Antibodies from *Escherichia coli*, Rosenberg et al., eds., 1994, pp. 269-315, Springer-Verlag, Berlin.

Presta et al., "Humanization of an antibody directed against IgE," J. Immunol., Sep. 1, 1993, 151(5):2623-2632.

Presta et al., "Humanization of an anti-vascular endothelial growth factor monoclonal antibody for the therapy of solid tumors and other disorders," Cancer Res., Oct. 15, 1997, 57(20):4593-4599.

Presta, Leonard G. "Antibody engineering." Current Opinion in Biotechnology 3.4 (1992): 394-398.

Proba et al., "Functional antibody single-chain fragments from the cytoplasm of *Escherichia coli*: influence of thioredoxin reductase (TrxB)," Gene, Jul. 4, 1995, 159(2):203-207.

Queen, Cary et al, A Humanized Antibody that Binds to the Interleukin 2 Receptor, Proc Natl Acad Sci., 86: 10029-10033 (1989).

Ragupathi, Govindaswami et al., Immunization of Mice with a Fully Synthetic Globo H Antigen Results in Antibodies against Human Cancer Cells: A Combined Chemical-Immunological Approach to the Fashioning of an Anticancer Vacine, Angew Chem Int, 36(1-2), 125-128, Feb. 1997.

Immunological Approach to the Fashioning of an Anticancer Vaccine, Angew Chem Int, 36(1-2), 125-128, Feb. 1997.

(56) References Cited

OTHER PUBLICATIONS

Ragupathi, Govindaswami, et al. "Constructing an adenocarcinoma vaccine: Immunization of mice with synthetic KH-1 nonasaccharide stimulates anti-KH-1 and anti-Le$^y$ antibodies." International Journal of Cancer 99.2 (2002): 207-212.
Ramm et al., "The periplasmic *Escherichia coli* peptidylprolyl cis,trans-isomerase FkpA. II. Isomerase-independent chaperone activity in vitro," J. Biol. Chem., Jun. 2, 2000, 275(22):17106-17113.
Ravetch et al., "Fc receptors," Annu. Rev. Immunol., 1991, 9:457-492.
Reyes et al., "Expression of human β-interferon cDNA under the control of a thymidine kinase promoter from herpes simplex virus," Nature, Jun. 17, 1982, 297(5867):598-601.
Rowland et al, "Drug localisation and growth inhibition studies of vindesine-monoclonal anti-CEA conjugates in a human tumour xenograft," Cancer Immunol. Immunother., 1986, 21(3):183-187.
Rüde, Erwin et al., Synthesis of the N-carboxy-α-amino Acid Anhydrides of Several O-acetylated Serine Glycosides, Carbohydr. Research, 1968, 8(2), 219-232.
Rudikoff, Stuart, et al. "Single amino acid substitution altering antigen-binding specificity." Proceedings of the National Academy of Sciences 79.6 (1982): 1979-1983.
Sastry et al., "Cloning of the immunological repertoire in *Escherichia coli* for generation of monoclonal catalytic antibodies: construction of a heavy chain variable region-specific cDNA library," Proc. Natl. Acad. Sci. U.S.A., Aug. 1989, 86(15):5728-5732.
Schier et al., "Identification of functional and structural amino-acid residues by parsimonious mutagenesis," Gene, Mar. 9, 1996, 169(2):147-155.
Schiffman, Mark, and Philip E. Castle. "The promise of global cervical-cancer prevention." New England Journal of Medicine 353.20 (2005): 2101-2104.
Search Report issued in corresponding Taiwan patent application No. 103131876, prepared Dec. 20, 2016, 1 page.
Sedlik, Christine et al., Effective Antitumor Therapy Based on a Novel Antibody-Drug Conjugate Targeting the Tn Carbohydrate Antigen, Oncoimmunology, Jul. 2016, vol. 5, No. 7, e1171434-1-13.
Shalaby et al., "Development of humanized bispecific antibodies reactive with cytotoxic lymphocytes and tumor cells overexpressing the HER2 protooncogene," J. Exp. Med., Jan. 1, 1992, 175(1):217-225.
Siebenlist et al., "*E. coli* RNA polymerase interacts homologously with two different promoters," Cell, Jun. 1980, 20(2):269-281.
Sigma-Aldrich, Product Information for Hemocyanin From Megathura Crenulata, Catalog No. H7017, 1 Page, 2016.
Simmons et al., "Expression of full-length immunoglobulins in *Escherichia coli*: Rapid and efficient production of aglycosylated antibodies," J. Immunol. Methods, May 1, 2002, 263(1-2):133-147.
Sims et al., "A humanized CD18 antibody can block function without cell destruction," J. Immunol., Aug. 15, 1993, 151(4):2296-2308.
Sjölander, A., et al. "ISCOMs: an adjuvant with multiple functions." J. Leukocyte Biol. 64.6 (1998): 713-723.
Skerra, "Bacterial expression of immunoglobulin fragments," Curr. Opinion in Immunol., Apr. 1993, 5(2):256-262.
Slovin, S.F. et al., Carbohydrate Vaccines in Cancer: Immunogenicity of a Fully Synthetic Globo H Hexasaccharide Conjugate in Man, Proc Natl Acad Sci, 96:5710-5715, May 1999.
Sonderstrup, Grete, Development of Humanized Mice as a Model of Inflammatory Arthritis, Springer Sem. Immunopathol. 25: 35-45, 2003.
Speed, Margaret A., Daniel IC Wang, and Jonathan King. "Multimeric intermediates in the pathway to the aggregated inclusion body state for P22 tailspike polypeptide chains." Protein Science 4.5 (1995): 900-908.
Sun, Hongfan, Kevin GJ Pollock, and James M. Brewer. "Analysis of the role of vaccine adjuvants in modulating dendritic cell activation and antigen presentation in vitro." Vaccine 21.9-10 (2003): 849-855.
Suresh et al., "Bispecific monoclonal antibodies from hybrid hybridomas," Methods in Enzymology, 1986, 121:210-228.
Syrigos et al., "Antibody directed enzyme prodrug therapy (ADEPT): a review of the experimental and clinical considerations," Anticancer Research, Jan.-Feb. 1999, 19(1A):605-614.
Takeda et al., "Construction of chimaeric processed immunoglobulin genes containing mouse variable and human constant region sequences," Nature, Apr. 4-10, 1985, 314(6010):452-454.
Thorpe, (1985) "Antibody Carriers of Cytotoxic Agents in Cancer Therapy: A Review," in Monoclonal Antibodies '84: Biological and Clinical Applications, A. Pinchera et al. (Ed.s), pp. 475-506.
Tomlinson, I.M. et al., "The repertoire of human germline $V_H$ sequences reveals about fifty groups of $V_H$ segments with different hypervariable loops" J. Mol. Biol., Oct. 5, 1992, 227(3): 776-798.
Toyokuni, Tatsushi et al., Synthetic Vaccines: Synthesis of a Dimeric Tn Antigen-Lipopeptide Conjugate That Elicits Immune Responses Against Tn-Expressing Glycoproteins, J. Am. Chem. Soc., 1994, 116(1), 395-396.
Traunecker et al., "Bispecific single chain molecules (Janusins) target cytotoxic lymphocytes on HIV infected cells," EMBO J., Dec. 1991, 10(12):3655-3659.
Tutt et al., "Trispecific F(ab')$_3$ derivatives that use cooperative signaling via the TCR/CD3 complex and CD2 to activate and redirect resting cytotoxic T cells," J. Immunol., Jul. 1, 1991, 147(1):60-69.
Urlaub et al., "Isolation of Chinese hamster cell mutants deficient in dihydrofolate reductase activity." Proc. Natl. Acad. Sci. U.S.A., Jul. 1980, 77(7):4216-4220.
Vajdos, Felix F., et al. "Comprehensive functional maps of the antigen-binding site of an anti-ErbB2 antibody obtained with shotgun scanning mutagenesis." Journal of Molecular Biology 320.2 (2002): 415-428.
Verhoeyen et al., "Reshaping human antibodies: grafting an antilysozyme activity," Science, Mar. 25, 1988, 239(4847):1534-1536.
Wakimoto, Hiroaki, et al. "Intensified antitumor immunity by a cancer vaccine that produces granulocyte-macrophage colony-stimulating factor plus interleukin 4." Cancer Research 56.8 (1996): 1828-1833.
Ward et al., "Binding activities of a repertoire of single immunoglobulin variable domains secreted from *Escherichia coli*," Nature, Oct. 12, 1989, 341(6242):544-546.
Waterhouse et al., "Combinatorial infection and in vivo recombination: a strategy for making large phage antibody repertoires," Nuc. Acids Res., May 11, 1993, 21(9):2265-2266.
Williams, S.C. and Winter, G. "Cloning and sequencing of human immunoglobulin $V_\lambda$ gene segments" Eur. J. Immunol., 1993, 23: 1456-1461.
Wilman, "Prodrugs in Cancer Chemotherapy" Biochemical Society Transactions, 14, pp. 375-382, 615th Meeting Belfast, 1986.
Winter et al., "Making antibodies by phage display technology," Annu. Rev. Immunol., 1994, 12:433-455.
Yaniv, Moshe, Enhancing Elements for Activation of Eukaryotic Promoters, Nature 297: 17-18, 1982.
Yansura et al., "Nucleotide sequence selection for increased expression of heterologous genes in *Escherichia coli*," Methods: A Companion to Methods in Enzymol., Aug. 1992, 4(2):151-158.
Yelton et al., "Affinity maturation of the BR96 anti-carcinoma antibody by codon-based mutagenesis." J. Immunol., Aug. 15, 1995, 155(4):1994-2004.
Zhou, Zhifang et al., A Fully Synthetic Self-Adjuvanting Globo H-Based Vaccine Elicited Strong T Cell-Mediated Antitumor Immunity, Chem. Sci., 2015, 6, 7112-7121.
Zhu, Jianglong et al., From Synthesis to Biologics: Preclinical Data on a Chemistry Derived Anticancer Vaccine, J. Am. Chem. Soc. 131(26):9298-9303, 2009.
Bertozzi, CR et al., Glycans in Cancer and Inflammation—Potential for Therapeutics and Diagnostics, Nat Rev Drug Discovery, 2005, 4, 477-488.
Bosse, Folkert et al., Linear Synthesis of the Tumor-Associated Carbohydrate Antigens Globo-H, SSEA-3, and Gb3, J Org Chem. 67(19):6659-70, 2002.

(56) References Cited

OTHER PUBLICATIONS

Brüggemann et al., "Designer mice: the production of human antibody repertoires in transgenic animals," *Year in Immunol.*, 1993, 7:33-40.
Clackson et al., "Making antibody fragments using phage display libraries," *Nature*, Aug. 15, 1991, 352(6336):624-628.
Eller, Chelcie et al., Human Cancer Antigen Globo H Is a Cell-Surface Ligand for Human Ribonuclease 1, ACS Central Science. vol. 1, p. 181-90, Jul. 13, 2015.
Fellouse et al., "Synthetic antibodies from a four-amino-acid code: a dominant role for tyrosine in antigen recognition," *Proc. Natl. Acad. Sci. U.S.A.*, Aug. 24, 2004, 101(34):12467-12472.
Fishwild et al., "High-avidity human IgGK monoclonal antibodies from a novel strain of minilocus transgenic mice," *Nature Biotechnol.*, Jul. 1996, 14(7):845-851.
Gijsen, H.J. et al., Recent Advances in the Chemoenzymatic Synthesis of Carbohydrates and Carbohydrate Mimetics, Chem. Rev., 96, 443-473, 1996.
Hakomori et al., "Glycosphingolipid antigens and cancer therapy," *Chem. Biol.*, Feb. 1997, 4(2):97-104.
Hakomori, Sen-Itiroh, Tumor-associated carbohydrate antigens defining tumor malignancy: Basis for development of and- cancer vaccines, 2001, Advances in Experimental Medicine and Biology. 491 :369-402.
Hammerling et al., in: Monoclonal Antibodies and T-Cell Hybridomas 563-587, 1981.
Harris, "Production of humanized monoclonal antibodies for in vivo imaging and therapy," *Biochem. Soc. Transactions*, Nov. 1995, 23(4):1035-1038.
Hirabayashi, J. et al., Oligosaccharide Microarrays for Glycomics, Trends in Biotechnology 21 (4): 141-143, 2003.
Hurle et al., "Protein engineering techniques for antibody humanization," Curr. Opin. Biotechnol., Aug. 1994, 5(4):428-433.
International Search Report and Written Opinion of the International Searching Authority, PCT/US16/50252, Nov. 17, 2016, 12 Pages.
Jakobovits et al., "Germ-line transmission and expression of a human-derived yeast artificial chromosome," Nature, Mar. 18, 1993, 362(6417):255-258.
Jakobovits et al., "Analysis of homozygous mutant chimeric mice: deletion of the immunoglobulin heavy-chain joining region blocks B-cell development and antibody production," *Proc Natl. Acad. Sci. U.S.A.*, Mar. 15, 1993, 90(6):2551-2555.
Jones et al., "Replacing the complementarity-determining regions in a human antibody with those from a mouse," *Nature*, May 29-Jun. 4, 1986, 321(6069):522-525.
Kannagi et al., "New globoseries glycosphingolipids in human teratocarcinoma reactive with the monoclonal antibody directed to a developmentally regulated antigen, stage-specific embryonic antigen 3," *J. Biol. Chem.*, Jul. 25, 1983, 258(14):8934-8942.
Koeller, Kathryn et al., Enzymes for Chemical Synthesis, Nature, 409, 232-240, 2001.
Köhler et al., "Continuous cultures of fused cells secreting antibody of predefined specificity," *Nature*, Aug. 7, 1975, 256(5517):495-497.
Krainer, Florian et al., An Updated View on Horseradish Peroxidases: Recombinant Production and Biotechnological Applications, Applied Microbiology and Biotechnology, vol. 99, p. 1611-1625, Jan. 11, 2015.
Lee et al., "Bivalent antibody phage display mimics natural immunoglobulin," *J. Immunol. Methods*, Jan. 2004, 284(1-2):119-132.
Lee et al., "High-affinity human antibodies from phage-displayed synthetic Fab libraries with a single framework scaffold," *J. Mol. Biol.*, Jul. 23, 2004, 340(5):1073-1093.
Livingston, Philip, Seminars in Cancer Biology, Cancer Biol, 6(6):357-366, 1995.
Lonberg et al., "Human antibodies from transgenic mice," *Int. Rev. Immunol.*, 1995, 13(1):65-93.

Lonberg et al., "Antigen-specific human antibodies from mice comprising four distinct genetic modifications," *Nature*, Apr. 28, 1994, 368(6474):856-859.
Marks et al., "By-passing immunization: Building high affinity human antibodies by chain shuffling," *Nature Biotechnology*, Jul. 1992, 10(7):779-783.
Marks et al., "By-passing immunization. Human antibodies from V-gene libraries displayed on phage," *J. Mol. Biol.*, Dec. 5, 1991, 222(3):581-597.
Menard S et al., Generation of Monoclonal Antibodies Reacting with Normal and Cancer Cells of Human Breast, Cancer Res 43: 1295-1300, 1983.
Morrison et al., "Chimeric human antibody molecules: mouse antigen-binding domains with human constant region domains," *Proc. Natl. Acad. Sci. U.S.A.*, Nov. 1984, 81(21):6851-6855.
Morrison, "Immunology. Success in specification," *Nature*, Apr. 28, 1994, 368(6474):812-813.
Nicolaou et al., "Calicheamicin $\Theta^I_1$: A rationally designed molecule with extremely potent and selective DNA cleaving properties and apoptosis inducing activity," *Angew. Chem. Intl. Ed. Engl.*, Feb. 1, 1994, 33(2):183-186.
Neuberger, "Generating high-avidity human Mabs in mice," *Nature Biotechnol.*, Jul. 1996, 14(7):826.
Presta, "Antibody engineering," *Curr. Opin. Struct. Biol.*, Aug. 1992, 2(4):593-596.
Riechmann et al., "Reshaping human antibodies for therapy," *Nature*, Mar. 24, 1988, 332(6162):323-327.
Sidhu et al., "Phage-displayed antibody libraries of synthetic heavy chain complementarity determining regions," *J. Mol. Biol.*, Apr. 23, 2004, 338(2):299-310.
Vaswani et al., "Humanized antibodies as potential therapeutic drugs," *Ann. Allergy, Asthma Immunol.*, Aug. 1998, 81(2):105-116, 119.
Wilen et al., "Strategies in optical resolutions," Tetrahedron, 1977, 33(21):2725-2736.
Wymer, Nathan et al., Enzyme-Catalyzed Synthesis of Carbohydrates, Curr. Opin. Chem. Biol., 4, 110-119, 2000.
Zhang et al., "Selection of tumor antigens as targets for immune attack using immunohistochemistry: I. Focus on gangliosides," *Int. J. Cancer*, Sep. 26, 1997,73(1):42-49.
Arigi, Emma, et al. "Design of a covalently bonded glycosphingolipid microarray." Glycoconjugate Journal 29.1 (2012): 1-12.
Liang, Pi-Hui, et al. "Quantitative Microarray Analysis of Intact Glycolipid—CD1d Interaction and Correlation with Cell-Based Cytokine Production." Journal of the American Chemical Society 130.37 (2008): 12348-12354.
Wallner, Fredrik K., et al. "Solid-phase synthesis of serine-based glycosphingolipid analogues for preparation of glycoconjugate arrays." Organic & Biomolecular Chemistry 3.2 (2005): 309-315.
Feng, Li. "Probing lipid-protein interactions using lipid microarrays." Prostaglandins & other lipid mediators 77.1-4 (2005): 158-167.
Schwarz, Mikael, et al. "A new kind of carbohydrate array, its use for profiling antiglycan antibodies, and the discovery of a novel human cellulose-binding antibody." Glycobiology 13.11 (2003): 749-754.
Wang, Cheng-Chi, et al. "Glycan microarray of Globo H and related structures for quantitative analysis of breast cancer." Proceedings of the National Academy of Sciences 105.33 (2008): 11661-11666.
Danishefsky, Samuel J., et al. "Development of Globo-H cancer vaccine." Accounts of chemical research 48.3 (2015): 643-652.
Grant, Oliver C., et al. "Presentation, presentation, presentation! Molecular-level insight into linker effects on glycan array screening data." Glycobiology 24.1 (2014): 17-25.
Huang, Yen-Lin, et al. "Carbohydrate-based vaccines with a glycolipid adjuvant for breast cancer." Proceedings of the National Academy of Sciences 110.7 (2013): 2517-2522.
Huang, Yen-Lin, and Chung-Yi Wu. "Carbohydrate-based vaccines: challenges and opportunities." Expert Review of Vaccines 9.11 (2010): 1257-1274.

(56) References Cited

OTHER PUBLICATIONS

Extended European Search Report from corresponding European App. No. 16843131.0, dated Feb. 14, 2019, 13 Pages.

* cited by examiner

Lipid-NH2:

Lipid-analogues:

Synthesis of Globo H-lipid-1

Synthesis of Globo H-lipid-2

Synthesis of Globo H-lipid-3

Synthesis of Globo H-lipid-4

Synthesis of Globo H-lipid-6

Synthesis of Globo H-lipid-1 (racemic)

Mass spectrum of Globo H-lipid 1

Mass spectrum of Globo H-lipid 2

Mass spectrum of Globo H-lipid 3

(Mass spectrum, positive mode, m/z range: 1500~2000)

Mass spectrum of Globo H-lipid 4

(Mass spectrum, m/z range: 1700~1800)

Mass spectrum of Globo H-lipid 6

(Mass spectrum, negative ion, zoom-in on m/z range: 1798~1812)

Mass spectrum of Globo H-lipid 1(racemic)

(Mass spectrum, positive mode, m/z range: 1500~1700)

Synthesis of SSEA-3-lipid 1

Mass spectrum of SSEA-3-lipid 1

Synthesis of SSEA-4-lipid 1

Mass spectrum of SSEA-4-lipid 1

Globo H-ceramide

Anti-Globo H IgM

Globo H-lipid 1

Anti-Globo H IgM

Anti-SSEA-3 IgM

SSEA-3-ceramide

Anti-Globo H IgG

Globo H-lipid 1

SSEA-4-lipid 1

Globo H-lipid 1

SSEA-4-lipid 1

Globo H-lipid 1

SSEA-4-lipid 1

Globo H-lipid 1

SSEA-3-lipid 1

SSEA-4-lipid 1

Globo H-lipid 1

SSEA-3-lipid 1

SSEA-4-lipid 1

US 10,935,544 B2

GLYCAN ARRAYS AND METHOD OF USE

FIELD

The invention relates to linkers and methods for generating arrays with linkers. The invention also relates to methods for identifying agents that bind to various types of molecules on the arrays and to defining the structural elements of the molecules on the arrays that bind to those agents. The arrays and methods provided herein may be used for epitope identification, drug discovery and as analytical tools. The invention provides useful glycans and epitope determinants that are useful in detecting, diagnosing, recurrence monitoring and preventing cancer.

BACKGROUND OF THE INVENTION

Glycans are typically the first and potentially the most important interface between cells and their environment. As vital constituents of all living systems, glycans are involved in recognition, adherence, motility and signaling processes: (1) all cells in living organisms, and viruses, are coated with diverse types of glycans; (2) glycosylation is a form of post- or co-translational modification occurring in all living organisms; and (3) altered glycosylation is an indication of an early and possibly critical point in development of human pathologies. (Jun Hirabayashi, Oligosaccharide microarrays for glycomics, 2003, *Trends in Biotechnology.* 21(4): 141-143; Sen-Itiroh Hakomori, Tumor-associated carbohydrate antigens defining tumor malignancy: Basis for development of and-cancer vaccines, 2001, *Advances in Experimental Medicine and Biology.* 491:369-402.) These cell-identifying glycosylated molecules include glycoproteins and glycolipids and are specifically recognized by various glycan-recognition proteins, called 'lectins.' However, the enormous complexity of these interactions, and the lack of well-defined glycan libraries and analytical methods have been major obstacles in the development of glycomics.

The development of nucleotide and protein microarrays has revolutionized genomic, gene expression and proteomic research. While the pace of innovation of these arrays has been explosive, the development of glycan microarrays has been relatively slow. One reason for this is that it has been difficult to reliably immobilize populations of chemically and structurally diverse glycans. Moreover, glycans are not readily amenable to analysis by many of the currently available molecular techniques (such as rapid sequencing and in vitro synthesis) that are routinely applied to nucleic acids and proteins.

Globo H, SSEA-3 and SSEA-4 (the globo series of carbohydrate glycans) and Sialyl Lewis A (SLe$^a$), Lewis A (Le$^y$), Sialyl Lewis X (SLe$^x$), and Lewis X (Le$^x$) are antigens expressed on the surface of cancer cells and are specific to a wide range of different cancer types, including breast, pancreatic, gastric, colorectal, lung, oral, ovarian and prostate.

Globo H is a hexasaccharide having the structure (Fuc α1→2 Gal β1→3 GalNAc β1→3 Gal α1→4 Gal β1→4 Glc), which is a member of a family of antigenic carbohydrates that are highly expressed on a various types of cancers, especially cancers of breast, prostate and lung (Kannagi R, et al. *J Biol Chem* 258:8934-8942, 1983; Zhang S L, et al. hit *J Cancer* 73:42-49, 1997; Hakomori S, el al. *Chem Biol* 4:97-104, 1997; Dube D H, et al. *Nat Rev Drug Discov* 4:477-488, 2005). Globo H is expressed on the cancer cell surface as a glycolipid and possibly as a glycoprotein (Menard S, et al. *Cancer Res* 43:1295-1300, 1983; Livingston P O *Cancer Biol* 6:357-366, 1995). The serum of breast cancer patients contains high levels of antibodies against the Globo H epitope (Menard S, et al. *Cancer Res* 43:1295-1300, 1983).

SSEA-3, also known as stage-specific embryonic antigen-3, Globopentaose, also known as Gb5 and having the structure (2Gal β1→3GalNAc β1→3Gal α1→4Gal β1→4Glcβ1); and SSEA-4, also known as stage-specific embryonic antigen-4 and having the structure (Neu5Ac α2→3Gal β1→3GalNAc β1→3Gal α1→4Gal β1-4Glcβ1) are analogues of Globo H. Sialyl Lewis X (SLe$^x$) is a tetrasaccharide having the structure α-NeuNAc-(2→3)-β-D-Gal-(1→4)(α-L-Fuc-[1→3])-D-GlcNAc, 3'-SLe$^x$. Sialyl Lewis A (SLe$^a$) is a tetrasaccharide having the structure α-NeuNAc-(2→3)-β-D-Gal-(1→3)-(α-L-Fuc-[1→4])-D-GlcNAc, 3'-SLe$^a$. Le$^x$, also known as Le$^x$ has the structure Galβ1-4(Fucα1-3)GlcNAcβ-. Ley, also known as Le$^y$, has the structure Fucα1-2Galβ1-4(Fucα 1-3)GlcNAcβ-.

SUMMARY OF THE INVENTION

The present disclosure relates in one aspect to linker compositions and methods of use thereof which can facilitate efficient detection and binding of glycans, for example, the globoseries glycans (globoseries glycosphingolipid antigens) and/or tumor associated carbohydrate antigens (TACAs). For example, see FIG. 1. In addition, the term "globoseries glycans pathway" refers to a biosynthetic pathway of glycosphingolipids described in FIG. 2.

TACAs can be divided into two classes: glycoprotein antigens and glycolipid antigens. Glycoprotein antigens can include or exclude, for example: (1) Mucins can include or exclude, for example: α-2,6-N-acetylgalactosaminyl (Tn), Thomsen-Friendreich (TF), and Sialyl-Tn (sTn) and (2) Polysialic acid (PSA). Glycolipid antigens can include or exclude, for example: (1) Globo series antigens can include or exclude, for example: Globo H, SSEA-3 (or Gb5), SSEA-4, Gb3 and Gb4; (2) Blood group determinants can include or exclude, for example: Lewis' (Le$^x$), Lewis$^y$ (Le$^y$), Lewis$^a$ (Le$^a$), Sialyl Lewis$^x$ (sLe$^x$), and Sialyl Lewis$^a$ (SLe$^a$) and (3) Gangliosides can include or exclude, for example: GD1a, GT1b, A2B5, GD2, GD3, GM1, GM2, GM3, fucosyl-GM1, and Neu5GcGM3.

In one aspect, the invention provides linkers that may be used in a variety of applications. For example, the linkers of the invention may be used to attach molecules to substrates, which can include or exclude: surfaces, solid surfaces, particles, arrays or beads. The linker may, in some aspects, comprise a first moiety that interacts with a carbohydrate and a second moiety that interacts with a surface.

In some aspects, this disclosure provides linkers, and conjugates of linkers and glycans, which can include or exclude: linker-TACAs, including linker-globoseries glycans or other TACAs, linker-globo series glycoprotein conjugates, and methods of making and using the same. Exemplary globoseries glycans can include or exclude SSEA-3, SSEA-4, and Globo H. Exemplary globoseries glycoprotein can include or exclude SSEA-3, SSEA-4, and Globo H attached to a peptide or protein. Additional TACA glycans can include or exclude, for example, Le$^y$, SLe$^a$, and SLe$^x$. TACAs also comprise n-pentylamine-functionalized variants of any of the exemplary glycans, for example, n-pentylamine-functionalized variants of SSEA-3, SSEA-4, Gb3, Gb4, Globo H, Le$^y$, SLe$^a$, and SLe$^x$.

In some aspects, this disclosure provides glycans conjugated to substrates, including by means of a linker.

In some aspects, the present disclosure relates to an array of carbohydrates immobilized on a substrate, the array comprising: a plurality of G-A-Z carbohydrates, each G-A-Z moiety deposited at a discrete location on the substrate, wherein G is one or more TACAs; A is a moiety comprising an alkyl, ester or amide; Z is selected from one or a plurality of lipid chains and a spacer group linked to one or a plurality of lipid chains.

The invention also provides glycan arrays (or microarrays) with linkers, and methods for making such glycan arrays or microarrays. In some aspects, the invention provides methods for detecting binding complexes between carbohydrates on the arrays and molecules from a sample. In some aspects, the invention provides methods for using such arrays to identify and analyze the interactions that various types of glycans have with other molecules. Said glycan arrays and screening methods may be useful for identifying carbohydrate binding partners, for example, glycan binding proteins, receptors, antibodies, antibody fragments or nanoparticles, nucleic acids, aptamers, lectins, or other molecule or substance will bind to which glycan. Thus, the glycan libraries and glycan arrays of the invention may be used for glycan-binding partner characterization, receptor ligand characterization, detection of binding complexes and their binding strength, identification of carbohydrates on cell membranes and within subcellular components, antibody epitope identification, enzyme characterization and library screening, such as phage display library screening. In one aspect, the invention provides an array of glycans where the glycans are attached to the array by a linker molecule, such as a linker molecule as disclosed herein.

In some aspects, the present disclosure relates to (a) contacting a sample comprising carbohydrate binding moieties with an array of one or more tumor associated carbohydrates immobilized on a substrate, the array comprising: a plurality of carbohydrates immobilized at discrete locations on a surface of the solid substrate (b) forming a complex between one or more immobilized carbohydrates and at least one carbohydrate binding moiety suspected of specifically binding to the carbohydrate; and (c) detecting the complex. The detecting may comprise detecting a detectable label or reporter coupled to the molecules or a secondary binding molecule specific for the first binding molecule, wherein the intensity of a reporter signal generated on the surface of the (optionally coated) solid substrate is detectable with higher sensitivity than on a functionalized substrate. The carbohydrate binding moieties may include or exclude: molecules, antibodies, shed antigens, secreted proteins, cells, subcellular fragments or other cellular components in the sample. In some aspects, this invention relates to an array of carbohydrates immobilized on a substrate, the array comprising: a plurality of carbohydrates immobilized at discrete locations on a surface of the solid substrate, whereby (a) the immobilized carbohydrates, which comprise one or more tumor associated carbohydrate antigens (TACAs), can be assayed by detection methods and/or reagents; and (b) analysis of binding reactions between the immobilized carbohydrates and a first binding molecules suspected of specifically binding to the carbohydrates can be performed; wherein the method comprises detecting a detectable label or reporter coupled to the molecules or a secondary binding molecule specific for the first binding molecule and wherein the intensity of a reporter signal generated on the surface of the (coated) solid substrate is detectable with higher sensitivity than on a functionalized substrate; is provided. The substrate may be, in some aspects, a surface, solid surface, non-transparent solid, a solid transparent to selected wavelengths of visible or non-visible light, a particle, an array, a microbubble, or a bead. In some aspects the substrate may be coated. In certain aspects, the array can be assayed by detecting the binding reactions or detecting the complexes between the immobilized carbohydrates and clinical samples; wherein the method comprising detecting a imaging tag coupled to an antibody specific for the clinical samples. In some aspects, the first antibody can be directly tagged to a reporter molecule.

In one aspect, the TACA comprises Globo H.
In one aspect, the TACA comprises SSEA-3.
In one aspect, the TACA comprises SSEA-4.
In one aspect, the TACA comprises $SLe^x$.
In one aspect, the TACA comprises $SLe^a$.
In one aspect, the TACA comprises $Le^y$.
In one aspect, the first solid substrate is nitrocellulose.
In one aspect, the carbohydrate is a glycan.
In one aspect, the carbohydrates are adhered to the substrate by a van der Waals interactions.
In one aspect, the carbohydrates are modified with a linker molecule.

In one aspect, the array comprises a linker with the general formula: G-A-Z—X (Formula 1), wherein: G is a glycan; A is a moiety comprising an ester or an amine; X is a substrate, which can include or exclude a surface, solid surface, transparent solid, non-transparent solid, a solid transparent to selected wavelengths of visible or non-visible light, a particle, an array, a microbubble, or a bead, coated substrate, coated surface, polymer surface, nitrocellulose-coated surface, or bead surface; a spacer group attached to the substrate or a spacer group with a group for adhering the linker to the substrate; and Z is a lipid chain or a spacer group with a lipid chain.

In one aspect, the novel G-A-Z—X arrays of this disclosure are used to detect one or more complexes between one or more immobilized carbohydrates and one or more carbohydrate binding moieties from the sample comprises binding to the complex one or more detectably labeled complex-binding agents. For example, where the carbohydrate binding moiety is an antibody, detectably labeled protein A or detectably labeled an anti-human antibody may be contacted with the one or more complexes. In some aspects, the detectable label comprises an enzyme, a fluorescent label, a chemiluminescent label, a nanoparticle label, or a synthetic, non-natural oligonucleotide. In some aspects the label may be detectable by, for example, surface-plasmon resonance (SPR), mobility shift assays or quantitative polymerase chain reaction (qPCR).

In one aspect, the method of using the novel G-A-Z—X arrays of this disclosure are used for detecting one or more complexes between one or more immobilized carbohydrates and one or more carbohydrate binding moieties from the sample comprises an ELISA assay. In some aspects the ELISA assay may use a secondary detectably labeled complex binding agent. For example, where the carbohydrate binding moiety is an antibody, enzyme linked protein A or an enzyme linked anti-human antibody may be contacted with the one or more complexes for ELISA detection of the complexes.

In some aspects, the carbohydrates comprise one or more of polysaccharides, or oligosaccharides, or carbohydrate portions of a glycol-conjugate, or SSEA-3 (or Gb5), SSEA-4, Globo H, Gb3, Gb4, $Le^y$, $Le^x$, $SLe^a$, or $SLe^x$.

In some aspects, detecting the complexes between the immobilized carbohydrates comprises: an enzyme reaction.

In one aspect, the enzyme reaction is performed on immobilized carbohydrates on the array surface, wherein the enzyme is capable of detecting the immobilized polysaccharides, or oligosaccharides, or carbohydrate portions of a glycoconjugate, or SSEA-3 (or Gb5), SSEA-4, Globo H, Gb3, Gb4, $Le^y$, $Le^x$, $SLe^a$, or $SLe^x$.

In one aspect, the carbohydrate binding moieties are proteins. In some aspects, the proteins which bind to the carbohydrates immobilized on the array are labeled with a detectable label.

In one aspect, the protein labels comprise chemiluminescence reporter molecule.

In some aspects, this invention relates to the disclosed novel array of carbohydrates immobilized on a substrate, for use in disease diagnosis, recurrence monitoring and drug discovery. In some aspects, the array is fabricated by a method comprising: (a) providing a substrate; (b) coating the substrate with nitrocellulose, (c) immobilizing a plurality of G-A-Z moieties at discrete locations on the surface of the substrate. In some aspects, this invention relates to a method of characterizing an array, comprising contacting the immobilized G-A-Z moieties with a labeled antibody to the TACA, forming complexes between the antibody and the glycan, and detecting the complexes. The labeled antibody can comprise a label comprising an enzyme, a fluorescent label, a chemiluminescent label, or a nanoparticle label. The antibody label can be an enzyme-linked label. The antibody can specifically recognize the immobilized polysaccharides, or oligosaccharides, or carbohydrate portions of a glycoconjugate, or SSEA-3, SSEA-4, or Globo H.

In one aspect, this disclosure relates to novel arrays of carbohydrates immobilized on a substrate for use in disease diagnosis, recurrence monitoring and drug discovery. In some aspects, the array is fabricated by a method comprising: (a) providing a substrate; (b) coating the substrate with nitrocellulose; and (c) immobilizing a plurality of carbohydrates at discrete locations on the substrate. In some aspects, the immobilized carbohydrates can be characterized, for example, by ELISA radioisotope labels, chemiluminescence, fluorescent labels, nanoparticles, surface-plasmon resonance (SPR), mobility shift assays or quantitative polymerase chain reaction (qPCR). Any of the substrates disclosed herein can be used in the array.

In some aspects, this disclosure relates to a bead for use in disease diagnosis, recurrence monitoring and drug discovery, and the bead comprising: (a) a unique identifier on or within each bead; and (b) a glycan attached to the surface of the bead through a linker moiety. The linker moiety can be any of the linkers disclosed herein.

In some aspects, this disclosure relates to methods of making glycan-linker-beads, comprising (a) providing a bead comprising a unique identifier on or within each bead; (b) contacting a glycan-linker with the bead; and (c) forming a conjugate between the glycan-linker and the bead. In some aspects, the conjugate is formed through formation of an ester or amide bond.

In some aspects, this disclosure relates to a plurality of beads for use in disease diagnosis, recurrence monitoring and drug discovery, wherein each bead has a unique identifier on or within each bead, wherein bead-n comprises a plurality of $G_1$-A-Z moieties, wherein $G_1$ is one TACA, and bead-n comprises a plurality of $G_n$-A-Z, wherein $G_n$ is a second TACA which is substantially the same as the $G_1$ TACA.

In one aspect, this disclosure relates to a compound of formula: G-A-Z—X (Formula 1) wherein: G is a glycan; A is a moiety comprising an ester or an amide; X is a substrate, for example, a surface, solid surface, transparent solid, non-transparent solid, a solid transparent to selected wavelengths of visible or non-visible light, a particle, an array, a microbubble, or a bead, coated substrate, coated surface, polymer surface, nitrocellulose-coated surface, or bead surface; a spacer group attached to the substrate or a spacer group with a group for adhering the linker to the substrate; and Z is one or a plurality of lipid chains, one or a plurality of a spacer group with lipid chains.

In one aspect, this disclosure features a compound having the following formula:

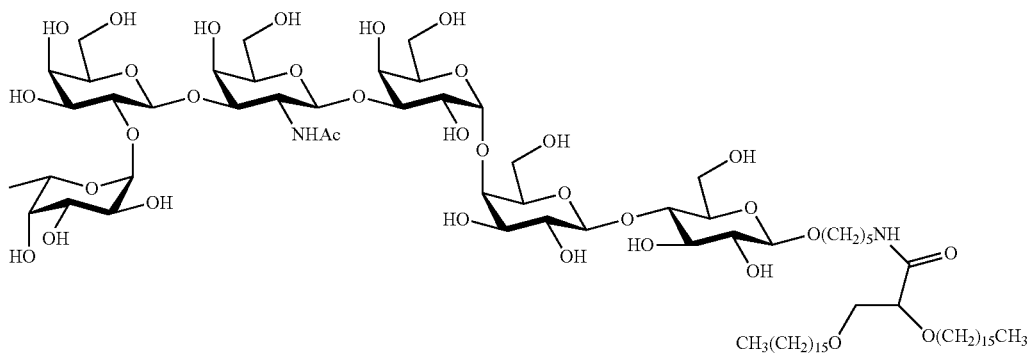

Formula 2

In one aspect, this disclosure features a compound having the following formula:

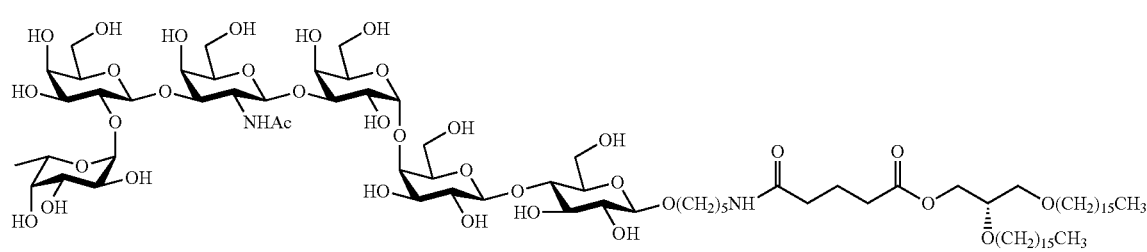

Formula 3

In one aspect, this disclosure features an exemplary G-A-Z compound having the following formula:

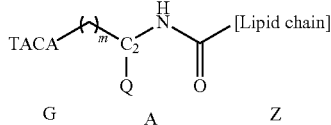

Formula 4

G   A   Z wherein Q may be

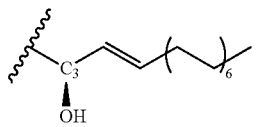

or hydrogen, $C_2$ may be chiral or non-chiral, $C_3$ has the chirality as shown, [Lipid chain] may be any $C_4$-$C_{16}$ linear or branched alkyl or alkoxy chain, m may have the integer value ranging from one to ten; wherein TACA is selected from one of the following: Globo H, SSEA-3 (or Gb5), SSEA-4, Gb3, Gb4, Le$^y$, Le$^x$, SLe$^a$, or SLe$^x$, and/or n-pentylamine-functionalized variants thereof. As indicated above, this formula is an exemplary G-A-Z.

In one aspect, an exemplary G-A-Z compound has the following formula:

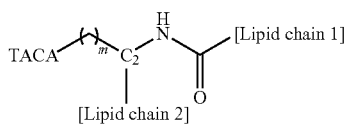

Formula 5 wherein $C_2$ may be chiral or non-chiral, $C_3$ has the chirality as shown, [Lipid chain 1] may be any $C_4$-$C_{16}$ linear or branched alkyl or alkoxy chain, [Lipid chain 2] may be hydrogen or any unsaturated $C_4$-$C_{16}$ alkyl chain comprising a least one hydroxy moiety, m may have the integer value ranging from one to ten; wherein TACA is selected from one of the following: Globo H, SSEA-3 (or Gb5), SSEA-4, Gb3, Gb4, Le$^y$, Le$^x$, SLe$^a$, or SLe$^x$, and/or n-pentylamine-functionalized variants thereof.

In one aspect, m may be five, [Lipid chain 1] may be the following formula:

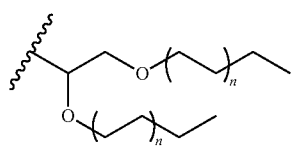

Formula 6 wherein n is an integer from one to ten, including seven, and the wavy line represents the bond to the carbonyl carbon connected to [Lipid chain 1].

In one aspect, a compound according to the following formula is provided:

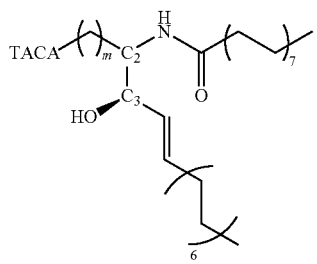

Formula 7 wherein $C_2$ may be chiral or non-chiral, $C_3$ has the chirality as shown, m may have the integer value ranging from one to ten, including one; wherein TACA is selected from one of the following: Globo H, SSEA-3 (or Gb5), SSEA-4, Gb3, Gb4, Le$^y$, Le$^x$, SLe$^a$, or SLe$^x$, and/or n-pentylamine-functionalized variants thereof.

In one aspect, a compound according to the following formula is provided:

Formula 8

TACA—[CH$_2$]$_m$—NH—C(=O)—[Lipid chain]

G   A   Z wherein [Lipid chain], also referred to herein as "Lipid", may be any $C_4$-$C_{16}$ linear or branched alkyl or alkoxy chain, m may have the integer value ranging from one to ten; wherein TACA is selected from one of the following: Globo H, SSEA-3 (or Gb5), SSEA-4, Gb3, Gb4, Le$^y$, Le$^x$, SLe$^a$, or SLe$^x$, and/or n-pentylamine-functionalized variants thereof.

In one aspect, a compound according to the following formula is provided:

Formula 9

TACA—HN—C(=O)—CR$_1$R$_2$—C(=O)—NH—CH$_2$—C$_1$(H)(O-[chain]$_n$)(O-[chain]$_n$)

wherein the chiral carbon atom $C_1$ is racemic or chiral;

wherein $R_1$ and $R_2$ can be alkyl, aryl, halo, heteroaryl, haloalkyl, benzyl, phenyl, and interlinked such that $R_1$ and $R_2$ can form a cyclic bond;

wherein n=an integer ranging from 4 to 9, including n=7; and wherein TACA is selected from one of Globo H, SSEA-3, Gb3, Gb4, SSEA-4, Le$^y$, SLe$^a$, and SLe$^x$, and/or n-pentylamine-functionalized variants thereof.

In one aspect a compound according to any one of the following formula is provided:

Formula 10

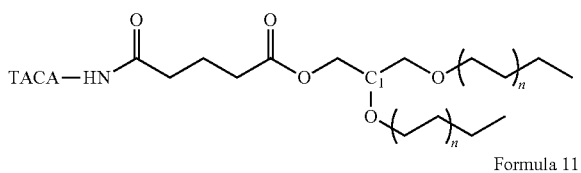

Formula 11

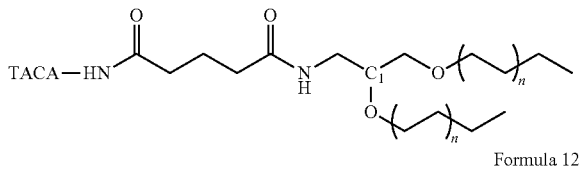

Formula 12

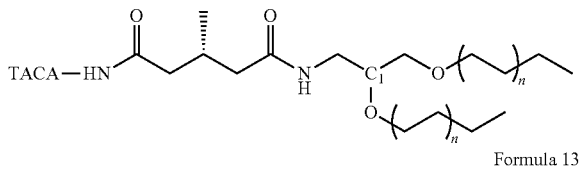

Formula 13

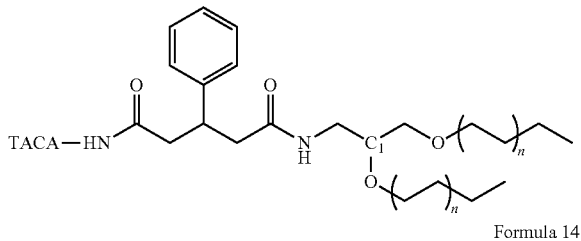

Formula 14

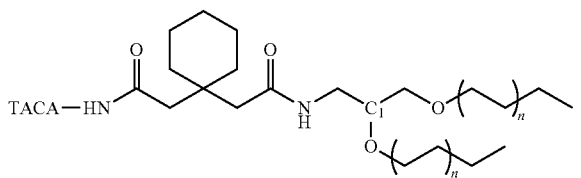

wherein the chiral carbon atom $C_1$ is racemic or chiral;
wherein n=an integer ranging from 4 to 9, including n=7; and
wherein TACA is selected from one of Globo H, SSEA-3 (or Gb5), Gb3, Gb4 SSEA-4, $Le^y$, $SLe^a$, or $SLe^x$, and/or n-pentylamine-functionalized variants thereof.

In one aspect, it is provided a method of preparing the compounds herein, wherein Lipid chain-1 or Lipid chain-2 is reacted with pentylamine-functionalized Globo H to form an amide bond.

In one aspect, a compound according to the following formula is provided:

Formula 15

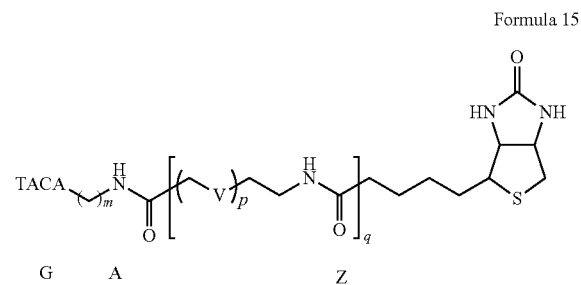

wherein m may have the integer value ranging from one to ten;
wherein V may be oxygen or carbon;
wherein q may have the integer value ranging from one to three;
wherein TACA is selected from one of the following: Globo H, SSEA-3 (or Gb5), SSEA-4, Gb3, Gb4, $Le^y$, $Le^x$, $SLe^a$, or $SLe^x$, and/or n-pentylamine-functionalized variants thereof.

In one aspect, provided is a method of improving the sensitivity in an array wherein the method comprises the use of the linkers disclosed herein.

In one aspect, this disclosure relates to a cancer diagnostic method, comprising (a) providing a sample containing antibodies from a subject suspected of having cancer; (b) contacting the sample with an array comprising one or more TACAs; (c) forming complexes of antibodies in the sample bound to one or more TACAs; (d) detecting the amount of antibodies bound to one or more TACAs; and (e) determining the disease state of the subject based on the amounts of said antibodies bound to said one or more TACAs compared to normal levels of antibodies bound to said one or more TACAs. In some aspects, the normal levels can be, for example, a reference value or range based on measurements of the levels of TACA bound antibodies in samples from normal patients or a population of normal patients. In some aspects, the TACA binding antibodies detected are circulating antibodies. In one aspect the detection comprises the determination of at least one antibody against at least one TACA. In some aspects, the TACAs on the array may be selected from one or more of Tn, TF, sTn, Polysialic acid, Globo H, SSEA-3, SSEA-4, Gb3, Gb4, $Le^x$, $Le^y$, $Le^a$, $sLe^x$, $SLe^x$, GD1a, GT1b, A2B5, GD2, GD3, GM1, GM2, GM3, fucosyl-GM1 or Neu5GcGM3.

In one aspect the sample is a body fluid (serum, saliva, lymph node fluid, urine, vaginal swab, or buccal swab).

In one aspect this disclosure relates to screening libraries of glycan binding partners for TACA binding partners. In some aspects the molecules or libraries may comprise, for example, antibodies, nanobodies, antibody fragments, aptamers, lectins, peptides, or combinatorial library molecules. In one aspect the screening of said libraries to identify said TACA binding partners comprises the use of a TACA glycan array, as disclosed herein.

In some aspects, the TACA binding partners may be used in various applications. For example, in one aspect, this disclosure relates to a method for determining the disease state of a subject in need thereof, the method comprising (a) providing a sample from a subject; (b) contacting the sample with one or more TACA binding partners; (c) measuring the specificity of binding between the TACA and the binding partner, and (d) detecting the level of tumor associated carbohydrate antigen (TACA) expressed.

The TACA binding partners may be used, for example, as a therapeutic to treat patients in need thereof, for example, patients that have a TACA expressing cancer, tumor, neoplasm, or hyperplasia.

In one aspect, the detection comprises the detection of a TACA. In one aspect the detection of said TACA comprises the use of a TACA glycan array.

In some aspects, the method comprises assaying a sample selected from one or more of sarcoma, skin cancer, leukemia, lymphoma, brain cancer, glioblastoma, lung cancer, breast cancer, oral cancer, head-and-neck cancer, nasopharyngeal cancer, esophagal cancer, stomach cancer, liver cancer, bile duct cancer, gallbladder cancer, bladder cancer, pancreatic cancer, intestinal cancer, colorectal cancer, kidney cancer, cervix cancer, endometrial cancer, ovarian cancer, testical cancer, buccal cancer, oropharyngeal cancer, laryngeal cancer and/or prostate cancer. In one aspect, the method comprises the assaying of a sample selected from one or more of breast, ovary, lung, pancreatic, stomach (gastric), colorectal, prostate, liver, cervix, esophagus, brain, oral, and/or kidney cancer. In some aspects, the method comprises detecting one or more of cancer, neoplasm, hyperplasia of breast, ovary, lung, pancreatic, stomach (gastric), colorectal, prostate, liver, cervix, bladder, esophagus, brain, oral, and/or kidney cancer.

In one aspect, the one or more of the disease states is characterized by B cell lymphoma, melanoma, neuroblastoma, sarcoma, non-small cell lung carcinoma (NSCLC).

In one aspect, the present disclosure relates to a method of using the novel arrays of this disclosure for determining the therapeutic efficacy of an antineoplastic agent in treatment of a subject in need thereof, the method comprising: (a) providing a sample form a subject; (b) contacting the sample with a TACA array (c) assaying the binding of one or more of TACAs or antibodies, and (d) determining the therapeutic effect of an antineoplastic agent in the treatment for neoplasm based on the assayed value of the glycan detection; is provided.

In one aspect, a method of using the novel arrays of this disclosure for determining the therapeutic efficacy of an antineoplastic agent during treatment of a subject in need thereof, comprising: (a) providing a sample form a subject prior to treatment; (b) contacting the sample with a TACA array; (c) assaying the titer of TACA binding moieties prior to treatment; (d) providing one or a plurality of samples from the subject following administration of the antineoplastic agent; (e) contacting the one or a plurality of samples with the TACAs array; (f) assaying the TACA titer in the one or a plurality of samples, and (g) determining the therapeutic effect of an antineoplastic agent in treatment for neoplasm based on the change in TACA titer. In some aspects the TACA binding moieties can be antibodies.

In one aspect, the antineoplastic agent comprises a vaccine. The vaccine may comprise a carbohydrate antigen or a carbohydrate immunogenic fragment conjugated to a carrier protein. In some aspects, the carbohydrate antigen or a carbohydrate immunogenic fragment may comprise Globo H, Stage-specific embryonic antigen 3 (SSEA-3), Stage-specific embryonic antigen 4 (SSEA-4), Tn, TF, sTn, Polysialic acid, Globo H, SSEA-3, SSEA-4, Gb3, Gb4, $Le^x$, $Le^y$, $Le^a$, $sLe^x$, $SLe^x$, GD1a, GT1b, A2B5, GD2, GD3, GM1, GM2, GM3, fucosyl-GM1 or Neu5GcGM3. In one aspect, the carrier protein comprises KLH (Keyhole limpet hemocyanin), DT-CRM 197 (diphtheria toxin cross-reacting material 197), diphtheria toxoid or tetanus toxoid. In one aspect, the vaccine is provided as a pharmaceutical composition. In one aspect, the pharmaceutical composition comprises Globo H-KLH and an additional adjuvant. In one aspect, the additional adjuvant is selected from saponin, Freund's adjuvant or α-galactosyl-ceramide (α-GalCer) adjuvant. In one aspect, the pharmaceutical composition comprises OBI-822/OBI-821, as described herein. In one aspect, the antineoplastic agent comprises an antibody or an antigen-binding portion thereof capable of binding one or more carbohydrate antigens.

In one aspect, the subject in need thereof is suspected of having one or more of cancer, carcinoma, neoplasm, or hyperplasia. In one aspect, the cancer is selected from the group consisting of: sarcoma, skin cancer, leukemia, lymphoma, brain cancer, glioblastoma, lung cancer, breast cancer, oral cancer, head-and-neck cancer, nasopharyngeal cancer, esophagal cancer, stomach cancer, liver cancer, bile duct cancer, gallbladder cancer, bladder cancer, pancreatic cancer, intestinal cancer, colorectal cancer, kidney cancer, cervix cancer, endometrial cancer, ovarian cancer, testical cancer, buccal cancer, oropharyngeal cancer, laryngeal cancer and prostate cancer.

The glycans used on the arrays of the invention may include two or more sugar units. The glycans of the invention may include straight chain and branched oligosaccharides as well as naturally occurring and synthetic glycans. It is contemplated that any type of sugar unit may be present in the glycans of the invention, including allose, altrose, arabinose, glucose, galactose, gulose, fucose, fructose, idose, lyxose, mannose, ribose, talose, xylose, neuraminic acid or other sugar units. Such sugar units may have a variety of substituents. For example, substituents that may be present instead of, or in addition to, the substituents typically present on the sugar units include amino, carboxy including ionic carboxy and salts thereof (e.g., sodium carboxylate), thiol, azide, N-acetyl, N-acetylneuraminic acid, oxy (=O), sialic acid, sulfate ($-SO_4-$) including ionic sulfate and salts thereof, phosphate ($-PO_4-$), including ionic phosphate and salts thereof, lower alkoxy, lower alkanoyloxy, lower acyl, and/or lower alkanoylaminoalkyl. Fatty acids, lipids, amino acids, peptides and proteins may also be attached to the glycans of the invention. In some aspects, the glycans can include or exclude: Globo H, SSEA-3, SSEA-4, $Le^y$, $SLe^a$, $SLe^x$, or any combination thereof. In some aspects, the glycans include or exclude n-pentylamine-functionalized variants of Globo H, SSEA-3, SSEA-4, $Le^y$, $SLe^a$, $SLe^x$ or any combination of functionalized glycan variants and/or non-functionalized glycans.

In another aspect, the invention provides a microarray that includes a solid substrate and a multitude of defined glycan locations on the solid support, each glycan location defining a region of the solid support comprising multiple copies of one type of glycan molecule attached thereto, wherein the glycans are attached to the microarray by a linker, as described herein. These microarrays may have, for example, between about 1 to about 100,000 different glycan locations, or between about 1 to about 10,000 different glycan locations, or between about 2 to about 100 different glycan locations, or between about 2 to about 5 different glycan locations. In some aspects, the glycans attached to the array are referred to as glycan probes.

In another aspect, the invention provides a method of identifying whether a test molecule or test substance can bind to a glycan present on an array or microarray of the invention. The method involves contacting the array with the test molecule or test substance and observing whether the test molecule or test substance binds to the glycan in a glycan library, or on the array. In some aspects, this disclosure relates to test molecules or test substances in a library, as described herein.

In another aspect, the invention provides a method of identifying to which glycan a test molecule or test substance can bind, wherein the glycan is present on an array of the invention. The method involves contacting the array with the test molecule or test substance and observing to which glycan the array the test molecule or test substance can bind.

The density of glycans at each glycan location may be modulated by varying the concentration of the glycan solution applied to the derivatized glycan location.

Another aspect of the invention related to an array of molecules which may comprise a library of molecules attached to an array through a linker molecule, wherein the cleavable linker has the following structure:

$$G-A-Z-X \qquad \text{Formula 1}$$

wherein G is a glycan; A is a moiety comprising an ester or an amide; X is a substrate, for example, a surface, solid surface, transparent solid, non-transparent solid, a solid transparent to selected wavelengths of visible or non-visible light, a particle, an array, a microbubble, or a bead, coated substrate, coated surface, polymer surface, nitrocellulose-coated surface, or bead surface; a spacer group attached to the substrate or a spacer group with a group for adhering the linker to the substrate; and Z is one or a plurality of linkers, wherein said linkers may comprise lipid chains, one or a plurality of a spacer group with lipid chains.

In some aspects, the array includes a substrate and a multitude of defined glycan probe locations on the solid support, each glycan probe location defining a region of the solid support that has multiple copies of one type of similar glycan molecules attached thereto.

The interaction between A and X may, in some aspects, be a covalent bond, Van der Waals interaction, hydrogen bond, ionic bond, or hydrophobic interactions.

Another aspect of the invention is a method of testing whether a molecule in a test sample can bind to the array of molecules which may comprise (a) contacting the array with the test sample and (b) observing whether a molecule in the test sample binds to a molecule attached to the array.

Another aspect of the invention is a method of determining which molecular structures bind to biomolecule in a test sample which may comprise contacting an array of molecules with a test sample, washing the array and cleaving the cleavable linker to permit structural or functional analysis of molecular structures of the molecules attached to an array. For example, the biomolecule can be an antibody, a receptor or a protein complex.

Another aspect of the invention is a method of detecting cancer, including breast cancer, in a test sample which may comprise (a) contacting a test sample with linkers covalently attached to glycans comprising Globo H, SSEA-3, SSEA-4, Le$^y$, SLe$^a$, and SLe$^x$; (b) determining whether antibodies in the test sample bind to molecules/determinants associated with Globo H, SSEA-3, SSEA-4, Le$^y$, SLe$^a$, and SLe$^x$.

wherein the chiral carbon atom e.g. C1 is racemic or chiral; n is an integer ranging from 5 to 9, including n=7; and TACA is selected from one of Globo H, SSEA-3 (or Gb5), SSEA-4, Gb3, Gb4, Le$^y$, Le$^x$, SLe$^a$, or SLe$^x$.

In one aspect, this disclosure features a compound having the following formula:

Formula 16

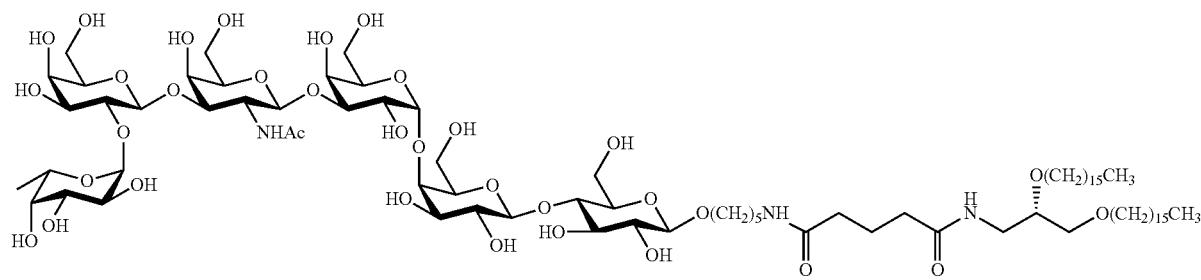

Formula 17

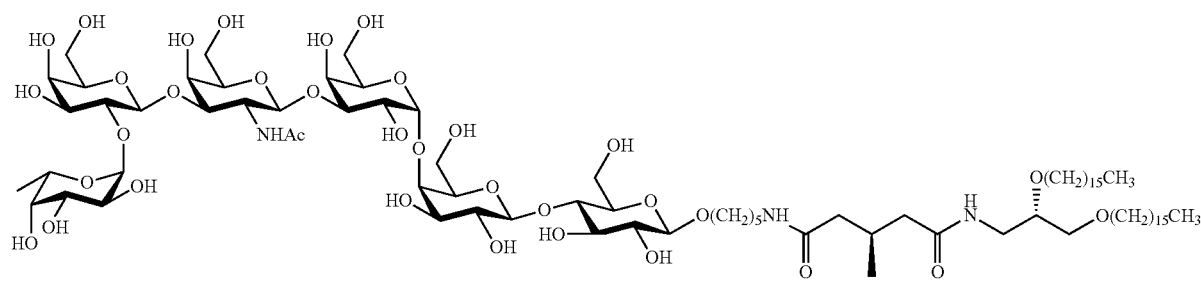

Formula 18

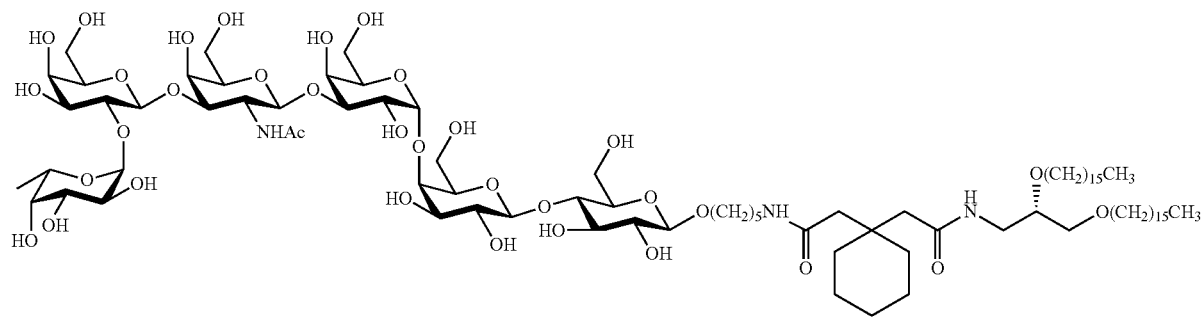

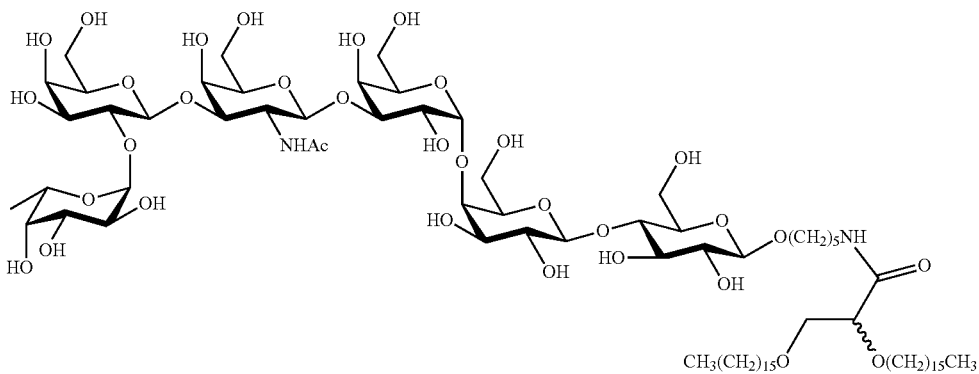

Formula 19

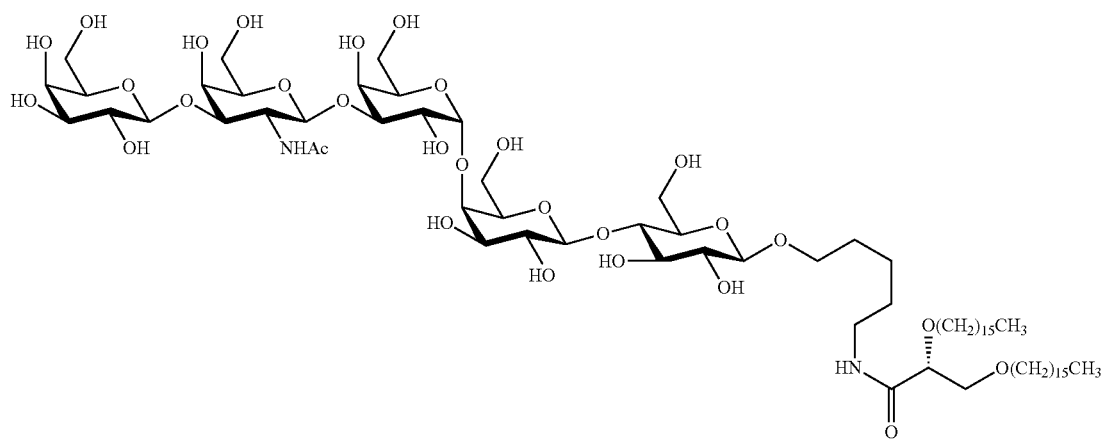

Formula 20

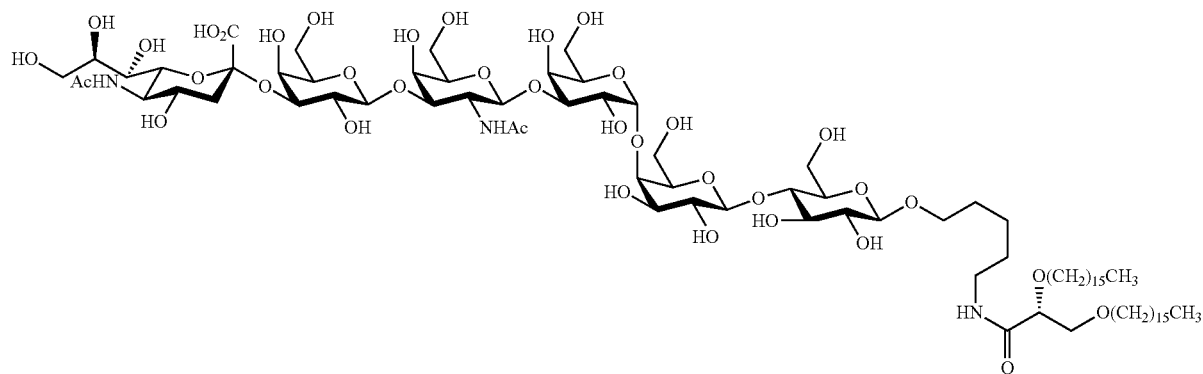

Formula 21

BRIEF DESCRIPTION OF THE FIGURES

FIG. 4A showed the synthesis of Globo H-lipid 1 (Formula 2). FIG. 4B showed the synthesis of Globo H-lipid 2 (Formula 3). FIG. 4C showed the synthesis of Globo H-lipid 3 (Formula 16). FIG. 4D showed the synthesis of Globo H-lipid 4 (Formula 17). FIG. 4E showed the synthesis of Globo H-lipid 6 (Formula 18). FIG. 4F showed the synthesis of Globo H-lipid 1 (racemic) (Formula 19).

FIG. 5A showed the mass spectrum of Globo H-lipid 1. FIG. 5B showed the mass spectrum of Globo H-lipid 2. FIG. 5C showed the mass spectrum of Globo H-lipid 3. FIG. 5D showed the mass spectrum of Globo H-lipid 4. FIG. 5E showed the mass spectrum of Globo H-lipid 6. FIG. 5F showed the mass spectrum of Globo H-lipid 1 (racemic).

FIG. 6A showed the synthesis process of SSEA-3-lipid 1 (Formula 20). FIG. 6B showed the mass spectrum of SSEA-3-lipid 1.

FIG. 7A showed the synthesis process of SSEA-4-lipid 1(Formula 21). FIG. 7B showed the mass spectrum of SSEA-4-lipid 1.

FIG. 8A showed the ELISA binding patterns of Globo H-ceramide and Globo H-lipids. FIG. 8B showed the comparison of Globo H-ceramide, Globo H-lipid 1, and Globo H-lipid 2 binding efficiency in the detection of pancreatic cancer.

FIG. 10A illustrated the binding pattern of Globo H-ceramide IgM. FIG. 10B illustrated the binding pattern of Globo H-lipid 1 IgM. FIG. 10C illustrated the binding pattern of SSEA-3-ceramide IgM. FIG. 10D illustrated the binding pattern of Globo H-lipid 1 IgG. FIG. 10E illustrated the binding pattern of SSEA-4-lipid 1 IgG.

FIG. 11A illustrated the binding pattern of Globo H-lipid 1. FIG. 11B illustrated the binding pattern of SSEA-4-lipid 1. FIG. 11C illustrated the categorized pancreatic cancer stages of Globo H-lipid 1. FIG. 11D illustrated the categorized pancreatic cancer stages of SSEA-4-lipid 1.

FIG. 12A illustrated the binding pattern of Globo H-lipid 1. FIG. 12B illustrated the binding pattern of SSEA-3-lipid 1. FIG. 12C illustrated the binding pattern of SSEA-4-lipid 1. FIG. 12D illustrated the categorized lung cancer stages of Globo H-lipid 1. FIG. 12E illustrated the categorized lung cancer stages of SSEA-3-lipid 1. FIG. 12F illustrated the categorized lung cancer stages of SSEA-4-lipid 1

DETAILED DESCRIPTION

Figure 1:
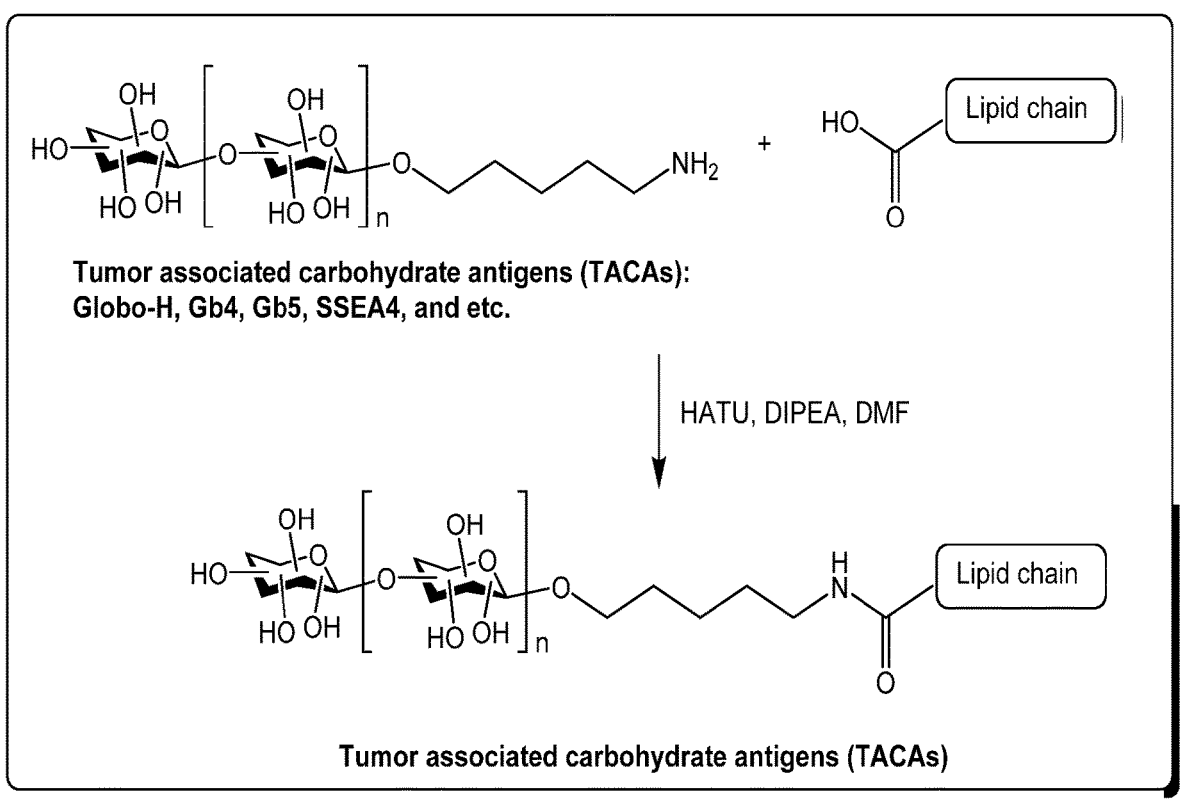
FIG. 1. The reaction scheme for formation of glycan-linked glycopeptides.
Figure 2:
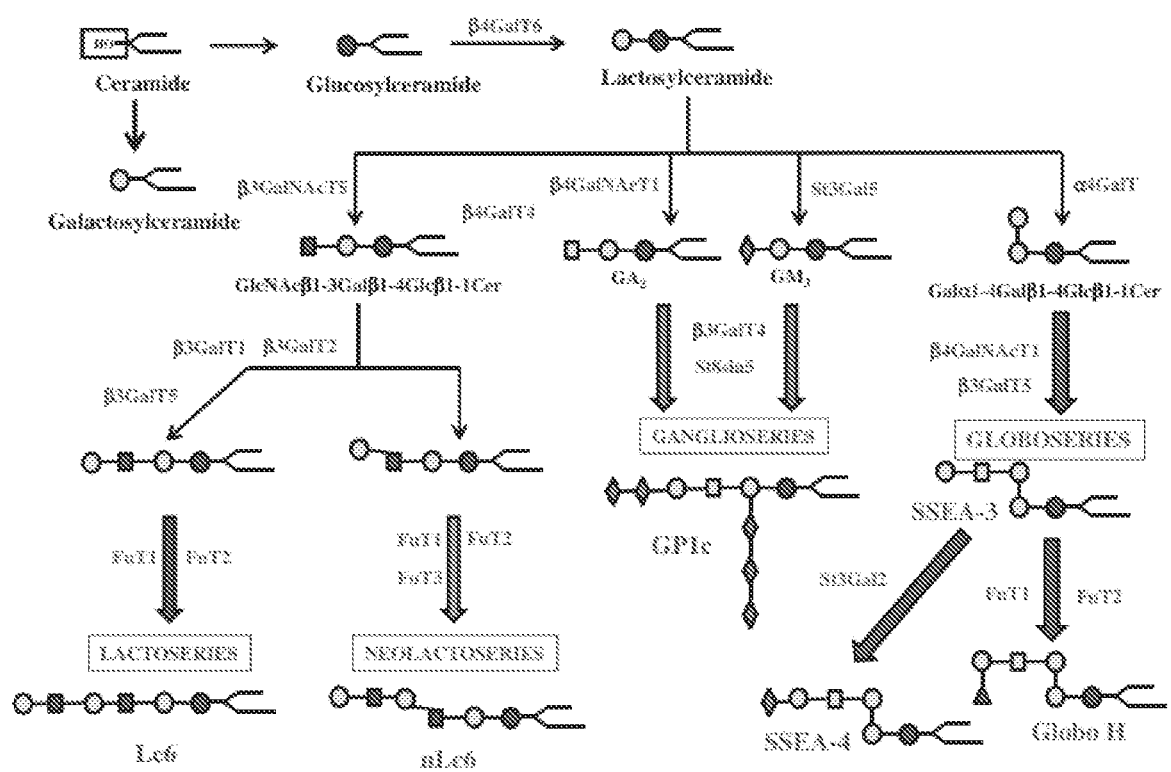
FIG. 2. The biosynthetic pathway of Glycosphingolipids.

The present disclosure provides libraries and arrays of glycans that can be used for identifying which types of proteins, receptors, antibodies, lipids, nucleic acids, carbohydrates and other molecules and substances can bind to a given glycan structure.

The inventive libraries, molecules, arrays and methods have several advantages. One particular advantage of the arrays of the invention is that the glycans on the arrays are attached by a linker to a substrate such as a polymeric substrate. For example, the linkers of the invention can have a peptide bond that is linked to long alkyl chains stable for the types of binding interactions with polymeric surfaces. However, the linker can be detached via the disruption of van der Waals interactions (for example, with a surfactant) if one of skill in the art chooses so that the linker with the attached glycan can be further analyzed or utilized for other purposes.

The arrays and methods of the invention also provide highly accurate results. The libraries and arrays of the invention provide large numbers and varieties of glycans. As a non-limiting example, the libraries and arrays of the invention have at least one, at least two, at least three, at least ten, or at least 100 glycans. In some embodiments, the libraries and arrays of the invention have about 1 to about 100,000, or about 1 to about 10,000, or about 1 to about 1,000, or about 1 to about 100, or about 2 to about 100, or about 2 to about 10, or about 1 to about 10 different glycans per array. Such large numbers of glycans permit the simultaneous assay of a multitude of glycan types. As described herein, the present arrays have been used for successfully screening a variety of glycan binding proteins. The composition of glycans on the arrays of the invention can be varied as appropriate. Many different glycoconjugates can be incorporated into the arrays of the invention including, for example, naturally occurring or synthetic glycans, glycoproteins, glycopeptides, glycolipids, bacterial and plant cell wall glycans and the like.

Immobilization procedures for attaching different glycans to the arrays of the invention are readily controlled to easily permit array construction. In some embodiments, each glycan can be adhered to a specific bead type, so as to form a glycan-specific association with that bead type. In some embodiments, the bead can further comprise a distinct marker which distinguishes that particular bead type from other bead types. In some embodiments, a plurality of different glycans, each adhered to a distinct bead type can be mixed in a multiplex reaction.

Arrays comprising unique libraries of different glycans adhered to defined regions on the solid support of an array surface can be adhered by any available procedure. In general, arrays are made by obtaining a library of glycan-linked glycopeptide molecules described herein, obtaining a substrate that has a surface modified to react with the specific linking moieties present on the glycan-linked glycopeptide molecules of the library and attaching the glycan molecules to the solid support by forming a van der Waals interaction between the linking moieties of the glycan-linked glycopeptide molecules and the modified surface of the substrate.

The modification reagent can be attached to the substrate via carbon-carbon bonds using, as a non-limiting example, siloxane bonds (using, for example, glass or silicon oxide as the solid substrate). In some embodiments, siloxane bonds with the surface of the substrate are formed in via reactions of derivatization reagents bearing mono-, di-, or tri-chlorosilyl, or mono-, di-, or tri-alkoxysilyl groups. The non-leaving (chloro- or alkoxy-) groups on the silane can be hydrocarbons. In some embodiments, the non-leaving groups can be linear or branched alkyl chains so as to form van der Waals interactions with the peptide chains of the glycan-linked glycopeptide.

The modification reagent can be applied to the substrate via other deposition methods known to those skilled in the art for applying coatings. Such methods include chemical vapor deposition, solution-phase deposition, Langmuir-Blodgett film formation, chemical plasma treatment to expose a reactive surface molecule, spin-coating, spray-drying, or electrospinning. In some embodiments, the modification reagent can be a polymer. The polymer can be selected from polystyrene, polypropylene, polyethylene, polyethylimine, polycaprolactine, modified polycaprolactone, polymethyl methacrylate, polyacrylamide, poly-N,N-alkyl acrylamide, polyalkyl methacrylate, polyalkyl acrylate, or a polysaccharide. The polysaccharide can be cellulose, nitrocellulose, chitosan, amylose, cellulose acetate, xanthan gum, dextran, welan gum, guar gum, gellan gum, diutan gum or pullulan.

Each type of glycan is contacted or printed onto to the solid support at a defined glycan probe location. A microarray gene printer can be used for applying the various glycan-linked glycopeptide to defined glycan probe locations. For example, about 0.1 nL to about 10 nL, or about 0.5 nL of glycan solution can be applied per defined glycan probe location. Various concentrations of the glycan-linked glycopeptide solutions can be contacted or printed onto the solid support. For example, a glycan-linked glycopeptide solution of about 0.1 to about 1000 μM glycan-linked glycopeptide or about 1.0 to about 500 μM glycan-linked glycopeptide or about 10 to about 100 μM glycan-linked glycopeptide can be employed. In general, it may be advisable to apply each concentration to a replicate of several (for example, three to six) defined glycan probe locations. Such replicates provide internal controls that confirm whether or not a binding reaction between a glycan-linked glycopeptide and a test molecule is a real binding interaction.

The carbohydrate tumor antigens Globo H, SSEA-3, SSEA-4, Le$^y$, SLe$^x$, and SLe$^x$ are poor biomarkers for cancer diagnostics because carbohydrates have very weak binding strength to proteins or antibodies in biological fluid. The Inventors have appreciated that the limitation of the weak carbohydrate binding antigens hinders the ability to use such carbohydrate tumor antigens for biomarker validation in cancer diagnosis.

Arrays of detector molecules are useful for detecting the presence of multiple analytes in a sample in parallel. The elements of an array of detector molecules comprises a substrate, the presentation of a coating of a bio-active molecule on the substrate, the presentation of one or a plurality of analytes to the coated substrate, the formation of a complex between the analyte and the bio-active molecule on the substrate, and a mechanism of detection. As used herein the term "bio-active molecule" means its ordinary meaning in the art and any molecule which exists or mimics a molecule known in biology or chemistry and which is capable of binding to another molecule via electrostatic, van der Waals interactions, hydrophobic interactions, covalent bonds, or hydrogen bonds.

The substrate of the current invention can be a surface. The surface can be flat, featured, round, curved, rough, porous, solid, gelatinous, polymeric, oligomeric, or a bead. The substrate can be composed of glass, polymer, or plastic. The bead can be round, cylindrical, egg-shaped, oval, approximately round, disc-shaped, square-shaped, hexagonal-shaped, or any polyhedral-shaped entity. In some embodiments, the substrate can be chemically modified so as to present a reactive group at the surface capable of binding to another molecule. In some embodiments, the reactive group can be a carboxylic acid.

In some embodiments, the substrate can be coated with a material which can present a reactive group at the surface capable of binding to another molecule. In some embodiments, the material coating the substrate is a nitrocellulose membrane or a polymer. Such coatings present a 3D surface with high surface area, enabling a lower limit of detection compared to flat surfaces. In some embodiments, a chemical linker can be presented to the surface, either directly to the surface or to a coating previously presented to the surface.

In some embodiments, the linker can comprise one of the following selected glycan-linked glycopeptide structures (GH is used sometimes herein to refer to TACA):

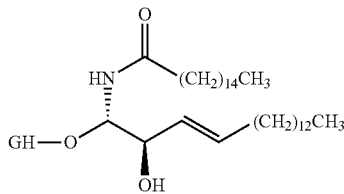

Formula 22

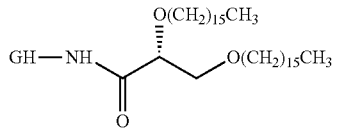

Formula 23

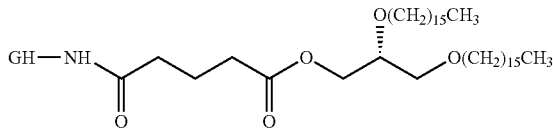

Formula 24

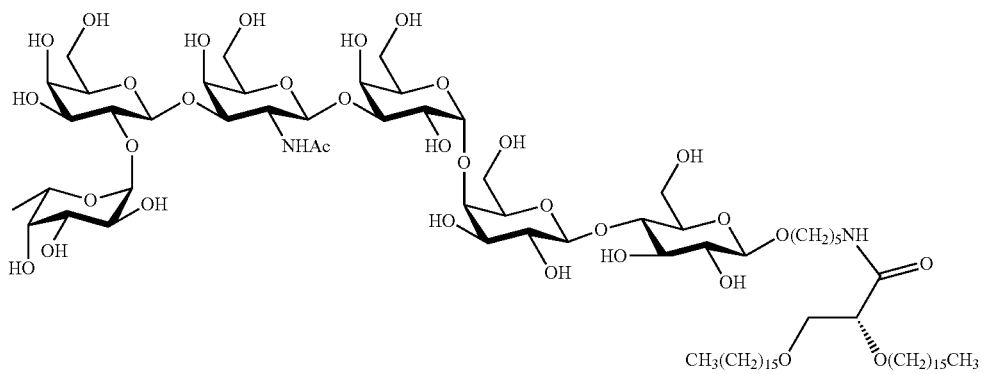

Formula 2

-continued
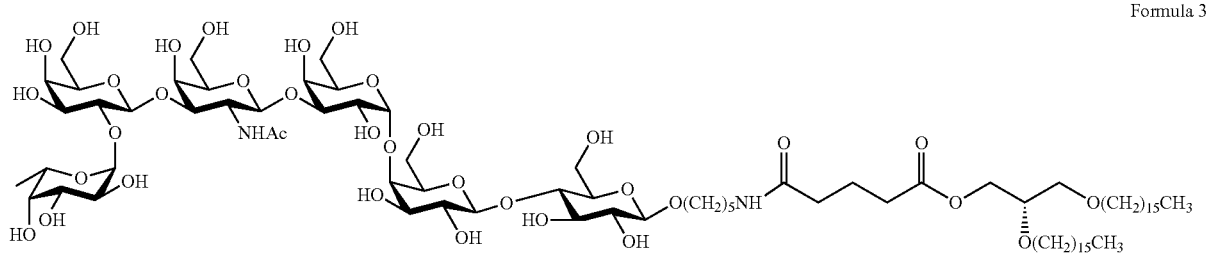
Formula 11
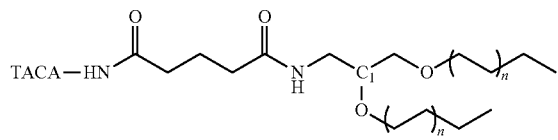
Formula 13
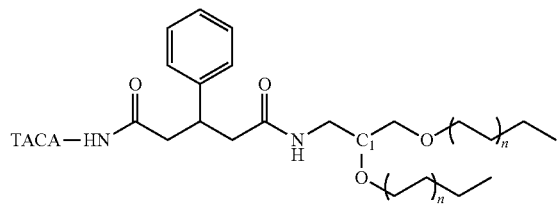
Formula 15
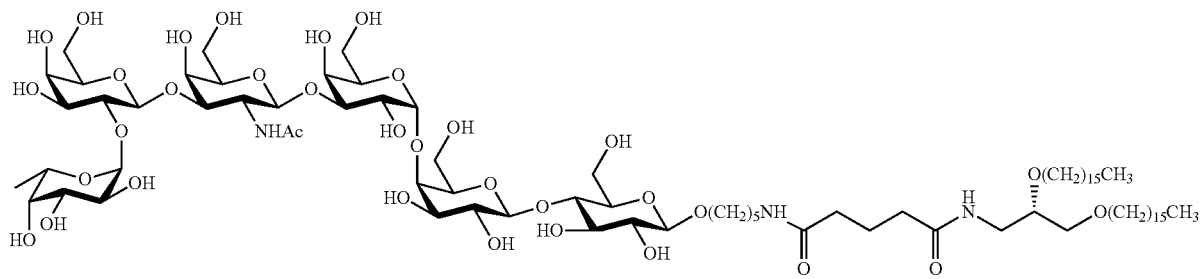
Formula 17
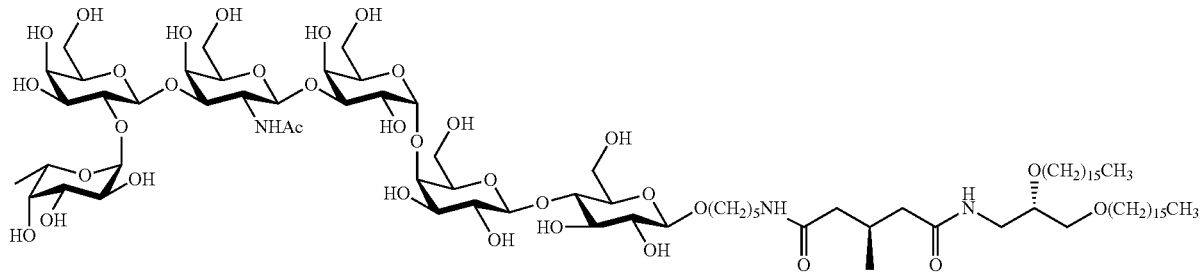
Formula 18
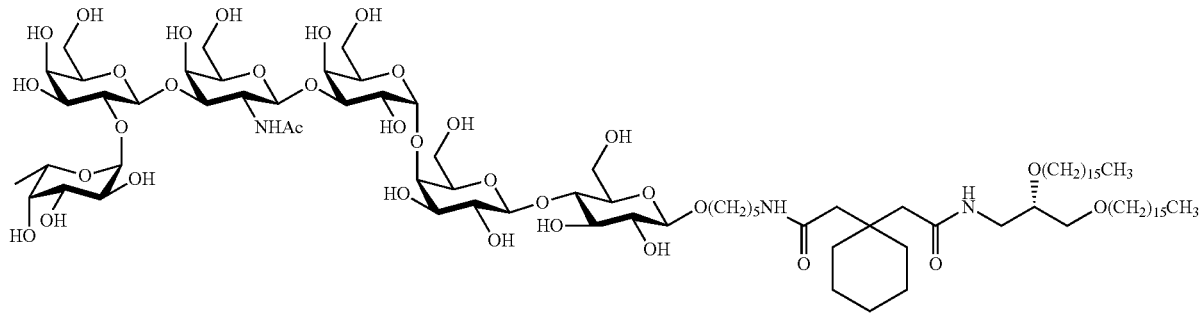
Formula 12
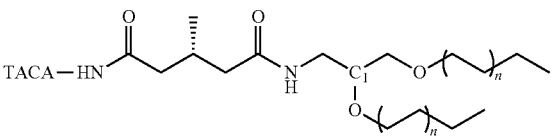
Formula 14
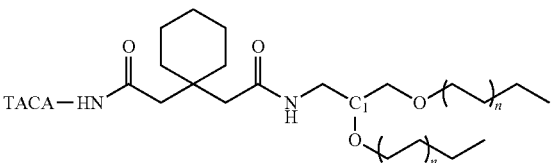
Formula 16

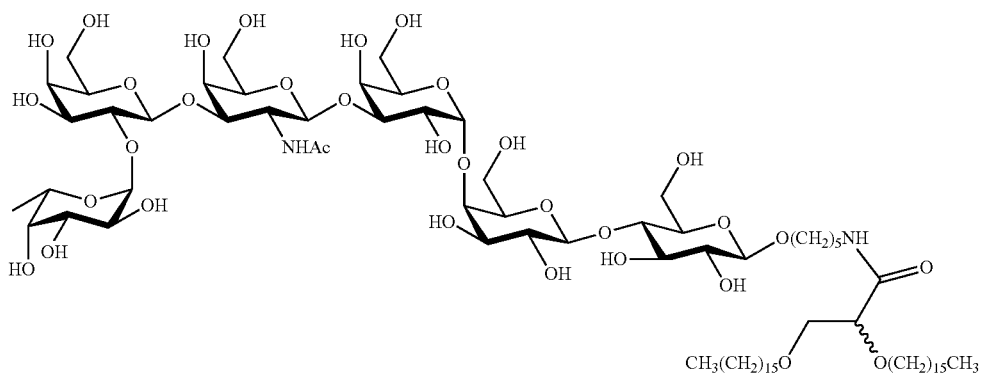

Formula 19

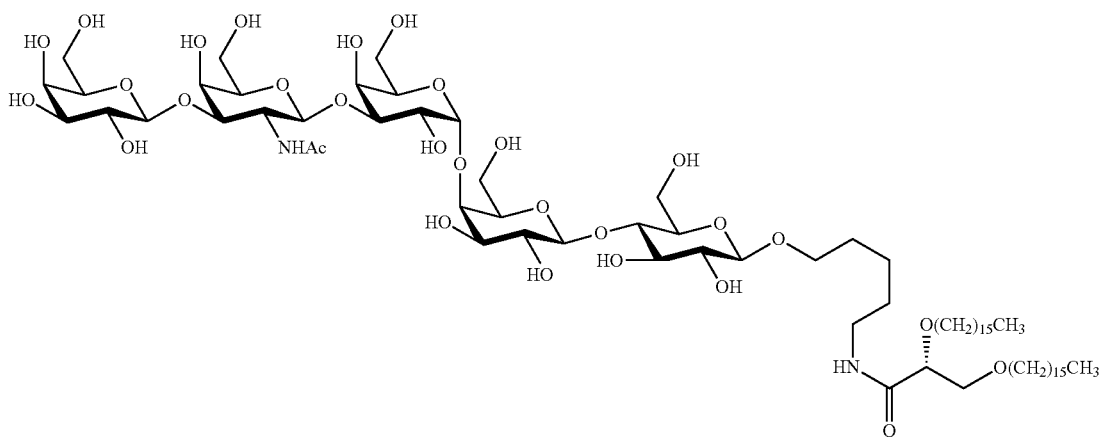

Formula 20

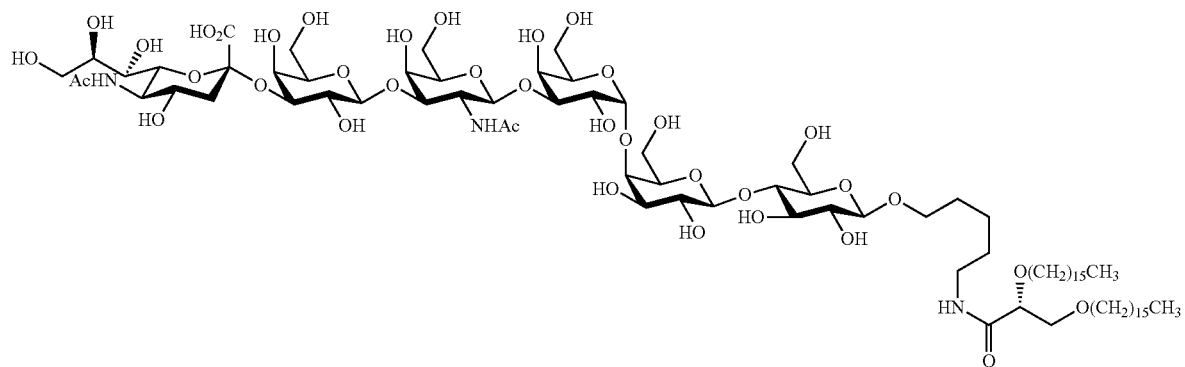

Formula 21 wherein the chiral carbon C1 can be racemic or chiral; n=5, 6, 7, 8, or 9; and TACA is selected from one of the following glycans: Globo H, SSEA-3 (or Gb5), SSEA-4, Gb3, Gb4, Le$^y$, Le$^x$, SLe$^a$, or SLe$^x$.

The glycan-linked glycopeptides can be synthesized by the formation of an amide or ester bond between the hexylamino-functionalized (for amides) or hexylhydroxyl-functionated (for esters) glycan and the lipid chain carboxylic acid, per the reaction scheme in FIG. 1. The glycans (tumor associated carbohydrate antigens (TACAs) can be reacted with the lipid chain carboxylic acids via any amide or ester formation methods. In some embodiments, the amide formation can occur via any standard peptide coupling method known to those skilled in the art. In some embodiments, the amide formation can occur via additives, coupling via carbodiimides, triazoles, Carbonyldiimidazole Derivatives, Phosphonium/Uronium/Formamidinium derivatives, or dehydration.

In some embodiments, the carbodiimides can be EDC (1-Ethyl-3-[3-dimethylaminopropyl]carbodiimide hydrochloride), DCC (N,N'-dicyclohexylcarbodiimide), 1-tert-Butyl-3-ethylcarbodiimide, 1,3-Di-p-tolylcarbodiimide, and DIC (N,N'-Diisopropylcarbodiimide).

In some embodiments, dehydration can be accomplished by the acid-catalyzed coupling in an organic solvent, optionally with the addition of 2,2-dimethoxypropane. In some embodiments, dehydration can be accomplished by 5-methoxy-2-iodophenylboronic acid catalysis. In some embodiments, the amide formation can be accomplished by adding to the amine and carboxylic acid reaction mixture one or more of the following reagents: 4-(4,6-Dimethoxy- 1,3,5-triazin-2-yl)-4-methylmorpholinium chloride, 1,3-Dimethyl-3,4,5,6-tetrahydro-2(1H)-pyrimidinone, 2-Ethoxy-1-ethoxycarbonyl-1,2-dihydroquinoline, 2-Fluoro-1-methylpyridinium p-toluenesulfonate, 2-hydroxy-1-methylpyridinium p-toluenesulfonate, 3-Hydroxy-1,2,3-benzotriazin-4(3H)-one solution, Isobutyl 1,2-dihydro-2-isobutoxy-1-quinolinecarboxylate, 1-(2-Mesitylenesulfonyl)-3-nitro-1H-1,2,4-triazole, 3-Methyl-1-phenyl-2-pyrazoline-5-one, 3-Nitro-1H-1,2,4-triazolide sulfonyl resin, PyOxim, or Woodward's reagent K, Acrylic acid N-hydroxysuccinimide ester, Bis(4-nitrophenyl) carbonate, Bis(pentafluorophenyl) carbonate, 2-Bromo-1-ethyl-pyridinium tetrafluoroborate, N-Bromosuccinimide, N,N'-Disuccinimidyl carbonate, N,N'-Disuccinimidyl carbonate, Di(N-succinimidyl) oxalate, N,N'-Di succinimidyl oxalate, Ethyl (hydroxyimino)cyanoacetate, 1-Hydroxybenzotriazole hydrate, N-Hydroxymaleimide, N-Hydroxy-5-norbornene-2,3-dicarboxylic acid imide, 3-(4-Hydroxyphenyl)propionic acid N-hydroxysuccinimide ester, N-Hydroxyphthalimide, N-Hydroxysuccinimide, N-Hydroxysuccinimidyl acetoacetate, N-Hydroxysulfosuccinimide sodium salt, Iodoacetic acid N-hydroxysuccinimide ester, 4-Nitrophenyl trifluoroacetate, K-Oxyma, Pentafluorophenol, Pentafluorophenyl trifluoroacetate, Phenoxyacetic acid N-hydroxysuccinimide ester, N-Succinimidyl N-methylcarbamate, 1,1'-Oxalyldiimidazole, and 1,1'-Carbonyl-di-(1,2,4-triazole).

In some embodiments, the amide formation can be accomplished by adding to the amine and carboxylic acid reaction mixture one or more of the following Phosphonium/Uronium/Formamidinium derivatives: 1-hydroxy-benzotriazole (HOBt), 1-hydroxy-7-aza-benzotriazole (HOAt), HBTU (N,N,N',N'-Tetramethyl-O-(1H-benzotriazol-1-yl) uronium hexafluorophosphate), (Benzotriazol-1-yloxy) tripyrrolidinophosphonium hexafluorophosphate (PyBOP), (7-Azabenzotriazol-1-yloxy)tripyrrolidinophosphonium hexafluorophosphate, O-Benzotriazol-1-yl-N,N,N',N'-bis(pentamethylene)uronium hexafluorophosphate, O-(Benzotriazol-1-yl)-N,N,N',N'-bis(tetramethylene)uronium hexafluorophosphate, (Benzotriazol-1-yloxy)dipiperidinocarbenium hexafluorophosphate, (Benzotriazol-1-yloxy) tripyrrolidinophosphonium hexafluorophosphate, (Benzotriazol-1-yloxy)tripyrrolidinophosphonium hexafluorophosphate, (Benzotriazol-1-yloxy)tris(dimethylamino)phosphonium hexafluorophosphate, O-(Benzotriazol-1-yl)-N,N,N,N'-tetramethyluronium tetrafluoroborate, Bromotripyrrolidinophosphonium hexafluorophosphate, Bromotris(dimethylamino)phosphonium hexafluorophosphate, O-(6-Chlorobenzotriazol-1-yl)-N,N,N,N'-tetramethyluronium tetrafluoroborate, O-(6-Chlorobenzotriazol-1-yl)-N,N,N',N'-tetramethyluronium hexafluorophosphate, 2-Chloro-1,3-dimethylimidazolidinium hexafluorophosphate, 2-Chloro-1,3-dimethylimidazolidinium tetrafluoroborate, 2-Chloro-1,3-dimethylimidazolinium chloride, Chlorodipyrrolidinocarbenium hexafluorophosphate, Chloro-N,N,N',N'-tetramethylformamidinium hexafluorophosphate, Chlorotripyrrolidinophosphonium hexafluorophosphate, 1-Cyano-2-ethoxy-2-oxoethylidenaminooxy)dimethylamino-morpholino-carbenium hexafluorophosphate (COMU), Dipyrrolidino(N-succinimidyloxy)carbenium hexafluorophosphate, O-[(Ethoxycarbonyl)cyanomethylenamino]-N,N,N,N'-tetramethyluronium hexafluorophosphate, O-[(Ethoxycarbonyl)cyanomethylenamino]-N,N,N,N'-tetramethyluronium tetrafluoroborate, Fluoro-N,N,N',N'-bis(tetramethylene)formamidinium hexafluorophosphate, Fluoro-N,N,N',N'-tetramethylformamidinium hexafluorophosphate, 1-[Bis(dimethylamino)methylene]-1H-1,2,3-triazolo[4,5-b]pyridinium 3-oxidhexafluorophosphate (HATU), N,N,N',N'-Tetramethyl-O-(1H-benzotriazol-1-yl) uronium hexafluorophosphate (HBTU) 1-[(Dimethylamino)(morpholino)methylene]-1H-[1,2,3]triazolo[4,5-b]pyridine-1-ium 3-oxide hexafluorophosphate (HDMA), O-(5-Norbornene-2,3-dicarboximido)-N,N,N',N'-tetramethyluronium tetrafluoroborate, S-(1-Oxido-2-pyridyl)-N,N,N',N'-tetramethylthiuronium hexafluorophosphate S-(1-Oxido-2-pyridyl)-N,N,N',N'-tetramethylthiuronium tetrafluoroborate, O-(2-Oxo-1(2H) pyridyl)-N,N,N,N'-tetramethyluronium tetrafluoroborate, O-(2-Oxo-1 (2H)pyridyl)-N,N,N',N'-tetramethyluronium tetrafluoroborate, N,N,N',N'-Tetramethyl-O—(N-succinimidyl)uronium hexafluorophosphate, and N,N,N',N'-Tetramethyl-O—(N-succinimidyl)uronium tetrafluoroborate.

Useful glycans of the invention include tumor-associated carbohydrate antigens (TACAs). The cell-surface glycosphingolipid Globo H is a member of a family of antigenic carbohydrates that are highly expressed on a range of cancer cell lines. Other Globo H glycosphingolipid analogues useful in the present invention can be SSEA-3 (or Gb5), SSEA-4, Gb3 or Gb4. Other glycans of the invention include Tn, TF, sTn, Polysialic acid, $Le^x$, $Le^y$, $Le^a$, $sLe^x$, $SLe^x$, GD1a, GT1b, A2B5, GD2, GD3, GM1, GM2, GM3, fucosyl-GM1 or Neu5GcGM3.

The glycans of the invention have been obtained by a variety of procedures. The synthesis of Globo H, SSEA-3 and SSEA-4 can be accomplished by methods known in the art (Bosse F. et al., *J Org Chem.* 67(19):6659-70, 2002; Koeller, K. M. and Wong, C.-H., *Nature,* 409, 232-240, 2001; Wymer, N. and Toone, E. J., *Curr. Opin. Chem. Biol.,* 4, 110-119, 2000; Gijsen, H. J. M.; Qiao, L.; Fitz, W. and Wong, C.-H., *Chem. Rev.,* 96, 443-473, 1996).

A moiety comprising an ester or an amine, A, can be a chemical linkage of an ester (—O—(C═O)—R) or an amide (—NH—(C═O)—R), where R is a linear or branched alkyl group, heteroalkyl group, aryl group, or heteroaryl group.

The substrate X can be the substrates and surfaces described above.

The lipid chain Z can be a linear or branched lipid chain. The chains can be saturated or unsaturated. The alkyl chains can comprise from twelve to forty carbons. In some embodiments, the chains are branched saturated alkyl chains. In some embodiments, the lipid chains can be ceramide chains.

Detection of binding can be direct, for example, by detection of a label directly attached to the test molecule. Alternatively, detection can be indirect, for example, by detecting a detectably labeled complex-binding agent, e.g., a labeled secondary antibody or other labeled molecule that can bind to complex between the carbohydrate on the array and the test molecule, or to the test molecule. The bound label can be observed using any available detection method. For example, an array CCD analyzer can be employed to detect chemiluminescence labeled molecules that are bound to array. In experiments illustrated herein an Agnitio BioIC Analyzer (BA-G2000, Agnitio Science and Technology Inc.) was used. The data from such an array CCD analyzer can be analyzed by using Agnitio LabIT2.3.6 image analysis software (Agnitio Science and Technology Inc.).

DEFINITIONS

The carbohydrate antigens Globo H, stage-specific embryonic antigen-3 (SSEA-3), and stage-specific embryonic antigen-4 (SSEA-4) are closely related to one another in either structure or in function. Globo H, SSEA-3 and SSEA-4 are globoseries glycosphingolipids, 1-3 with SSEA-3 being the non-fucosylated pentasaccharide precursor structure of Globo H, SSEA-4 is sialylated SSEA-3 with sialic acid alpha 2-3 links to the non-reducing end of galactose of SSEA-3. Other glycans include $Le^y$, $SLe^a$, and $SLe^x$.

A "defined glycan probe location" as used herein is a predefined region of a solid support to which a density of glycan molecules, all having similar glycan structures, is attached. The terms "glycan region," or "selected region", or simply "region" are used interchangeably herein for the term defined glycan probe location. The defined glycan probe location may have any convenient shape, for example, circular, rectangular, elliptical, wedge-shaped, and the like. In some embodiments, a defined glycan probe location and, therefore, the area upon which each distinct glycan type or a distinct group of structurally related glycans is attached is smaller than about 1 cm², or less than 1 mm², or less than 0.5 mm². In some embodiments the glycan probe locations have an area less than about 10,000 μm² or less than 100 μm². The glycan molecules attached within each defined glycan probe location are substantially identical. Additionally, multiple copies of each glycan type are present within each defined glycan probe location. The number of copies of each glycan types within each defined glycan probe location can be in the thousands to the millions.

As used herein, the arrays of the invention have defined glycan probe locations, each with "one type of glycan molecule." The "one type of glycan molecule" employed can be a group of substantially structurally identical glycan molecules or a group of structurally similar glycan molecules. There is no need for every glycan molecule within a defined glycan probe location to have an identical structure. In some embodiments, the glycans within a single defined glycan probe location are structural isomers, have variable numbers of sugar units or are branched in somewhat different ways. However, in general, the glycans within a defined glycan probe location have substantially the same type of sugar units and/or approximately the same proportion of each type of sugar unit. The types of substituents on the sugar units of the glycans within a defined glycan probe location are also substantially the same.

CHEMICAL DEFINITIONS

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, March's Advanced Organic Chemistry, 5th Edition, John Wiley & Sons, Inc., New York, 2001; Larock, Comprehensive Organic Transformations, VCH Publishers, Inc., New York, 1989; and Carruthers, Some Modern Methods of Organic Synthesis, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, Stereochemistry of Carbon Compounds (McGraw-Hill, N Y, 1962); and Wilen, Tables of Resolving Agents and Optical Resolutions p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("C1 alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl (C4), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted C$_{2-10}$ alkenyl. In certain embodiments, the alkenyl group is substituted C$_{2-10}$ alkenyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In certain embodiments, the heteroatom is independently selected from nitrogen, sulfur, and oxygen. In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms in the aromatic ring system ("C$_{6-14}$ aryl"). In some embodiments, an aryl group has six ring carbon atoms ("C$_6$ aryl"; e.g., phenyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C6-14 aryl. In certain embodiments, the aryl group is substituted C6-14 aryl.

Alkyl, alkenyl, alkynyl, carbocyclyl, heterocyclyl, aryl, and heteroaryl groups, as defined herein, which are divalent bridging groups are further referred to using the suffix -ene, e.g., alkylene, alkenylene, alkynylene, carbocyclylene, heterocyclylene, arylene, and heteroarylene.

The term "alkoxy" or "alkyloxy" refers to an —O-alkyl radical, wherein alkyl is optionally substituted alkyl as defined herein. Examples of alkoxy include, but are not limited to, methoxy, ethoxy, n-propoxy, isopropoxy, n-butoxy, iso-butoxy, sec-butoxy, and tert-butoxy.

The term "aryloxy" refers to an —O-aryl, wherein aryl is optionally substituted aryl as defined herein.

As used herein, the term "optionally substituted" refers to a substituted or unsubstituted moiety.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of —C(=O)Raa, —CHO, —CO$_2$Raa, —C(=O)N(Rbb)$_2$, —C(=NRbb)Raa, —C(=NRbb)ORaa, —C(=NRbb)N(Rbb)$_2$, —C(=O)NRbbSO$_2$Raa, —C(=S)N(Rbb)$_2$, —C(=O)SRaa, and —C(=S)SRaa, wherein Raa and Rbb are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —ORaa, —N(Rcc)$_2$, —CN, —C(=O)Raa, —C(=O)N(Rcc)$_2$, —CO$_2$Raa, —SO$_2$Raa, —C(=NRbb)Raa, —C(=NRcc)ORaa, —C(=NRcc)N(Rcc)$_2$, —SO$_2$N(Rcc)$_2$, —SO$_2$Rcc, —SO$_2$ORcc, —SORaa, —C(=S)N(Rcc)$_2$, —C(=O)SRcc, —C(=S)SRcc, —P(=O)$_2$Raa, —P(=O)(Raa)2, —P(=O)2N(Rcc)2, —P(=O)(NRcc)2, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two Rcc groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 Rdd groups, and wherein Raa, Rbb, Rcc, and Rdd are as defined above.

In certain embodiments, the substituent present on an oxygen atom is an oxygen protecting group (also referred to as a hydroxyl protecting group). Oxygen protecting groups include, but are not limited to, —Raa, —N(Rbb)$_2$, —C(=O)SRaa, —C(=O)Raa, —CO$_2$Raa, —C(=O)N(Rbb)$_2$, —C(=NRbb)Raa, —C(=NRbb)ORaa, —C(=NRbb)N(Rbb)$_2$, —S(=O)Raa, —SO$_2$Raa, —Si(Raa)$_3$, —P(Rcc)$_2$, —P(Rcc)$_3$, —P(=O)$_2$Raa, —P(=O)(Raa)$_2$, —P(=O)(ORcc)$_2$, —P(=O)$_2$N(Rbb)$_2$, and —P(=O)(NRbb)$_2$, wherein Raa, Rbb, and Rcc are as defined herein. Oxygen protecting groups are well known in the art and include those described in Protecting Groups in Organic Synthesis, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6, 7,7a-octahydro-7, 8,8-trimethyl-4, 7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzyl silyl, tri-p-xylyl silyl, triphenyl silyl, diphenylmethyl silyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1, 1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Antibodies: A Laboratory Manual, by Harlow and Lane s (Cold Spring Harbor Laboratory Press, 1988); and Handbook Of Experimental Immunology, Volumes I-IV (D. M. Weir and C. C. Blackwell, eds., 1986).

As used herein, the term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of O-glycosidic linkages between monosaccharides. For example, cellulose is a glycan (or more specifically a glucan) composed of β-1,4-linked D-glucose, and chitin is a glycan composed of β-1,4-linked N-acetyl-D-glucosamine. Glycans can be homo or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes. N-Linked glycans are found attached to the R-group nitrogen (N) of asparagine in the sequon. The sequon is a Asn-X-Ser or Asn-X-Thr sequence, where X is any amino acid except praline.

As used herein, the term "antigen" is defined as any substance capable of eliciting an immune response.

As used herein, the term "immunogenicity" refers to the ability of an immunogen, antigen, or vaccine to stimulate an immune response.

As used herein, the term "CD1d" refers to a member of the CD1 (cluster of differentiation 1) family of glycoproteins expressed on the surface of various human antigen-presenting cells. CD1d presented lipid antigens activate natural killer T cells. CD1d has a deep antigen-binding groove into which glycolipid antigens bind. CD1d molecules expressed on dendritic cells can bind and present glycolipids, including GalCer analogs such as C34.

As used herein, the term "epitope" is defined as the parts of an antigen molecule which contact the antigen binding site of an antibody or a T cell receptor.

As used herein, the term "vaccine" refers to a preparation that contains an antigen, consisting of whole disease-causing organisms (killed or weakened) or components of such organisms, such as proteins, peptides, or polysaccharides, that is used to confer immunity against the disease that the organisms cause. Vaccine preparations can be natural, synthetic or derived by recombinant DNA technology.

As used herein, the term "antigen specific" refers to a property of a cell population such that supply of a particular antigen, or a fragment of the antigen, results in specific cell proliferation.

As used herein, the term "specifically binding," refers to the interaction between binding pairs (e.g., an antibody and an antigen). In various instances, specifically binding can be embodied by an affinity constant of about $10^{-6}$ moles/liter, about $10^{-7}$ moles/liter, or about $10^{-8}$ moles/liter, or less.

As used herein, the term "Flow cytometry" or "FACS" means a technique for examining the physical and chemical properties of particles or cells suspended in a stream of fluid, through optical and electronic detection devices.

As used herein, the terms glycoenzymes refers to at least in part the enzymes in the globoseries biosynthetic pathway; exemplary glycoenzymes include alpha-4GalT; beta-4Gal-NAcT-I; or beta-3GalT-V enzymes.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In one embodiment, the antibody will be purified (1) to greater than 95% by weight of antibody as determined by, for example, the Lowry method, and in some embodiments more than 99% by weight, (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

The term "support" or "substrate" as used interchangeably herein refers to a material or group of materials, comprising one or a plurality of components, with which one or more molecules are directly or indirectly bound, attached, synthesized upon, linked, or otherwise associated. A support may be constructed from materials that are biological, non-biological, inorganic, organic or a combination of these. A support may be in any appropriate size or configuration based upon its use within a particular embodiment.

The term "target" as used herein refers to a species of interest within an assay. Targets may be naturally occurring or synthetic, or a combination. Targets may be unaltered (e.g., utilized directly within the organism or a sample thereof), or altered in a manner appropriate for the assay (e.g., purified, amplified, filtered). Targets may be bound through a suitable means to a binding member within certain assays. Non-limiting examples of targets include, but are not restricted to, antibodies or fragments thereof, cell membrane receptors, monoclonal antibodies and antisera reactive with specific antigenic determinants (such as on viruses, cells or other materials), drugs, oligonucleotides, nucleic acids, peptides, cofactors, sugars, lectins polysaccharides, cells, cellular membranes, and organelles. Target may be any suitable size depending on the assay.

The phrase "substantially similar," "substantially the same", "equivalent", or "substantially equivalent", as used herein, denotes a sufficiently high degree of similarity between two numeric values (for example, one associated with a molecule and the other associated with a reference/comparator molecule) such that one of skill in the art would consider the difference between the two values to be of little or no biological and/or statistical significance within the context of the biological characteristic measured by said values (e.g., Kd values, anti-viral effects, etc.). The difference between said two values is, for example, less than about 50%, less than about 40%, less than about 30%, less than about 20%, and/or less than about 10% as a function of the value for the reference/comparator molecule.

The phrase "substantially reduced," or "substantially different", as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Antibodies" (Abs) and "immunoglobulins" (IGs) are glycoproteins having the same structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent, multivalent antibodies, multi specific antibodies (e.g., bispecific antibodies so long as they exhibit the desired biological activity) and may also include certain antibody fragments (as described in greater detail herein). An antibody can be chimeric, human, humanized and/or affinity matured.

The "variable region" or "variable domain" of an antibody refers to the amino-terminal domains of heavy or light chain of the antibody. These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, noncovalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably, to refer to an antibody in its substantially intact form, not antibody fragments as defined below. The terms particularly refer to an antibody with heavy chains that contain the Fc region.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise an antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256: 495 (1975); Harlow et al., Antibodies: A Laboratory Manual, (Cold Spring Harbor Laboratory Press, 2nd ed. 1988); Hammerling et al., in: Monoclonal Antibodies and T-Cell hybridomas 563-681 (Elsevier, N.Y., 1981)), recombinant DNA methods (see, e.g., U.S. Pat. No. 4,816, 567), phage display technologies (See, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996) and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

As used herein, "normal levels" can be, for example, a reference value or range based on measurements of the levels of TACA bound antibodies in samples from normal patients or a population of normal patients. "Normal levels" can also be, for example, a reference value or range based on measurements of the TACAs in samples from normal patients or a population of normal patients.

As used herein a "subject" is a mammal. Such mammals include domesticated animals, farm animals, animals used in experiments, zoo animals and the like. In some embodiments, the subject is a human.

A "disorder" is any condition that would benefit from treatment with an antibody of the invention. This includes chronic and acute disorders or diseases including those pathological conditions which predispose the mammal to the disorder in question. Non-limiting examples of disorders to be treated herein include cancer.

The terms "cell proliferative disorder" and "proliferative disorder" refer to disorders that are associated with some degree of abnormal cell proliferation. In one embodiment, the cell proliferative disorder is cancer.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "globoseries-related disorder" refers to or describes a disorder that is typically characterized by or contributed to by aberrant functioning or presentation of the pathway. Examples of such disorders include, but are not limited to, hyperproliferative diseases, including cancer.

Some of the structural elements of the glycans described herein are referenced in abbreviated form as understood by person of ordinary skill in the art.

Examples of the hyperproliferative disease and/or condition includes neoplasm/hyperplasia and cancer, including, but not limited to, brain cancer, lung cancer, breast cancer, oral cancer, esophagus cancer, stomach cancer, liver cancer, bile duct cancer, pancreas cancer, colon cancer, kidney cancer, cervix cancer, ovary cancer and prostate cancer. In some embodiments, the cancer is brain cancer, lung cancer, breast cancer, ovarian cancer, prostate cancer, colon cancer, or pancreas cancer. In other embodiments, the hyperproliferative disease state is associated with breast, ovary, lung, pancreatic, stomach (gastric), colorectal, prostate, liver, cervix, esophagus, brain, oral, and kidney.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

In one embodiment, the present disclosure provides a method for determining the therapeutic efficacy of an antineoplastic agent in treatment of a subject in need thereof, comprising: (a) providing a sample form a subject; (b) contacting a sample collected from a subject; (c) assaying the binding of one or more of tumor associated antigens (TACAs) or antibodies; and (d) determining the therapeutic effect of an antineoplastic agent in treatment for neoplasm based on the assayed value of the glycan detection. The present disclosure provides evidence of surprising additive and/or synergistic efficacy and utility in the combination usage of the linker-glycoconjugates (e.g. Globo H) in the detection of cancer. This provides the bases that the linkers and the conjugates herein are useful as companion diagnostic compositions and methods for any therapeutics targeting the determinants and molecules associated with globoseries glycoproteins. Exemplary therapeutic methods and compositions comprising antineoplastic agents suitable for use in combination with the present disclosure as companion diagnostic methods and uses are described (e.g. OBI-822, OBI-833 and OBI-888) in the disclosures of for example, patent publication numbers: WO2015159118, WO2014107652 and WO2015157629). The contents of each of which is incorporated by reference.

The inventions described and claimed herein have many attributes and embodiments including, but not limited to, those set forth or described or referenced in this Detailed Description. It is not intended to be all-inclusive and the inventions described and claimed herein are not limited to or by the features or embodiments identified in this Detailed Description, which is included for purposes of illustration only and not restriction.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group. Other embodiments are within the following claims. In addition, where features or aspects of the invention are described in terms of Markush groups, those skilled in the art will recognize that the invention is also thereby described in terms of any individual member or subgroup of members of the Markush group.

Examples

The instant disclosure and examples herein documents the discovery of surprising efficacy of the linkers as described herein, their glyco-conjugates with globoseries of glycoprotein e.g. SSEA-3, SSEA-4, Globo H, Le$^y$, SLe$^a$, and SLe$^x$; and methods of using them in arrays to achieve surprising efficacy in disease state (e.g. cancer) determination, prediction, and/or diagnosis.

General Methodologies

All starting chemical reagents were obtained and used without further purification. Dichloromethane ($CH_2Cl_2$) was distilled over calcium hydride. Diethyl Ether ($Et_2O$) was distilled over sodium. Molecular sieves (MS, AW-300) were crushed and activated before use. Reactions were monitored with analytical TLC on silica gel 60 F254 plates and visualized under UV (254 nm) and/or by staining with acidic cerium ammonium molybdate. Flash column chromatography was performed on silica gel (35-75 μm) or LiChroprep RP18. $^1$H-NMR spectra were recorded on a Bruker DRX-500 (500 MHz) or DRX-600 (600 MHZ) spectrometer at 20° C. Chemical shifts (in ppm) were determined relative to either tetramethylsilane in deuterated chloroform (δ=0 ppm) or acetone in deuterated water (δ=2.05 ppm). Coupling constants in Hz were measured from one-dimensional spectra. $^{13}$C Attached Proton Test ($^{13}$C-APT) NMR spectra were obtained by using the same Bruker NMR spectrometer (125 or 150 MHz) and were calibrated with $CDCl_3$ (δ=77 ppm). Coupling constants (J) are reported in Hz. Splitting patterns are described by using the following abbreviations: s, singlet; brs, broad singlet; d, doublet; t, triplet; q, quartet; m, multiplet. 1H NMR spectra are reported in this order: chemical shift; multiplicity; number(s) of proton; coupling constant(s).

Example 1

Synthesis of Globo H-Lipid, SSEA-3-Lipid and SSEA-4-Lipid

Synthesis of New Lipid Chains:

After comparing the commercially available lipid chains, we found that the 1, 2-Di-O-hexadecyl-sn-glycerol had similar log P with ceramide and could be obtained at a lower price than other lipid chains. Based on the assay optimization strategy, the lipid chain need to contain the carboxyl group to couple with the TACAs. The commercial available glycerol should be modified by chemical process. The glycerol was treated with TEMPO, and BAIB as oxidation agent to afford the carboxyl product (lipid chain-1) in 98% yield. On the other side, the glycerol was reacted with glutaric anhydride under the basic condition to extend six carbon unit and form the carboxyl group (lipid chain-2) in 71% yield. The synthesis reaction scheme was listed in FIG. 3.

Figure 3A:
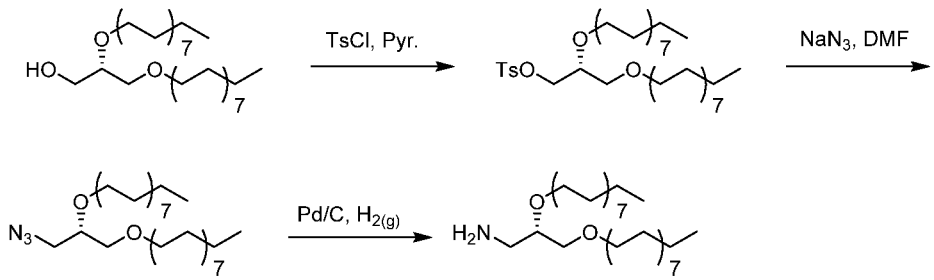
FIG. 3A and FIG. 3B. The reaction scheme for synthesis of lipid chain analogues (from lipid chain 1 to lipid chain 6, which can also be referred to as lipid-1 to lipid-6, respectively). This reaction is including three steps of the lipid-NH$_2$ synthesis (FIG. 3A) and lipid chain analogues formation (FIG. 3B).
Figure 3B:
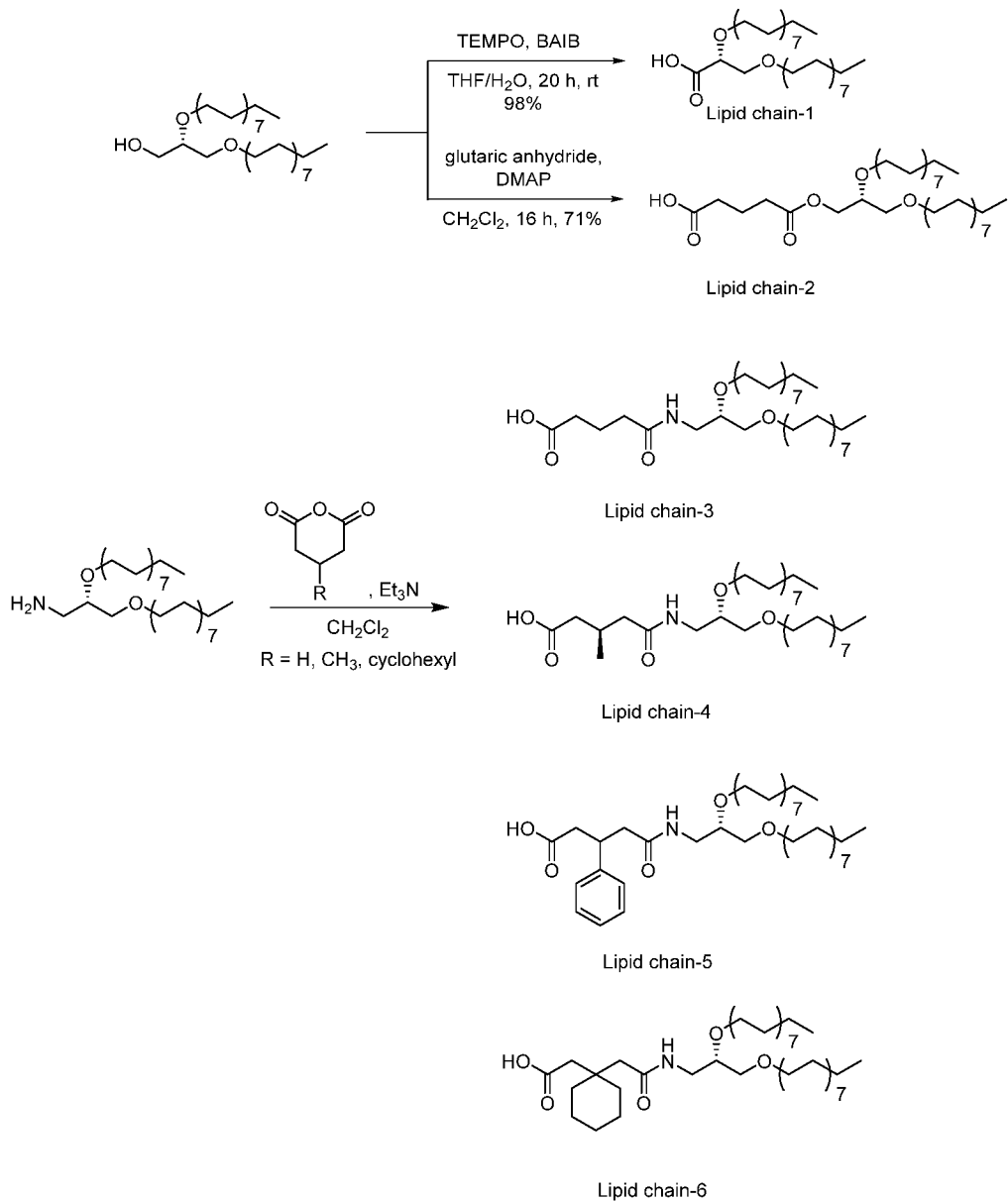
Figure 4A:
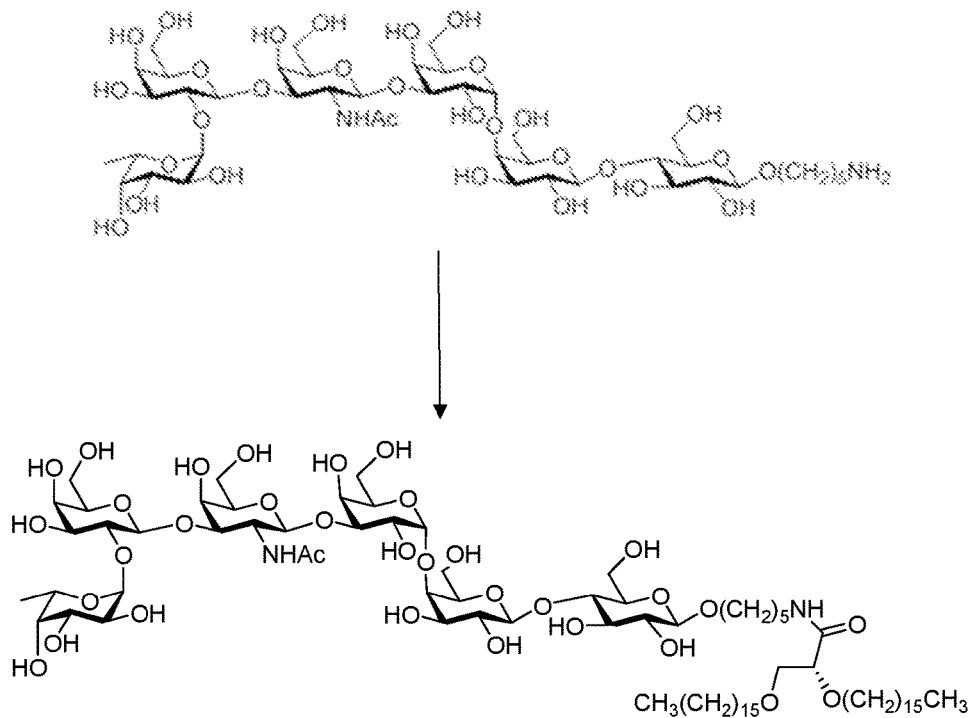
FIG. 4A, FIG. 4B, FIG. 4C, FIG. 4D, FIG. 4E and FIG. 4F. The coupling reaction of Globo H—NH$_2$ and lipid chain products.
Figure 4B:
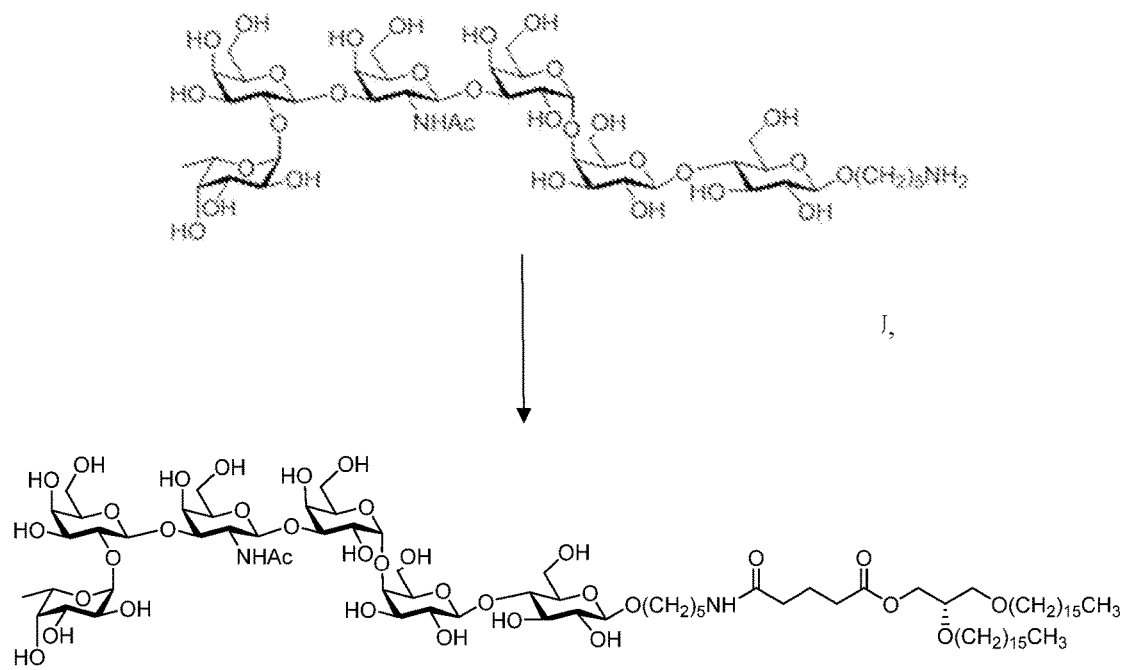
Figure 4C:
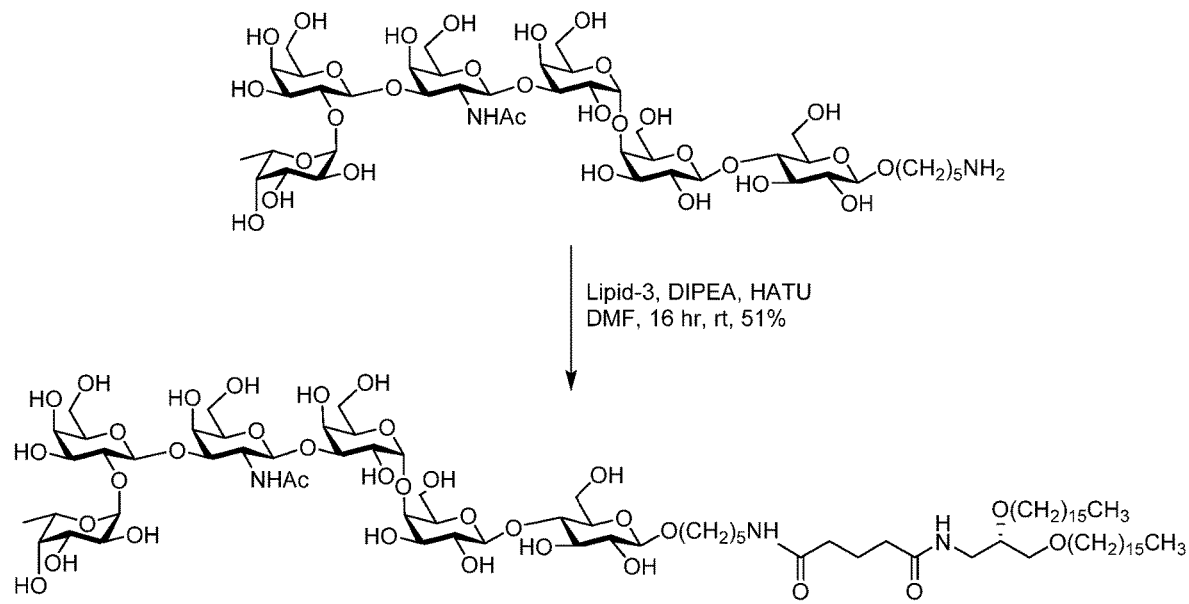
Figure 4D:
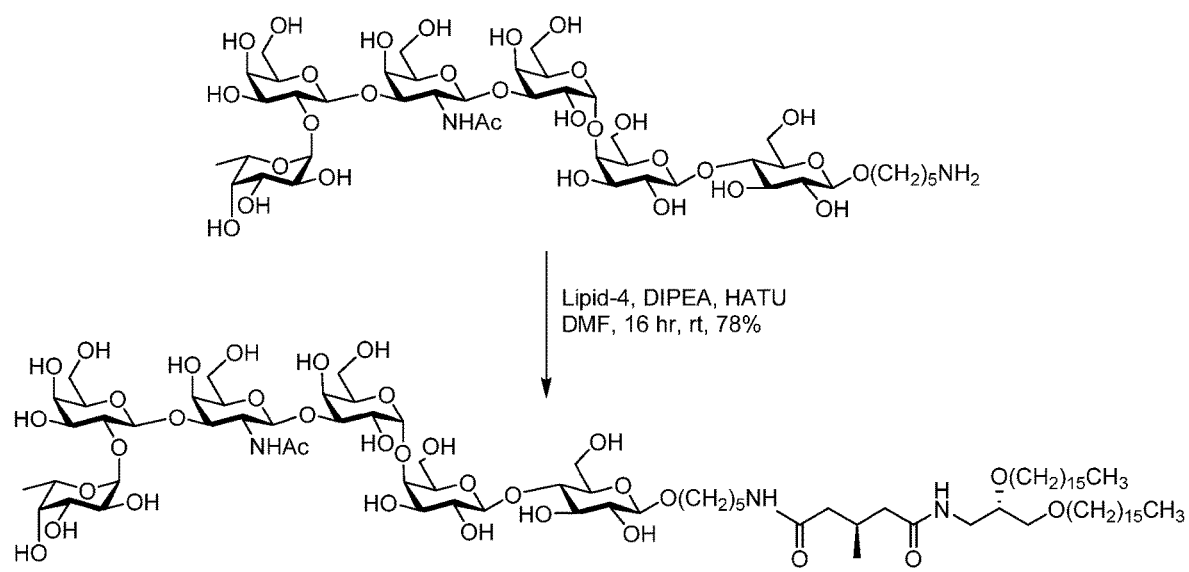
Figure 4E:
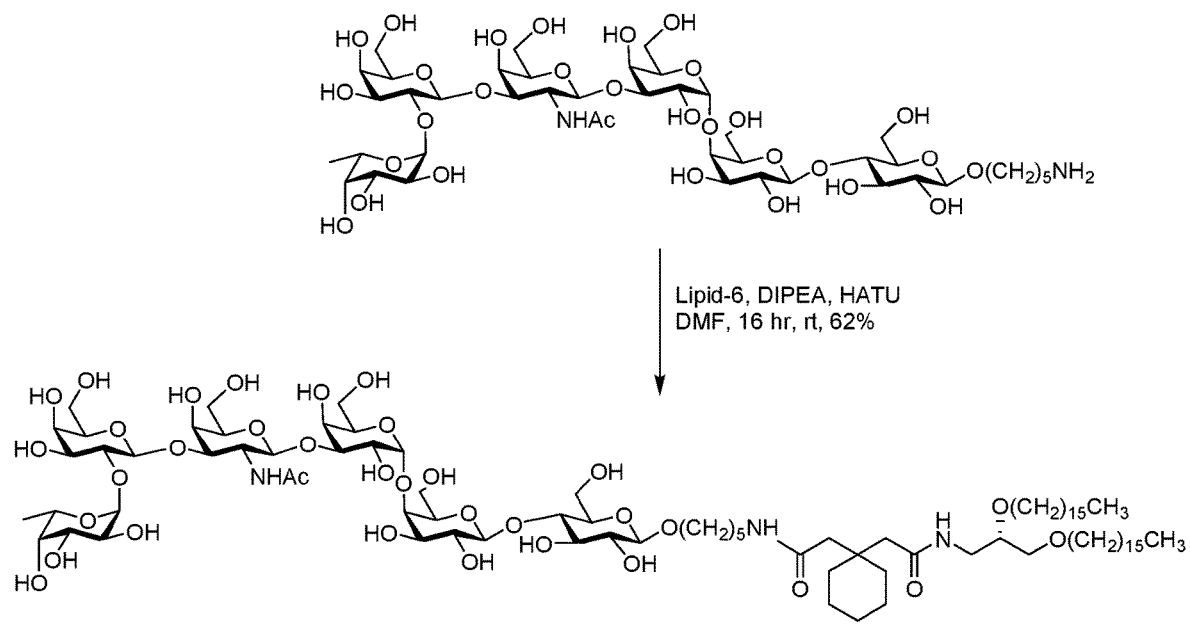
Figure 4F:
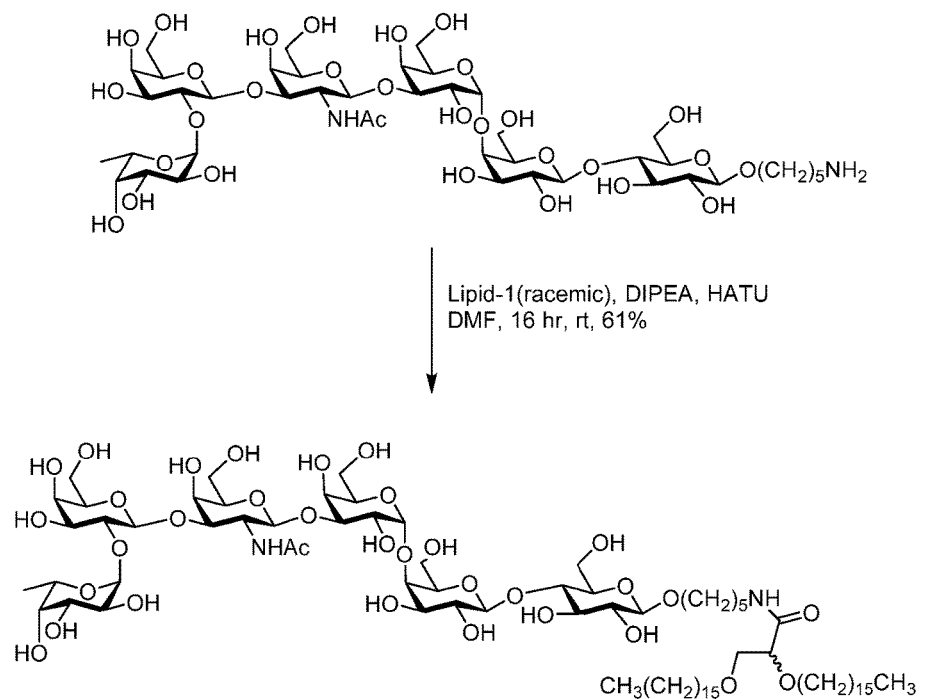

In addition, there were three steps to synthesize lipid-$NH_2$ and listed in FIG. 3:

Step1. Tosylation:

To a stirred solution of 1.0 g of 1,2-O-Dihexadecyl-sn-glycerol in 1.5 mL of dry pyridine, and then 0.6 g of 4-nitrobenzenesulfonyl chloride was added at room temperature. After 16 hours, 100 mL of ethyl acetate was added to the solution, and washed with 10 mL 1N HCl (aq) and 10 mL of saturated $NaHCO_3$(aq). The organic layer was dried over $Na_2SO_4$ and evaporated to give crude product. The residue was purified by Si-gel chromatography (EtOAc/n-hexane 1:20) to give tosylated lipid (yield: 95%).

Step2. Azide Replacement:

The tosylated lipid (0.46 g) was dissolved in 3.5 mL of DMF. Then $NaN_3$ (351 mg, 5 mmol) was added and the mixture was heated at 80° C. for 16 hours. Then 30 mL of water added and extracted with 20 mL of EtOAc. The extract was dried over $Na_2SO_4$ and evaporated to give crude product. The residue was purified by Si-gel chromatography (EtOAc/n-hexane 1:50) to give azido-lipid (yield: 92%).

Step3. Azide Reduction:

The azido-lipid (0.35 g) was dissolved in 3 mL of EtOAc, then Pd/C (150 mg of 10% Pd) was added and the mixture was hydrogenated under hydrogen balloon for overnight. The catalyst was removed by filtration through celite, then concentrated to give the crude product to next step.

To a stirred solution of 1 equiv. lipid-$NH_2$ and 5 equiv. DIPEA in $CH_2Cl_2$, and then 1.2 equiv. glutaric anhydride derivative was added at room temperature. Then water was added and extracted with $CH_2Cl_2$. The extract was dried over $Na_2SO_4$ and evaporated to give crude product. The residue was purified by LH-20 (MeOH/$CHCl_3$ 1:2) to give lipid analogues.

Coupling of Globo H—$NH_2$ and Lipid Chain Product Afforded the New Composition Via the Amide Bond Formation:

The Globo H—$NH_2$ was coupled with lipid chain-1, lipid chain-2, lipid chain-3, lipid chain-4, lipid chain-6 and lipid chain-1 (racemic) through the same amide bond formation condition in 53%, 64%, 51%, 78%, 62% and 61% yield, individually. The coupling reaction scheme was listed in FIG. 4.

Figure 5A:
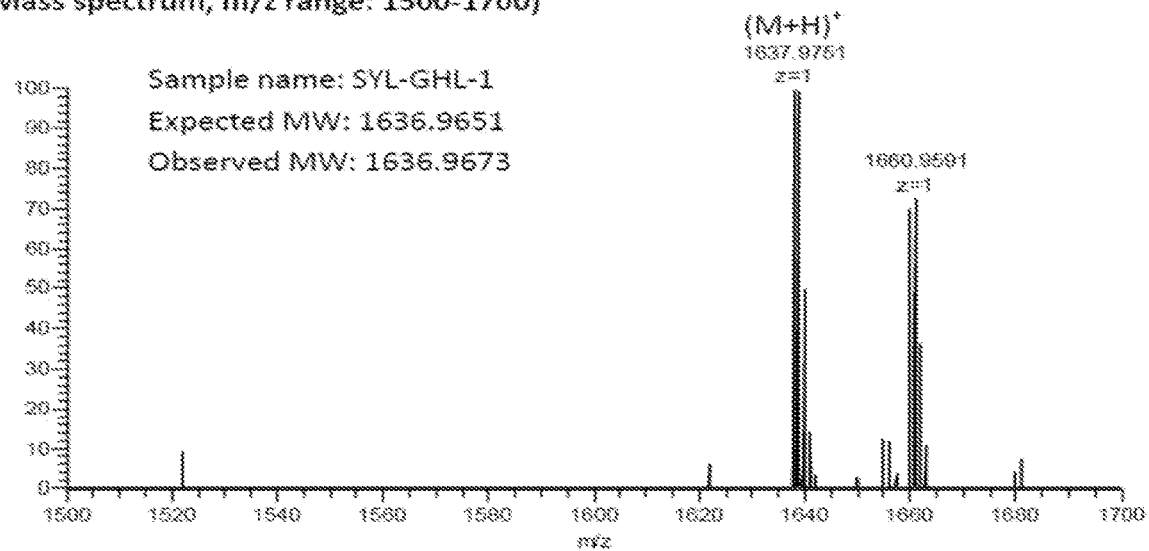
FIG. 5A, FIG. 5B, FIG. 5C, FIG. 5D, FIG. 5E, FIG. 5F. The mass spectrum of Globo H-lipid chain products.

Globo H-Lipid 1:

$^1$H-NMR (600 MHz, CD$_3$OD/CDCl$_3$) δ 5.22 (d, J=3.9 Hz, 1H), 4.94 (d, J=3.7 Hz, 1H), 4.54 (d, J=7.8 Hz, 2H), 4.42-4.39 (m, 1H), 4.28-4.21 (m, 3H), 4.14 (d, J=1.8 Hz, 1H), 4.08-4.05 (m, 2H), 3.99 (s, 1H), 3.91-3.65 (m, 24H), 3.61-3.46 (m, 11H), 3.40-3.37 (m, 1H), 3.28-3.14 (m, 3H), 2.00 (s, 3H), 1.66-1.51 (m, 9H), 1.44-1.24 (m, 54H), 0.90-0.83 (m, 6H); $^{13}$C-NMR (150 MHz, CD$_3$OD/CDCl$_3$) δ 174.5 (C), 173.1 (C), 105.5 (CH), 105.3 (CH), 104.2 (CH), 103.8 (CH), 102.9 (CH), 101.1 (CH), 81.7 (CH), 81.5 (CH), 80.6 (CH), 80.3 (CH), 78.4 (CH), 76.7 (CH), 76.4 (CH), 76.35 (CH), 76.3 (CH), 75.4 (CH), 74.8 (CH), 74.7 (CH), 73.5 (CH), 72.7 (CH$_2$), 72.6 (CH), 72.5 (CH$_2$), 72.2 (CH$_2$), 71.5 (CH), 70.8 (CH$_2$), 70.7 (CH), 70.5 (CH), 70.4 (CH), 69.6 (CH), 69.5 (CH), 68.2 (CH), 62.7 (CH$_2$), 62.6 (CH$_2$), 62.56 (CH$_2$), 62.0 (CH$_2$), 61.6 (CH$_2$), 53.1 (CH), 40.5 (CH$_2$), 40.0 (CH$_2$), 33.1 (CH$_2$), 30.8 (CH$_2$), 30.78 (CH$_2$), 30.73 (CH$_2$), 30.6 (CH$_2$), 30.57 (CH$_2$), 30.5 (CH$_2$), 30.34 (CH$_2$), 30.3 (CH$_2$), 27.3 (CH$_2$), 27.2 (CH$_2$), 24.4 (CH$_2$), 24.35 (CH$_2$), 23.8 (CH$_2$), 23.6 (CH$_3$), 16.8 (CH$_3$), 14.6 (CH$_3$); HRMS (ESI, MH+) calcd for C$_{78}$H$_{145}$N$_2$O$_{33}$ 1637.9730. found 1637.9751. The mass spectrum was showed at FIG. 5A.

The lipid chain 1 (1.2 eq) was dissolved in 1 mL of dry DMF with stirring. O-(7-Azabenzotriazole-1-yl)-N,N,N,N'-tetramethyluronium hexafluorophosphate (HATU, 1.2 eq) was added as a solid and stirred for 10 min at room temperature. Globo H-pentylamine (1.0 eq) was added and the resulting solution was stirred for 20 min before diisopropylethylamine (DIPEA, 5 eq) was added by syringe. The mixture was stirred for 16 hours at room temperature, and quenched by methanol. The mixture was concentrated and purified by LH-20 to yield the final product (53%).

Figure 5B:
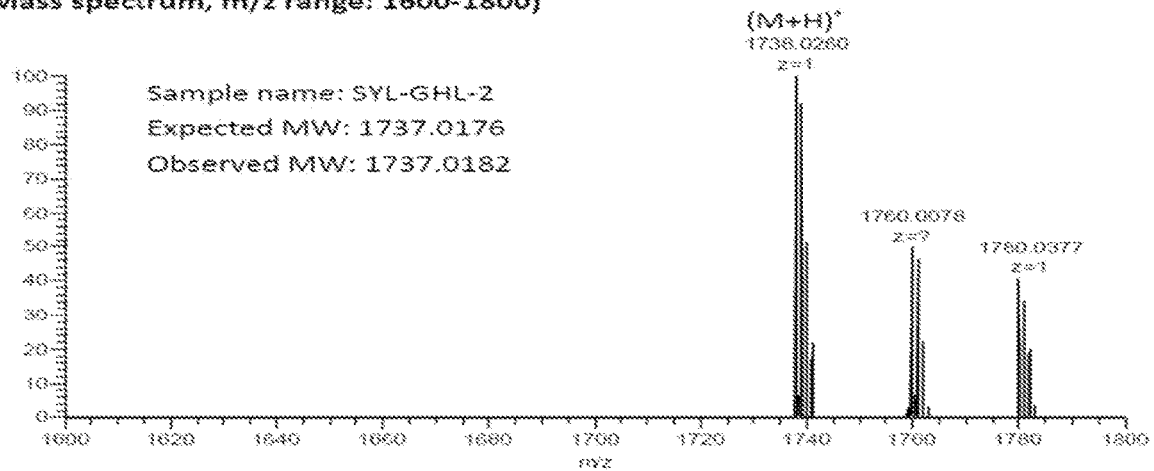

Globo H-Lipid 2:

$^1$H-NMR (600 MHz, CD$_3$OD/CDCl$_3$) δ 5.22 (d, J=3.9 Hz, 1H), 4.94 (d, J=3.9 Hz, 1H), 4.54 (d, J=7.7 Hz, 2H), 4.42-4.41 (m, 1H), 4.28-4.20 (m, 4H), 4.13 (s, 1H), 4.11-4.06 (m, 3H), 3.98 (s, 1H), 3.93-3.64 (m, 24H), 3.59-3.44 (m, 14H), 3.40-3.37 (m, 1H), 3.26-3.25 (m, 1H), 3.16 (t, J=7.1 Hz, 2H), 2.38 (t, J=7.4 Hz, 2H), 2.22 (t, 2H, J=7.4 Hz), 2.00 (s, 3H), 1.93-1.90 (m, 2H), 1.67-1.62 (m, 2H), 1.59-1.50 (m, 6H), 1.43-1.24 (m, 57H), 0.89 (t, J=7.0 Hz, 6H); $^{13}$C-NMR (150 MHz, CD$_3$OD/CDCl$_3$) 175.0 (C), 174.5 (C), 174.48 (C), 105.5 (CH), 105.2 (CH), 104.2 (CH), 103.7 (CH), 102.8 (CH), 101.1 (CH), 81.4 (CH), 80.6 (CH), 80.3 (CH), 78.4 (CH), 77.9 (CH), 76.7 (CH), 76.4 (CH), 76.3 (CH), 76.29 (CH), 75.4 (CH), 74.8 (CH), 74.7 (CH), 73.4 (CH), 72.7 (CH$_2$), 72.6 (CH), 72.57 (CH), 71.6 (CH$_2$), 71.5 (CH), 71.4 (CH$_2$), 70.7 (CH), 70.5 (CH), 70.4 (CH), 69.5 (CH), 69.46 (CH), 68.1 (CH), 64.9 (CH$_2$), 62.7 (CH$_2$), 62.6 (CH$_2$), 62.55 (CH$_2$), 62.0 (CH$_2$), 61.5 (CH$_2$), 53.1 (CH), 40.4 (CH$_2$), 36.1 (CH$_2$), 34.3 (CH$_2$), 33.1 (CH$_2$), 31.1 (CH$_2$), 30.8 (CH), 30.76 (CH$_2$), 30.72 (CH$_2$), 30.6 (CH$_2$), 30.5 (CH$_2$), 30.4 (CH$_2$), 30.1 (CH$_2$), 27.3 (CH$_2$), 27.2 (CH$_2$), 24.4 (CH$_2$), 23.7 (CH$_2$), 23.6 (CH$_3$), 22.3 (CH), 16.8 (CH$_3$), 14.6 (CH$_3$); HRMS (ESI, MH+) calcd for C$_{83}$H$_{153}$N$_2$O$_{35}$ 1738.0254. found 1738.0260. The mass spectrum was showed at FIG. 5B.

The lipid chain 2 (1.2 eq) was dissolved in 1 mL of dry DMF with stirring. O-(7-Azabenzotriazole-1-yl)-N,N,N,N'-tetramethyluronium hexafluorophosphate (HATU, 1.2 eq) was added as a solid and stirred for 10 min at room temperature. Globo H-pentylamine (1.0 eq) was added and the resulting solution was stirred for 20 min before diisopropylethylamine (DIPEA, 5 eq) was added by syringe. The mixture was stirred for 16 hours at room temperature, and quenched by methanol. The mixture was concentrated and purified by LH-20 to yield the final product (64%).

Figure 5C:
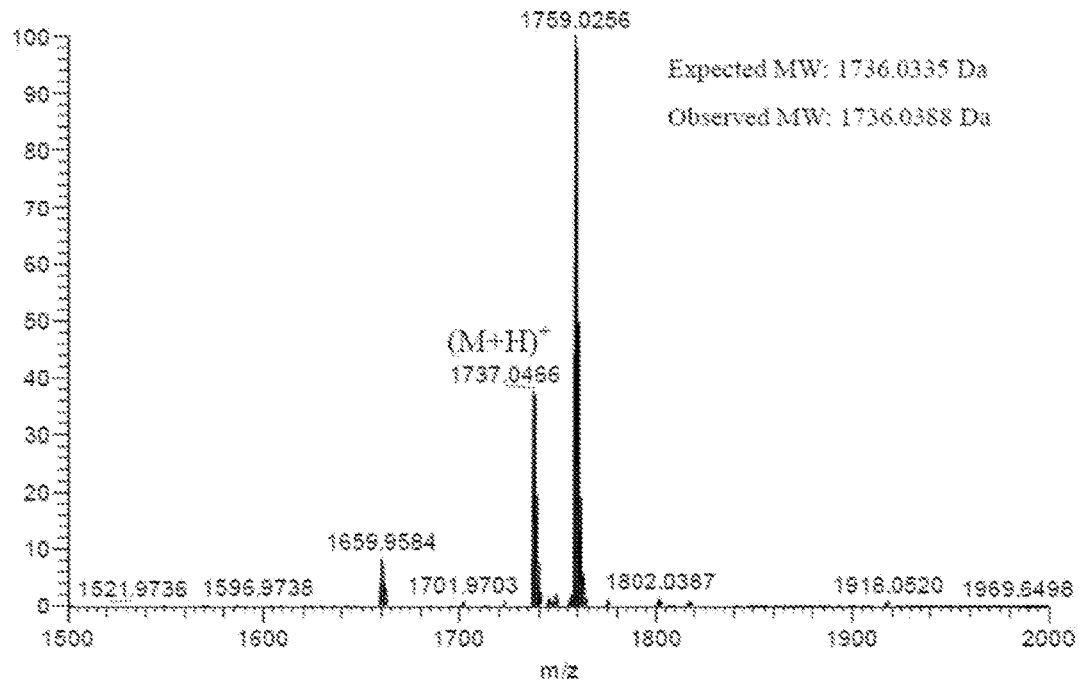

Globo H-Lipid 3:

$^1$H-NMR (400 MHz, 10% CDCl$_3$ in CD$_3$OD) δ 5.21 (d, J=3.8 Hz, 1H), 4.94 (d, J=3.9 Hz, 1H), 4.53 (d, J=7.5 Hz, 2H), 4.49 (br, 1H), 4.41 (dd, J=3.7, 3.7 Hz, 1H), 4.27 (d, J=7.8 Hz, 1H), 4.25-4.19 (m, 2H), 4.13 (d, J=2.7 Hz, 1H), 4.08-4.04 (m, 2H), 3.98-3.64 (m, 21H), 3.58-3.33 (m, 17H), 3.27-3.21 (m, 2H), 3.16 (dd, J=7.0, 7.0 Hz, 2H), 2.22 (t, J=7.6 Hz, 2H), 2.20 (t, J=8.0 Hz, 2H), 2.00 (s, 3H), 1.92-1.84 (m, 2H), 1.68-1.61 (m, 2H), 1.57-1.49 (m, 6H), 1.45-1.37 (m, 2H), 1.34-1.24 (m, 55H), 0.88 (t, J=7.0 Hz, 6H); $^{13}$C-NMR (100 MHz, 10% CDCl$_3$ in MeOD) δ 175.2 (C), 175.0 (C), 174.3 (C), 105.2 (CH), 105.0 (CH), 104.0 (CH), 103.5 (CH), 102.7 (CH), 100.9 (CH), 81.2 (CH), 80.4 (CH), 80.2 (CH), 79.1 (CH), 78.3 (CH), 78.3 (CH), 76.5 (CH), 76.2 (CH), 76.1 (CH), 75.1 (CH), 74.6 (CH), 74.5 (CH), 73.2 (CH), 72.5 (CH$_2$), 72.5 (CH), 72.4 (CH), 72.3 (CH$_2$), 71.3 (CH), 71.2 (CH$_2$), 70.5 (CH$_2$), 70.3 (CH), 70.2 (CH), 69.3 (CH), 69.2 (CH), 68.0 (CH), 62.5 (CH$_2$), 62.4 (CH$_2$), 61.8 (CH$_2$), 61.3 (CH$_2$), 52.9 (CH), 41.4 (CH$_2$), 40.2 (CH$_2$), 36.2 (CH$_2$), 32.9 (CH$_2$), 30.9 (CH$_2$), 30.6 (CH$_2$), 30.4 (CH$_2$), 30.3 (CH$_2$), 30.1 (CH$_2$), 29.9 (CH$_2$), 27.1 (CH$_2$), 27.0 (CH$_2$), 24.2 (CH$_2$), 23.5 (CH$_2$), 23.4 (CH$_2$), 16.6 (CH$_3$), 14.4 (CH$_3$); HRMS (ESI, M+Na$^+$) Calcd for C$_{83}$H$_{153}$N$_3$O$_{34}$Na 1759.0256. found 1759.0228. The mass spectrum was showed at FIG. 5C.

The lipid chain 3 (1.2 eq) was dissolved in 1 mL of dry DMF with stirring. O-(7-Azabenzotriazole-1-yl)-N,N,N,N'-tetramethyluronium hexafluorophosphate (HATU, 1.2 eq) was added as a solid and stirred for 10 min at room temperature. Globo H-pentylamine (1.0 eq) was added and the resulting solution was stirred for 20 min before diisopropylethylamine (DIPEA, 5 eq) was added by syringe. The mixture was stirred for 16 hours at room temperature, and quenched by methanol. The mixture was concentrated and purified by LH-20 to yield the final product (51%).

Figure 5D:
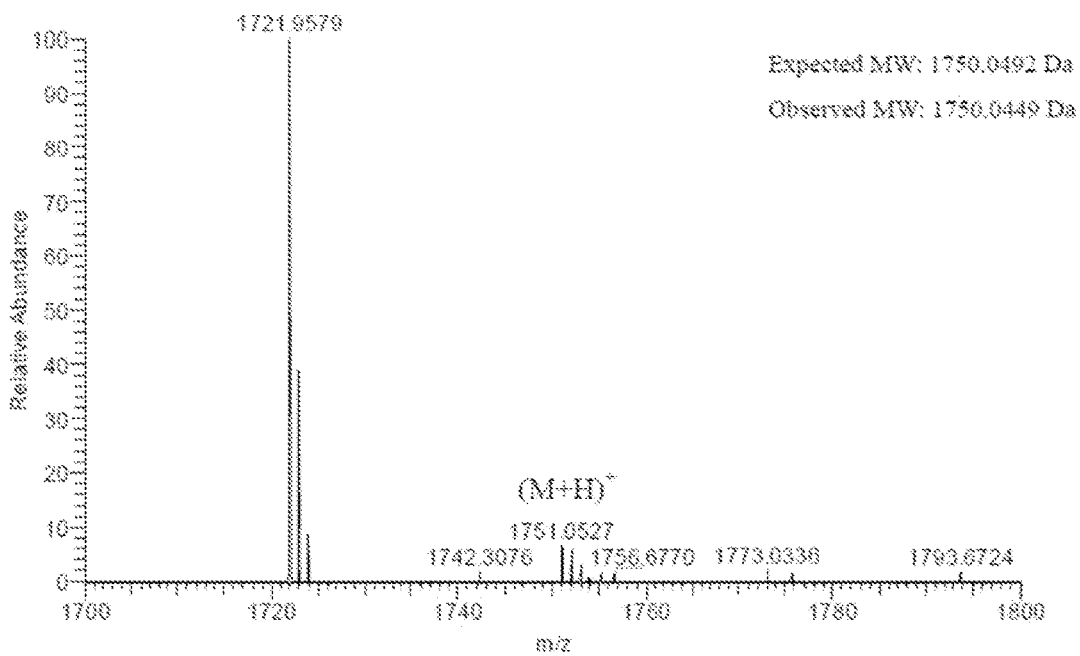

Globo H-Lipid 4:

$^1$H-NMR (600 MHz, CD$_3$OD) δ 5.22 (d, J=4.2 Hz, 1H), 4.98 (d, J=3.6 Hz, 1H), 4.55-4.54 (m, 2H), 4.44-4.43 (m, 3H), 4.30 (d, J=7.8 Hz, 1H), 4.25 (q, J=6.6 Hz, 1H), 4.19 (dd, J=7.2, 5.4 Hz, 1H), 4.15 (d, J=2.4 Hz, 1H), 4.10-4.09 (m, 1H), 4.08-4.06 (m, 1H), 4.01 (s, 1H), 3.98 (dd, J=10.2, 3.6 Hz, 1H), 3.94-3.87 (m, 5H), 3.85-3.76 (m, 12H), 3.75-3.68 (m, 9H), 3.62-3.55 (m, 11H), 3.54-3.49 (m, 4H), 3.48-3.45 (m, 4H), 3.42-3.39 (m, 3H), 3.32-3.26 (m, 3H), 3.20 (t, J=7.2 Hz, 2H), 2.38-2.32 (m, 1H), 2.29-2.23 (m, 2H), 2.12-2.06 (m, 3H), 2.02 (s, 3H), 1.70-1.65 (m, 3H), 1.61-1.53 (m, 8H), 1.47-1.41 (m, 3H), 1.29 (s, 53H), 1.00 (d, J=6.6 Hz, 4H), 0.91 (t, J=6.8 Hz, 7H); $^{13}$C-NMR (150 MHz, CD$_3$OD) δ 174.5 (C), 174.3 (C), 105.1 (CH), 104.8 (CH), 103.8 (CH), 103.2 (CH), 102.6 (CH), 100.9 (CH), 81.3 (CH), 80.6 (CH), 80.5 (CH), 78.1 (CH), 76.3 (CH), 76.0 (CH), 75.9 (CH), 75.7 (CH), 74.9 (CH), 74.4 (CH), 73.0 (CH), 72.6 (CH$_2$), 72.2 (CH), 72.1 (CH), 71.2 (CH), 70.6 (CH$_2$), 70.1 (CH), 69.0 (CH), 68.9 (CH), 68.0 (CH), 62.6 (CH$_2$), 62.3 (CH$_2$), 62.2 (CH$_2$), 61.9 (CH$_2$), 61.3 (CH$_2$), 52.7 (CH), 43.7 (CH$_2$), 41.4 (CH$_2$), 40.1 (CH$_2$), 32.8 (CH$_2$), 30.9 (CH$_2$), 30.52 (CH$_2$), 30.5 (CH$_2$), 30.3 (CH$_2$), 30.2 (CH$_2$), 30.03 (CH$_2$), 30.0 (CH), 29.9 (CH$_2$), 27.0 (CH$_2$), 26.9 (CH$_2$), 24.2 (CH$_2$), 23.5 (CH$_2$), 23.4 (CH$_2$), 20.0 (CH$_3$), 16.7 (CH$_3$), 14.5 (CH$_3$); HRMS (ESI, M+H$^+$) calcd for C$_{84}$H$_{156}$N$_3$O$_{34}$ 1751.0570. found 1751.0527. The mass spectrum was showed at FIG. 5D.

The lipid chain 4 (1.2 eq) was dissolved in 1 mL of dry DMF with stirring. O-(7-Azabenzotriazole-1-yl)-N,N,N,N'-tetramethyluronium hexafluorophosphate (HATU, 1.2 eq)

was added as a solid and stirred for 10 min at room temperature. Globo H-pentylamine (1.0 eq) was added and the resulting solution was stirred for 20 min before diisopropylethylamine (DIPEA, 5 eq) was added by syringe. The mixture was stirred for 16 hours at room temperature, and quenched by methanol. The mixture was concentrated and purified by LH-20 to yield the final product (78%).

Figure 5E:
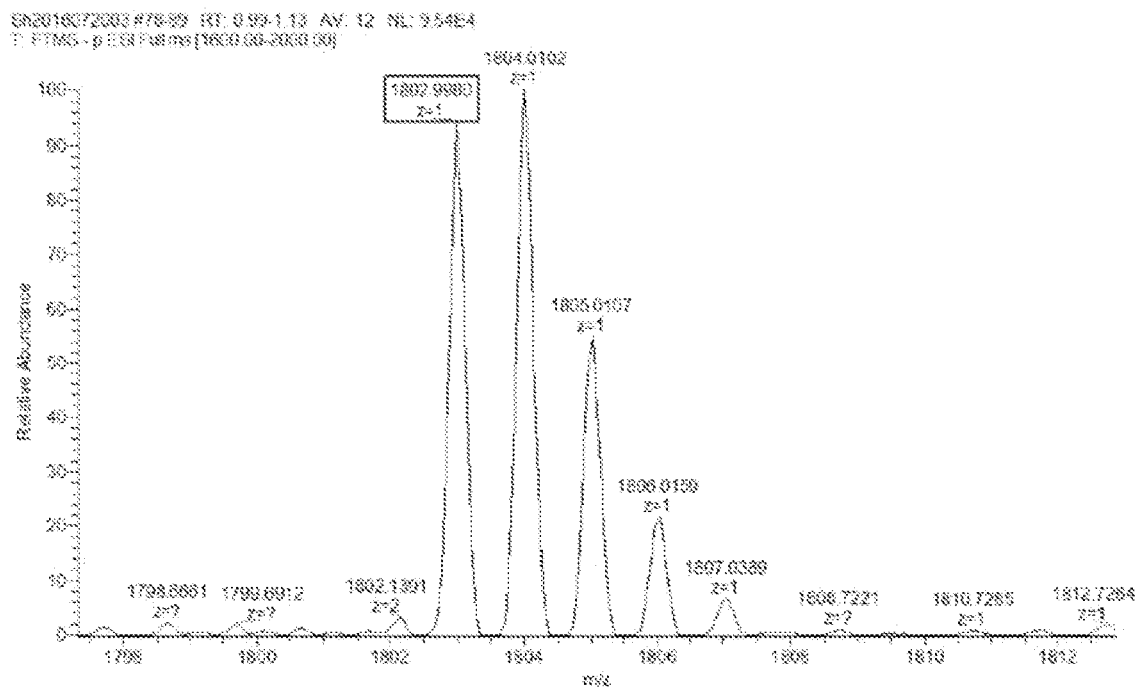

Globo H-Lipid 6:
$^1$H-NMR (600 MHz, CD$_3$OD) δ 5.23 (d, J=3.6 Hz, 1H), 4.94 (d, J=3.6 Hz, 1H), 4.54 (d, J=7.8 Hz, 2H), 4.41 (m, 1H), 4.28 (d, J=7.8 Hz, 1H), 4.26 (d, J=6.6 Hz, 1H), 4.23 (t, J=6 Hz, 1H), 4.14 (d, J=2.4 Hz, 1H), 4.08-4.06 (m, 2H), 3.99 (s, 1H), 3.93-3.66 (m, 23H), 3.60-3.43 (m, 15H), 3.42 (d, J=4.8 Hz, 1H), 3.39 (dt, J=9.6, 3.6 Hz, 1H), 3.26-3.22 (m, 2H), 3.19 (td, J=6.6, 1.8 Hz, 2H), 2.36 (d, J=4.2 Hz, 1H), 2.32 (s, 2H), 2.16 (s, 5H), 2.00 (s, 3H), 1.66-1.64 (m, 3H), 1.57-1.54 (m, 10H), 1.46-1.41 (m, 9H), 1.36-1.24 (m, 64H), 0.89 (t, J=7.2 Hz, 6H); $^{13}$C-NMR (125 MHz, CD$_3$OD) δ 174.4 (C), 174.3 (C), 174.0 (C),105.4 (CH), 105.2 (CH), 104.1 (CH), 103.7 (CH), 102.7 (CH), 100.9 (CH), 81.3 (CH), 80.4 (CH), 80.1 (CH), 79.0 (CH), 78.3 (CH), 78.1 (CH), 76.6 (CH), 76.29 (CH), 76.25 (CH), 76.2 (CH), 75.3 (CH), 74.7 (CH), 74.6 (CH), 73.3 (CH), 72.5 (CH), 72.4 (CH$_2$), 72.2 (CH$_2$), 71.4 (CH), 71.1 (CH$_2$), 70.6 (CH$_2$), 70.4 (CH), 70.2 (CH), 69.44 (CH), 69.40 (CH), 68.01 (CH), 62.54 (CH$_2$), 62.46 (CH$_2$), 61.9 (CH$_2$), 61.4 (CH$_2$), 52.9 (CH$_3$), 41.2 (CH$_2$), 40.2 (CH$_2$), 37.6 (CH$_2$), 37.4 (CH$_2$), 33.0 (CH$_2$), 31.1 (CH$_2$), 30.7 (CH$_2$), 30.6 (CH$_2$), 30.5 (CH$_2$), 30.4 (CH$_2$), 30.2 (CH$_2$), 30.1 (CH$_2$), 27.2 (CH$_2$), 26.9 (CH$_2$), 24.4 (CH$_2$), 23.6 (CH$_2$), 23.4 (CH$_3$), 22.5 (CH$_2$), 16.6 (CH$_3$), 14.5 (CH$_3$), HRMS (ESI, M−H−) calcd for C$_{88}$H$_{160}$N$_3$O$_{34}$ 1803.0883. found 1802.9980. The mass spectrum was showed at FIG. 5E.

The lipid chain 6 (1.2 eq) was dissolved in 1 mL of dry DMF with stirring. O-(7-Azabenzotriazole-1-yl)-N,N,N,N'-tetramethyluronium hexafluorophosphate (HATU, 1.2 eq) was added as a solid and stirred for 10 min at room temperature. Globo H-pentylamine (1.0 eq) was added and the resulting solution was stirred for 20 min before diisopropylethylamine (DIPEA, 5 eq) was added by syringe. The mixture was stirred for 16 hours at room temperature, and quenched by methanol. The mixture was concentrated and purified by LH-20 to yield the final product (62%).

Figure 5F:
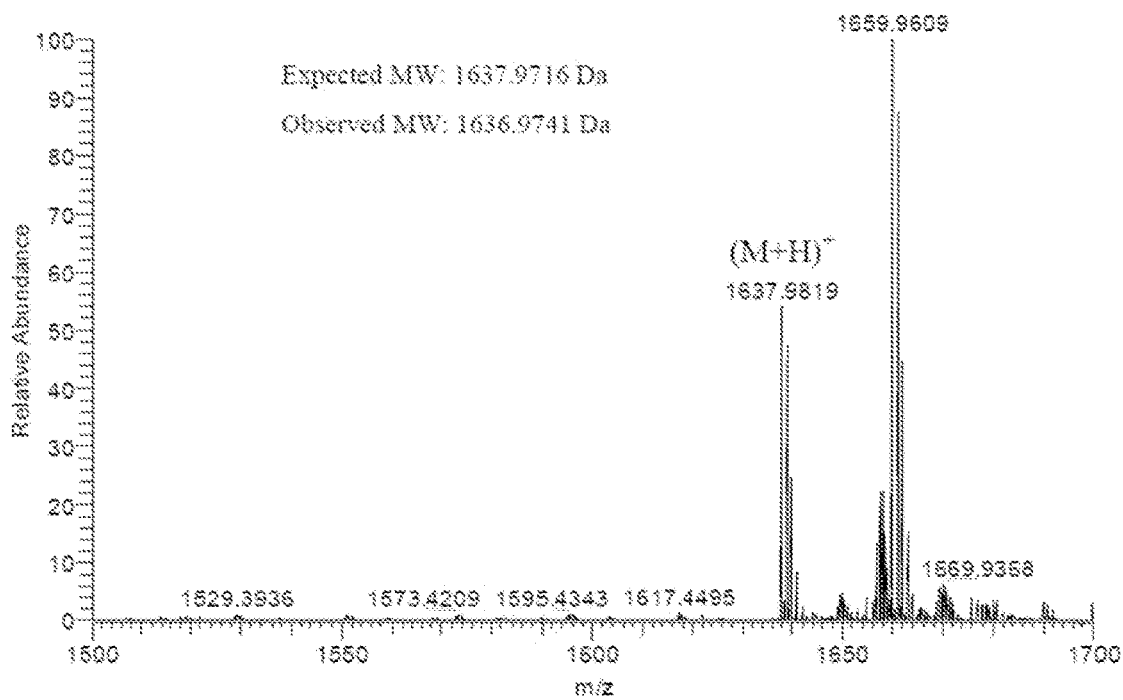

Globo H-Lipid 1 (Racemic):
$^1$H-NMR (600 MHz, CD$_3$OD/CDCl$_3$) δ 5.22 (d, J=3.9 Hz, 1H), 4.94 (d, J=3.7 Hz, 1H), 4.54 (d, J=7.8 Hz, 2H), 4.42-4.39 (m, 1H), 4.28-4.21 (m, 3H), 4.14 (d, J=1.8 Hz, 1H), 4.08-4.05 (m, 2H), 3.99 (s, 1H), 3.91-3.65 (m, 24H), 3.61-3.46 (m, 11H), 3.40-3.37 (m, 1H), 3.28-3.14 (m, 3H), 2.00 (s, 3H), 1.66-1.51 (m, 9H), 1.44-1.24 (m, 54H), 0.90-0.83 (m, 6H); $^{13}$C-NMR (150 MHz, CD$_3$OD/CDCl$_3$) δ 174.5 (C), 173.1 (C), 105.5 (CH), 105.3 (CH), 104.2 (CH), 103.8 (CH), 102.9 (CH), 101.1 (CH), 81.7 (CH), 81.5 (CH), 80.6 (CH), 80.3 (CH), 78.4 (CH), 76.7 (CH), 76.4 (CH), 76.35 (CH), 76.3 (CH), 75.4 (CH), 74.8 (CH), 74.7 (CH), 73.5 (CH), 72.7 (CH$_2$), 72.6 (CH), 72.5 (CH), 72.2 (CH$_2$), 71.5 (CH), 70.8 (CH$_2$), 70.7 (CH), 70.5 (CH), 70.4 (CH), 69.6 (CH), 69.5 (CH), 68.2 (CH), 62.7 (CH$_2$), 62.6 (CH$_2$), 62.56 (CH$_2$), 62.0 (CH$_2$), 61.6 (CH$_2$), 53.1 (CH), 40.5 (CH$_2$), 40.0 (CH$_2$), 33.1 (CH$_2$), 30.8 (CH$_2$), 30.78 (CH$_2$), 30.73 (CH$_2$), 30.6 (CH$_2$), 30.57 (CH$_2$), 30.5 (CH$_2$), 30.34 (CH$_2$), 30.3 (CH$_2$), 27.3 (CH$_2$), 27.2 (CH$_2$), 24.4 (CH$_2$), 24.35 (CH$_2$), 23.8 (CH$_2$), 23.6 (CH$_3$), 16.8 (CH$_3$), 14.6 (CH$_3$); FIRMS (ESI, M+H+) calcd for C$_{78}$H$_{145}$N$_2$O$_{33}$ 1637.9730. found 1637.9819. The mass spectrum was showed at FIG. 5F.

Lipid 1(racemic) (1.2 eq) was dissolved in 1 mL of dry DMF with stirring. O-(7-Azabenzotriazole-1-yl)-N,N,N,N'-tetramethyluronium hexafluorophosphate (HATU, 1.2 eq) was added as a solid and stirred for 10 min at room temperature. Globo H-pentylamine (1.0 eq) was added and the resulting solution was stirred for 20 min before diisopropylethylamine (DIPEA, 5 eq) was added by syringe. The mixture was stirred for 16 hours at room temperature, and quenched by methanol. The mixture was concentrated and purified by LH-20 to yield the final product (61%).

Figure 6A:
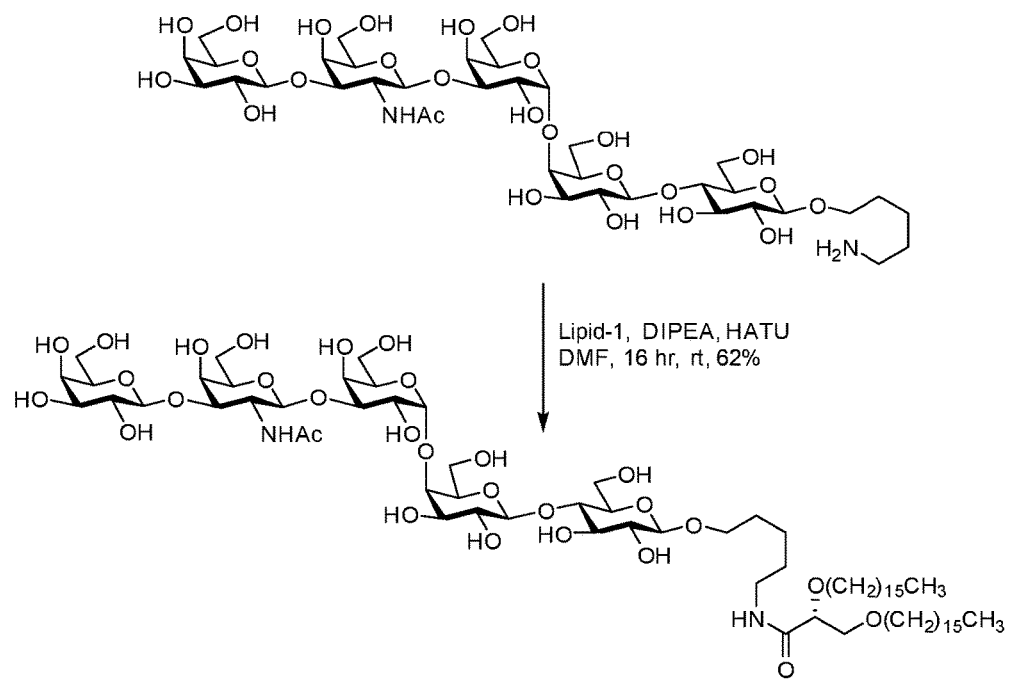
FIG. 6A and FIG. 6B. The coupling reaction of SSEA-3-NH$_2$ and lipid chain products.
Figure 6B:
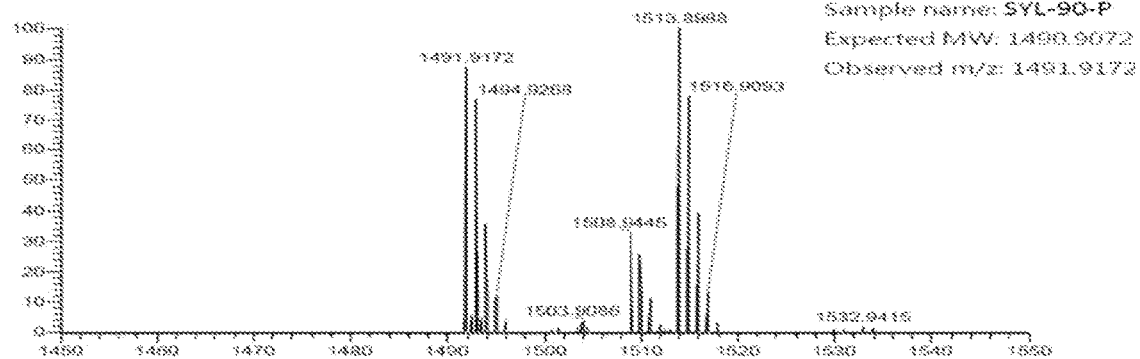

Coupling of SSEA-3-NH$_2$ and Lipid Chain Product Afforded the New Composition Via the Amide Bond Formation:

SSEA-3-Lipid 1:
$^1$H-NMR (600 MHz, CD$_3$OD/CDCl$_3$) δ 4.95 (d, J=4.0 Hz, 1H), 4.70 (d, J=8.4 Hz, 1H), 4.42-4.40 (m, 1H), 4.33 (d, J=7.6 Hz, 1H), 4.28 (d, J=7.8 Hz, 1H), 4.24-4.22 (m, 1H), 4.16 (d, J=2.4 Hz, 1H), 4.10 (d, J=2.8 Hz, 1H), 4.05 (dd, J=10.7 Hz, J=8.5 Hz, 1H), 3.99 (s, 1H), 3.94 (dd, J=10.2 Hz, J=3.9 Hz, 1H), 3.90-3.85 (m, 4H), 3.84-3.66 (m, 12H), 3.61-3.42 (m, 13H), 3.38 (td, J=9.5 Hz, J=3.3 Hz, 1H), 3.28-3.19 (m, 2H), 1.98 (s, 3H), 1.68-1.61 (m, 4H), 1.59-1.52 (m, 4H), 1.44-1.28 (m, 58H), 0.89 (t, 6H, J=7.0 Hz); $^{13}$C-NMR (150 MHz, CD$_3$OD/CDCl$_3$) δ 174.9 (C), 172.9 (C), 106.4 (CH), 105.3 (CH), 104.1 (CH), 104.0 (CH), 102.7 (CH), 81.6 (CH), 81.4 (CH), 81.3 (CH), 80.7 (CH), 80.1 (CH), 76.6 (CH), 76.3 (CH), 76.2 (CH), 76.17 (CH), 76.1 (CH), 74.6 (CH), 74.5 (CH), 74.4 (CH), 72.6 (CH), 72.4 (CH), 72.3 (CH), 72.1 (CH$_2$), 70.6 (CH$_2$), 70.4 (CH), 70.1 (CH), 69.3 (CH), 69.2 (CH), 62.6 (CH$_2$), 62.5 (CH$_2$), 62.45 (CH$_2$), 61.9 (CH$_2$), 61.4 (CH$_2$), 53.3 (CH), 39.9 (CH$_2$), 32.9 (CH$_2$), 30.7 (CH$_2$), 30.6 (CH$_2$), 30.58 (CH$_2$), 30.5 (CH$_2$), 30.4 (CH$_2$), 30.3 (CH$_2$), 30.2 (CH$_2$), 30.15 (CH$_2$), 27.1 (CH$_2$), 27.07 (CH$_2$), 24.2 (CH$_2$), 23.6 (CH$_2$), 23.3 (CH$_3$), 14.4 (CH$_3$); FIRMS (ESI, MH+) calcd for C$_{72}$H$_{135}$N$_2$O$_{29}$ 1491.9151. found 1491.9172. The mass spectrum was showed at FIG. 6B.

The lipid chain 1 (1.2 eq) was dissolved in 1 mL of dry DMF with stirring. O-(7-Azabenzotriazole-1-yl)-N,N,N,N'-tetramethyluronium hexafluorophosphate (HATU, 1.2 eq) was added as a solid and stirred for 10 min at room temperature. SSEA3-pentylamine (1.0 eq) was added and the resulting solution was stirred for 20 min before diisopropylethylamine (DIPEA, 5 eq) was added by syringe. The mixture was stirred for 16 hours at room temperature, and quenched by methanol. The mixture was concentrated and purified by LH-20 to yield the final product (62%).

Coupling of SSEA-4-NH$_2$ and Lipid Chain Product Afforded the New Composition Via the Amide Bond Formation:

SSEA-4-Lipid 1:
$^1$H-NMR (600 MHz, CD$_3$OD/CDCl$_3$) δ 4.94 (d, J=3.9 Hz, 1H), 4.71 (d, J=8.4 Hz, 1H), 4.55 (s, 1H, N—H), 4.43-4.40 (m, 2H), 4.29 (d, J=7.9 Hz, 1H), 4.25-4.23 (m, 1H), 4.16 (d, J=2.5 Hz, 1H), 4.11 (d, J=2.9 Hz, 1H), 4.06-3.99 (m, 3H), 3.94 (dd, J=10.2 Hz, J=3.9 Hz, 1H), 3.91-3.81 (m, 10H), 3.81-3.64 (m, 12H), 3.63-3.44 (m, 15H), 3.39 (td, J=9.3 Hz, J=3.2 Hz, 1H), 3.28-3.18 (m, 4H), 2.86 (dd, J=12.3 Hz, J=3.7 Hz, 1H, H-3Fee), 2.01 (s, 3H, NHAc), 2.00 (s, 3H, NHAc), 1.74-1.70 (m, 1H), 1.68-1.60 (m, 4H), 1.58-1.52 (m, 4H), 1.44-1.22 (m, 64H), 0.90 (t, J=7.1 Hz, 6H); $^{13}$C-NMR (150 MHz, CD$_3$OD/CDCl$_3$) δ 175.4 (C), 175.0 (C), 174.9 (C), 173.0 (C), 106.2 (CH), 105.4 (CH), 104.3 (CH), 104.1 (CH), 102.7 (CH), 100.8 (C), 81.7 (CH), 81.4 (CH), 81.1 (CH), 80.5 (CH), 80.1 (CH), 77.6 (CH), 76.6 (CH), 76.4 (CH), 76.3 (CH), 76.2 (CH), 74.8 (CH), 74.7 (CH), 74.6 (CH), 72.8 (CH), 72.6 (CH2), 72.5 (CH), 72.47 (CH), 72.4

Figure 7A:
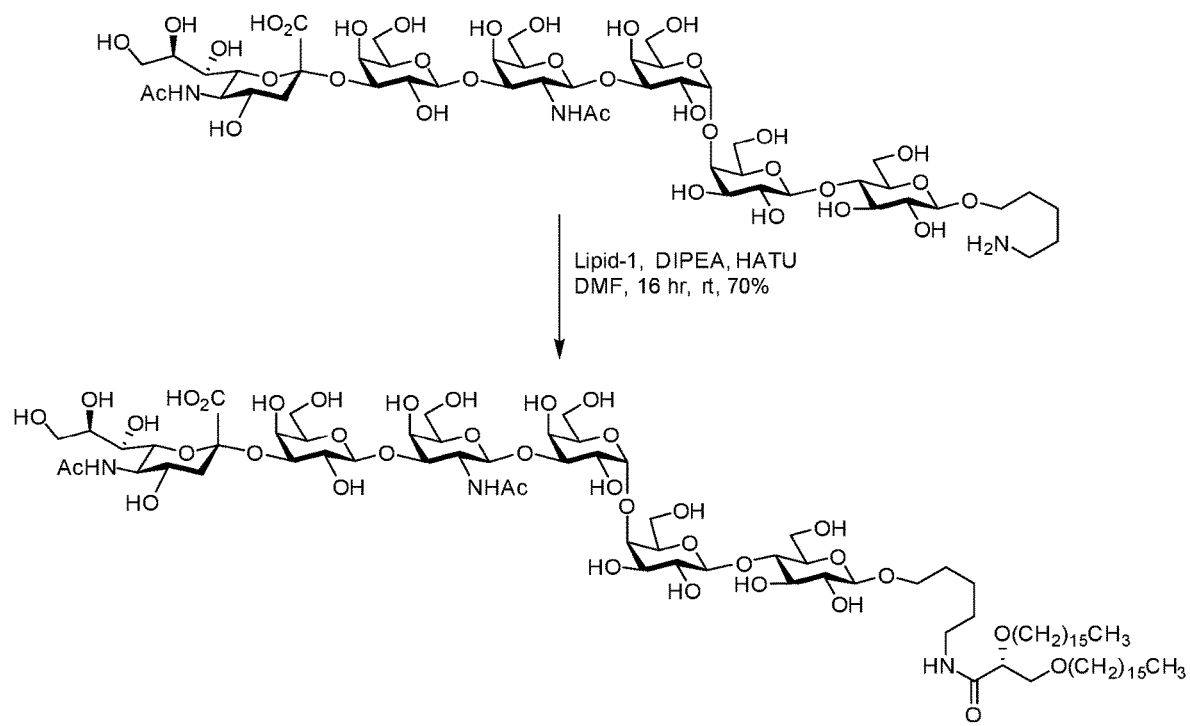
FIG. 7A and FIG. 7B. The coupling reaction of SSEA-4-NH₂ and lipid chain products.
Figure 7B:
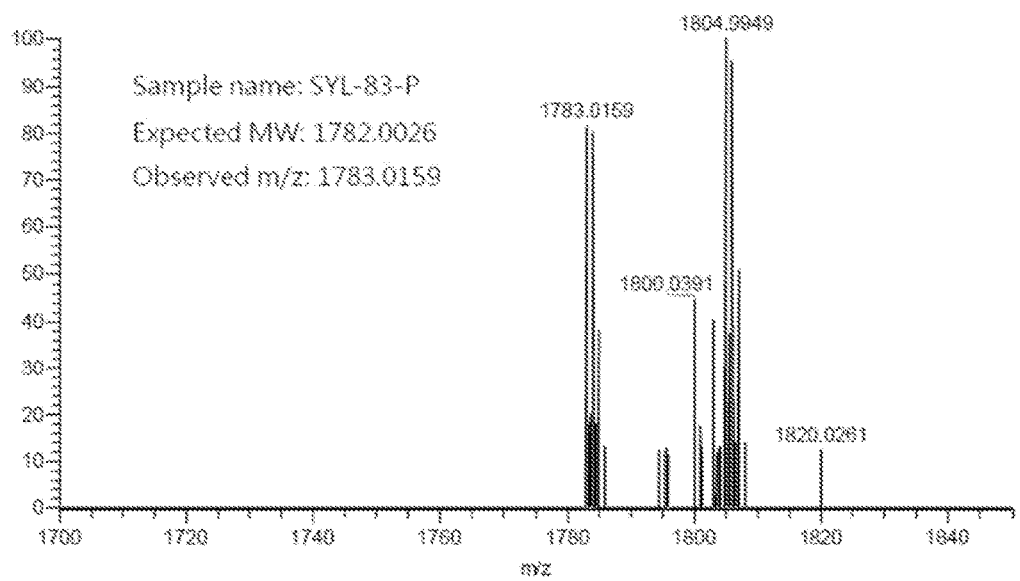

($CH_2$), 72.1 ($CH_2$), 70.6 ($CH_2$), 70.59 (CH), 70.5 (CH), 69.9 (CH), 69.4 (CH), 69.3 (CH), 69.2 (CH), 68.8 (CH), 64.5 ($CH_2$), 62.8 ($CH_2$), 62.63 ($CH_2$), 62.6 ($CH_2$), 61.9 ($CH_2$), 61.4 ($CH_2$), 55.6 (CH), 53.8 (CH), 53.1 (CH), 43.6 ($CH_2$), 42.1 ($CH_2$), 39.9 ($CH_2$), 33.0 ($CH_2$), 30.7 ($CH_2$), 30.69 ($CH_2$), 30.5 ($CH_2$), 30.49 ($CH_2$), 30.4 ($CH_2$), 30.3 ($CH_2$), 30.2 ($CH_2$), 27.2 ($CH_2$), 27.1 ($CH_2$), 24.3 (CH), 23.7 (CH, $CH_2$), 23.5 ($CH_3$), 22.6 ($CH_3$), 14.5 ($CH_3$); HRMS (ESI, MH+) calcd for $C_{83}H_{152}N_3O_{37}$ 1783.0105. found 1783.0159. The mass spectrum was showed at FIG. 7B.

The lipid chain 1 (1.2 eq) was dissolved in 1 mL of dry DMF with stirring. O-(7-Azabenzotriazole-1-yl)-N,N,N,N'-tetramethyluronium hexafluorophosphate (HATU, 1.2 eq) was added as a solid and stirred for 10 min at room temperature. SSEA4-pentylamine (1.0 eq) was added and the resulting solution was stirred for 20 min before diisopropylethylamine (DIPEA, 5 eq) was added by syringe. The mixture was stirred for 16 hours at room temperature, and quenched by methanol. The mixture was concentrated and purified by LH-20 to yield the final product (70%).

Example 2

ELISA Analysis Using Globo H-Ceramide and Globo H-Lipids

Enzyme-linked immunosorbent assay. Clear Flat-Bottom Immuno Nonsterile 96-Well Plates (Thermo Fisher Scientific Inc., Cat#442404)) were coated with the respective glycan-linked glycopeptides at 0.2 µg to 50 µL ethanol per well and were incubated at room temperature overnight. Then 100 µL Casein Blocking Buffer (Sigma-Aldrich Co. LLC, Cat#B6429) was added to each well and the microtiter plate was incubated at room temperature for 30 minutes. All subsequent steps were performed at room temperature.

The microtiter plate was treated with 50 µL of different dilutions of VK9 cells in Casein Blocking Buffer to each well and incubated at room temperature for 1 hr. The wells were then washed three times with Phosphate-buffered saline (Thermo Fisher Scientific Inc., Cat#70011) plus 0.05% (vol/vol) Tween 20 (J. T. Baker, Cat#JTB-X251-07) using a microplate washer (SkanWash 400, Molecular Devices LLC.). At this point, 50 µL of Secondary Antibody Solution (alkaline phosphatase-conjugated goat anti-mouse IgG antibody (Southern Biotech Associates, Inc., Cat#1030-04) diluted 1:1000 in Casein Blocking Buffer) was added into each well and incubated at room temperature for 45 minutes. The wells were then washed three times with Phosphate-buffered saline plus 0.05% (vol/vol) Tween 20.

The microtiter plate was treated with 100 µL of Alkaline Phosphatase (pNPP) Yellow Liquid Substrate System for ELISA (Sigma-Aldrich Co. LLC., Cat#P7998) at 37° C. for 20 minutes and the reaction was stopped by adding another 50 µL of Stop Solution (3N NaOH). The bound VK9 cells were visualized monitored at 405 nm using a microplate reader (SpectraMax M2, Molecular Devices LLC.).

Figure 8A:
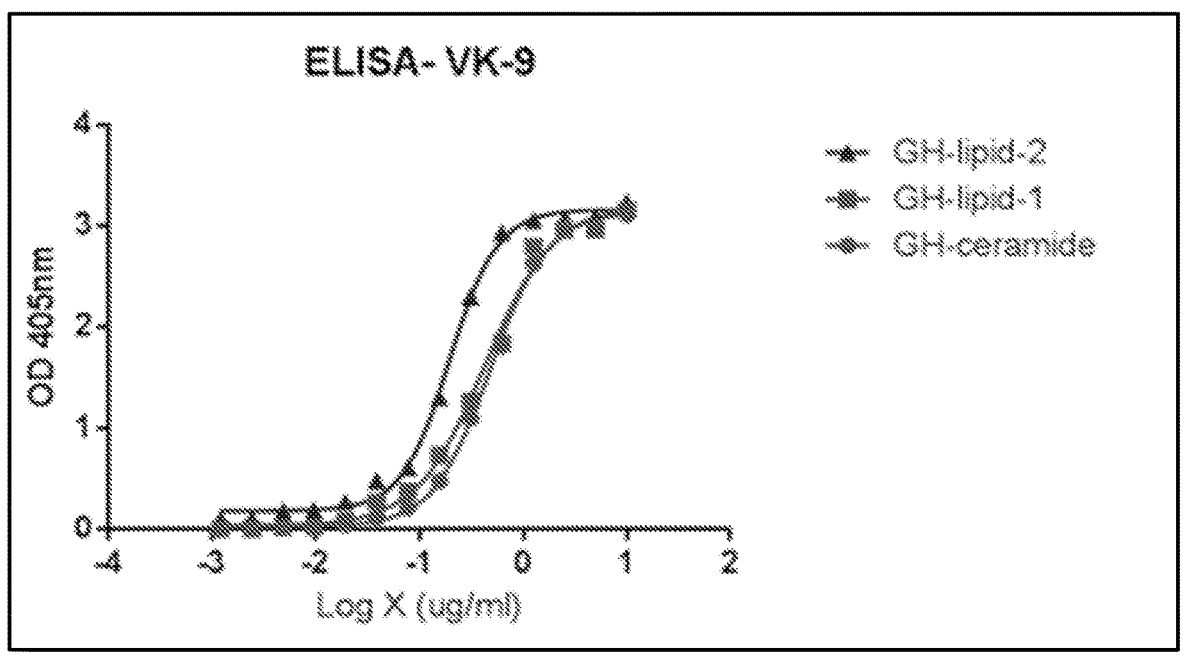
FIG. 8A and FIG. 8B. The comparison of ELISA analysis between Globo H-ceramide and Globo H-lipids.
Figure 8B:
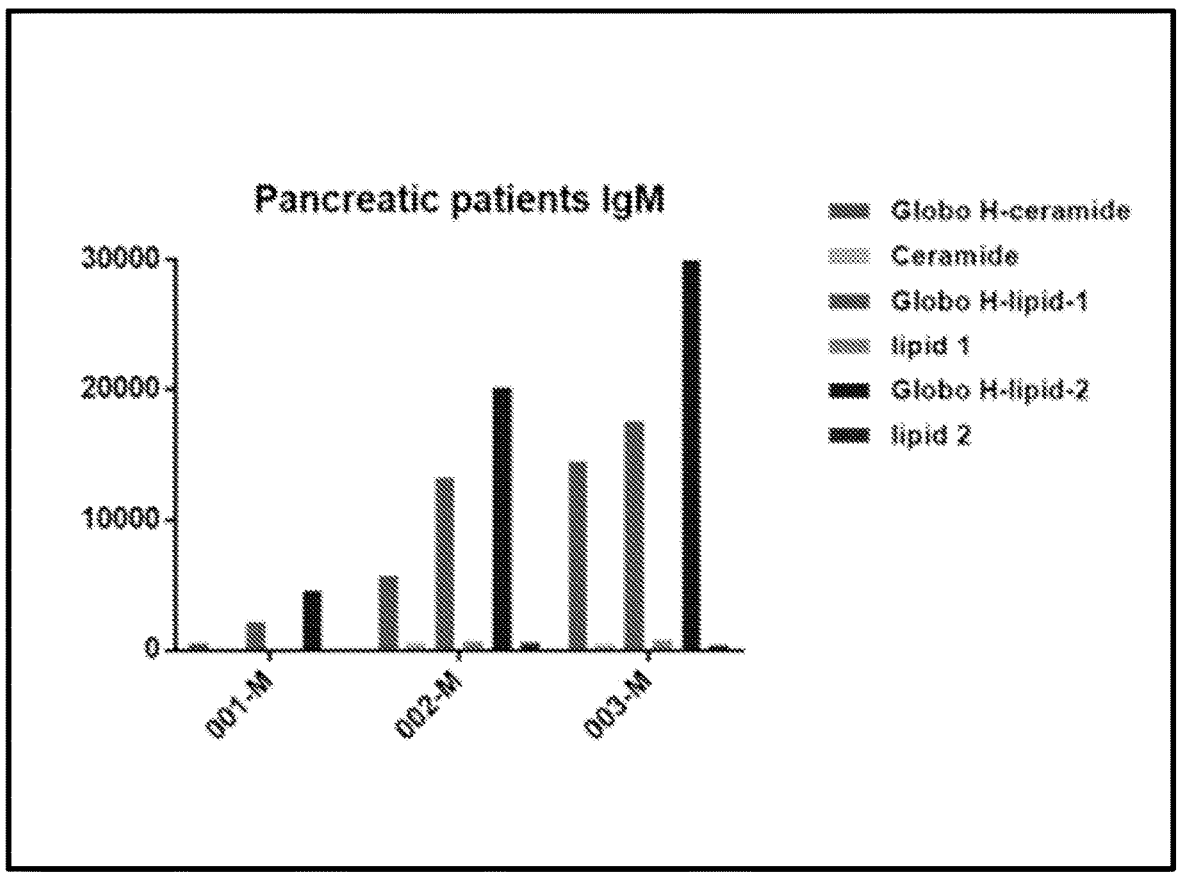

The comparison of binding patterns of Globo H-ceramide and Globo H-lipids was listed in FIG. 8A. The Globo H lipid 1, Globo H lipid 2, and Globo H-ceramide were immobilized on microtiter plate from 0.001 to 10 µg/mL, separately. The optical density at 405 nm ($OD_{405}$) of Globo H-lipid 2 is higher than Globo H-ceramide. In addition, the comparison of IgM binding patterns of Globo H-ceramide, Globo H-lipid 1, and Globo H-lipid 2 using sugar array was listed in FIG. 8B. It indicated that the IgM binding efficacy with pancreatic patient clinical samples of Globo H lipid linker is higher than Globo H ceramide. Finally, the comparison of glycan-linked surfaces in the detection of pancreatic cancer was listed in Table 1. It indicated that there was a better resolution to differentiate between positive and negative clinical samples using different glycans (Globo H, SSEA-3, SSEA-4, Gb3, Gb4, $Le^y$, $Le^x$, $SLe^a$, and $SLe^x$) linked surfaces. In some embodiments the complex binding agent may comprise any of the complex binding agents or detectable labels of this disclosure. In certain exemplary embodiments, the Globo H ceramide and Globo H lipids are the array elements and the IgM antibodies are from the sample. And then secondary labeled anti-human ab are used to detect the complexes

TABLE 1

Comparison of Glycan-linked surfaces in the detection of Pancreatic Cancer

| | Mean (IgM) | | |
| --- | --- | --- | --- |
| Sugar markers | Pancreatic cancer (n = 115) | Healthy (n = 100) | P value |
| Globo H-Ceramide | 3130.03 | 1977.88 | 0.03* |
| SSEA3-Ceramide | 7145.10 | 2735.54 | <0.001** |
| SSEA4-Biotin | 826.88 | 256.95 | <0.001** |
| $Le^y$-Biotin | 3268.62 | 836.74 | 0.003** |
| $SLe^a$-Biotin | 4863.02 | 920.68 | <0.001** |
| $SLe^x$-Biotin | 1622.94 | 520.16 | 0.03* |

Example 3

Glycan Array Analysis Using Globo H-Ceramide and Globo H-Lipids

This testing platform utilized Agnitio BioIC system which performed an automatically ELISA reaction within a microfluidic cartridge. Each cartridge contained an array of microfluidic pumps and valves, a channel network, reagent storage reservoirs, a glycan array reaction zone, and a waste storage reservoir. To perform the test, all reagent and test sample were pumped sequentially, from their respected reservoirs in to a reaction zone containing the glycan microarray in order to carry out a multiplexed ELISA reaction with chemical luminescence. The result data was captured simultaneously and data analysis was performed by the LabIT software provided by Agnitio Science and Technology Inc. The specification of equipment list of Agnitio BioIC system is listed in Table 2.

TABLE 2

Equipment list of OBI-868 Agnitio BioIC system

| No. | Equipment Name | Module | Purpose/Remark |
| --- | --- | --- | --- |
| 1. | Agnitio BioIC Analyzer | BA-G2000 | Chemical luminescence detector with CCD camera, microarray image capture |
| 2. | Agnitio BioIC Pumping Machine | BA-G2000 pumping machine | Microfluidic cartridge reagent pumping machine |
| 3. | Computer | NA | Performing multiple ELISA procedures and data Processing using LabIT software |
| 4. | Barcode Reader | NA | Testing cartridge ID uploading |

Figure 9:
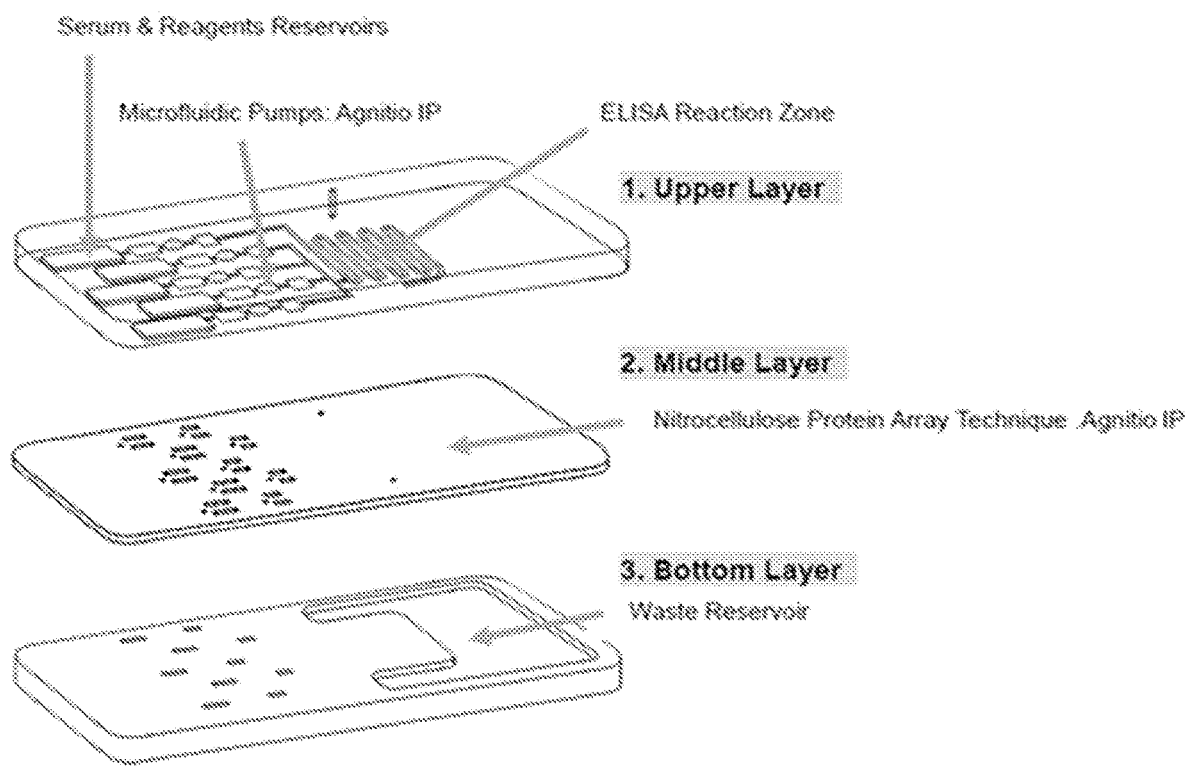
FIG. 9. The exemplary component layers of an exemplary microfluidic cartridge.

The Microfluidic cartridge was manufactured at Agnitio Science and Technology Inc. The microfluidic cartridge was composed by three layers shown in FIG. 9. The upper layer contained serum and reagents reservoirs, microfluidic pumps, and ELISA channel network. The rubber middle layer contained a coated nitrocellulose membrane. The glycan antigens (Globo H-ceramide and Globo H-lipid 1) were immobilized onto the nitrocellulose membrane via hydrophobic interactions. The bottom layer contained a tank as for the waste reservoir. There were one hundred and twenty spots for original array layout design. In order to ensure the spot-to-spot coefficient of variation (CV) was lower than 15%, we only used central sixty-four spots for following clinical sample test.

Glycan Array Analysis (Primary Test)

Reagent preparation: Sixty-six microliter Normal Human Serum (NETS) or pancreatic cancer patient's serum was added in 594 µL Sample Diluent Buffer (BioCheck Inc., Cat#MB 10175) to form ten-fold dilution. The Secondary Antibody Solution was performed by first adding 2 µL Horseradish peroxidase (HRP)-conjugated goat anti-human IgG (KPL Inc., Cat#474-1002)/IgM (KPL Inc., Cat#474-1003) in 98 µL Conjugate Buffer (SuperBlock (TBS) Blocking Buffer plus 0.2% Tween 20, Thermo Fisher Scientific Inc., Cat#37535) to form fifty-fold dilution. Next, 40 µL diluted solution was pumped into 2360 µL Conjugate Buffer to form the Secondary Antibody Solution (3000× diluted).

Assay procedure: Six hundred and twenty microliter Wash Buffer (Phosphate-buffered saline (Thermo Fisher Scientific Inc., Cat#70011) plus 0.2% (vol/vol) Tween 20 (J. T. Baker, Cat#JTB-X251-07)) was added in the "Wash" hole of array. Next, 120 µL Blocking Buffer (Protein-Free Blocking Buffers, Thermo Fisher Scientific Inc., Cat#37571) was added in the "Blocking" hole of array. At this point, 120 µL Secondary Antibody Solution and 100 serum were added in the "Conjugate" and "Serum" hole of array, separately. At the last, 120 Substrate Buffer (SuperSignal ELISA Femto Maximum Sensitivity Substrate, Thermo Fisher Scientific Inc., Cat#37074) was added in the "Substrate" hole of array in ten minutes.

The glycan array was put on the Agnitio BioIC Pumping Machine for pressurizing 30 minutes. The bound serum was visualized monitored using Agnitio BioIC Analyzer. The absorbance intensity of array was converted into "Glycan Scores" based on the following calculation: In certain examples, glycan scores=(raw data−background)/Internal Control×10.

The Internal Control was performed using 0.5 µM Secondary Antibody Solution only. The glycan score system was defined as the integral numbers from 0, 1, 2 . . . to 20. If the converted score is higher than 20, it's scoring will be defined as 20.

Figure 10A:
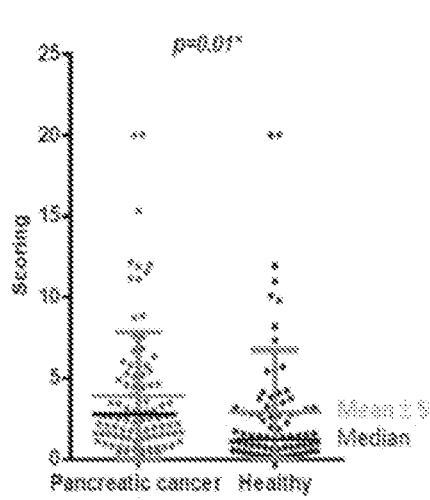
FIG. 10A, FIG. 10B, FIG. 10C, FIG. 10D, FIG. 10E. Comparison of Human IgM/IgG glycan scores of glycan-ceramide and glycan-lipid.
Figure 10B:
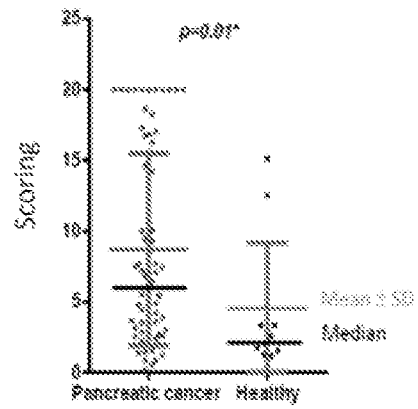
Figure 10C:
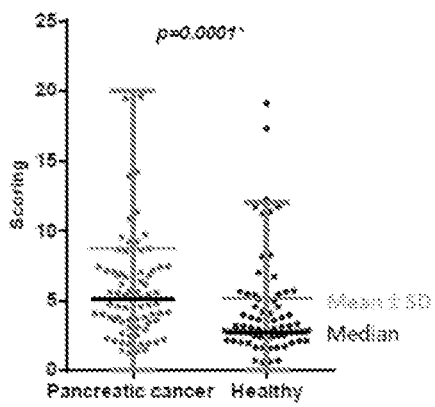
Figure 10D:
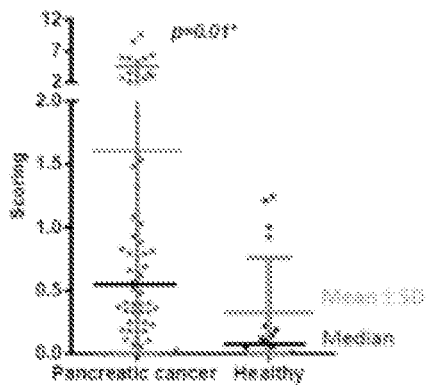
Figure 10E:
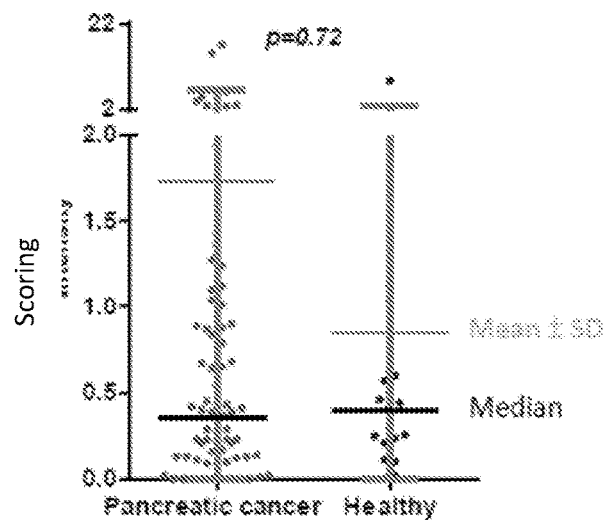

Glycan score of Human IgM: There were total 175 clinical samples (98 pancreatic cancer and 77 healthy serum) performed using Globo H-ceramide and SSEA-3-ceramide immobilized arrays. In addition, another 91 clinical samples (76 pancreatic cancer and 15 healthy serum) were performed using Globo H-lipid 1 immobilized arrays. The comparison of binding patterns of glycan-ceramide and glycan-lipid were listed in FIG. 10. The median values of Globo H-ceramide IgM test were 2.53 (pancreatic cancer) and 1.57 (healthy) [FIG. 10A]. It seemed that there was only a little difference between positive and negative clinical samples. However, the median values of Globo H-lipid 1 IgM test were 6.64 (pancreatic cancer) and 2.56 (healthy) [FIG. 10B]. It indicated that there was a better resolution to differentiate between positive and negative clinical samples. In addition, the binding efficacy of an exemplary linker/array in a SSEA-3-ceramide IgM was listed in FIG. 10C. The median values of SSEA-3-ceramide IgM test were 5.66 (pancreatic cancer) and 3.17 (healthy).

Glycan score of Human IgG: There were total 93 clinical samples (74 pancreatic cancer and 19 healthy serum) were performed using Globo H-lipid 1 and SSEA-4-lipid 1 immobilized arrays. The binding efficacy of an exemplary linker/array in a Globo H-lipid 1 IgG was listed in FIG. 10D. The median values of Globo H-lipid 1 IgG test are 0.54 (pancreatic cancer) and 0.12 (healthy). In addition, the binding efficacy of an exemplary linker/array in a SSEA-4-lipid 1 IgG was listed in FIG. 10E. It indicated that Globo H-lipid was an effective diagnostic marker to differentiate between positive and negative clinical samples.

Moreover, the sensitivity, specificity, and accuracy calculations using SPSS statistical software under the methodology of logistic regression & ROC were listed in Table 3 (one marker assay), Table 4 (two markers assay) and Table 5 (three markers assay). These results indicated that Globo H, SSEA-3 and SSEA-4 could serve as good diagnostic biomarkers for pancreatic cancer.

TABLE 3

Comparison the sensitivity, specificity, and accuracy of glycan-linked surfaces in the detection of pancreatic cancer (one marker)

| Predict markers | Cut-off value | Sensitivity (%) | Specificity (%) | Accuracy (%) |
|---|---|---|---|---|
| Globo H-ceramide IgM | 1.08 | 83.7 | 40.3 | 64.6 |
| Globo H-lipid 1 IgM | 3.41 | 71.1 | 73.3 | 72.0 |
| Globo H-lipid 1 IgG | 0.23 | 71.6 | 68.4 | 71.0 |
| SSEA3-ceramide IgM | 3.59 | 79.6 | 55.8 | 69.1 |
| SSEA4-lipid 1 IgG | 0.64 | 41.9 | 84.2 | 50.5 |

TABLE 4

Comparison the sensitivity, specificity, and accuracy of glycan-linked surfaces in the detection of pancreatic cancer (two markers)

| Predict markers | Cut-off value | Sensitivity (%) | Specificity (%) | Accuracy (%) |
|---|---|---|---|---|
| GHC(IgM) + GHL(IgM) | 4.23 | 81.6 | 66.7 | 79.1 |
| GHC(IgM) + SSEA3C(IgM) | 7.97 | 62.2 | 72.2 | 63.7 |
| GHL(IgM) + SSEA3C(IgM) | 6.54 | 81.6 | 53.3 | 76.9 |
| GHL(IgG) + SSEA4L(IgG) | 0.74 | 60.8 | 68.4 | 62.4 |
| GHC(IgM) + GHL(IgG) | 1.51 | 90.9 | 52.6 | 81.1 |
| GHC(IgM) + SSEA4L(IgG) | 2.03 | 80.0 | 57.9 | 74.3 |
| GHL(IgM) + GHL(IgG) | 3.03 | 83.6 | 57.1 | 77.0 |
| GHL(IgM) + SSEA4L(IgG) | 3.56 | 72.7 | 57.1 | 68.9 |
| SSEA3C(IgM) + GHL(IgG) | 3.84 | 81.8 | 52.6 | 74.3 |
| SSEA3C(IgM) + SSEA4L(IgG) | 4.28 | 80.0 | 52.6 | 72.9 |

*GHC: Globo H-ceramide/GHL: Globo H-lipid 1/SSEA3C: SSEA3-ceramide/SSEA4L: SSEA4-lipid 1

TABLE 5

Comparison the sensitivity, specificity, and accuracy of glycan-linked surfaces in the detection of pancreatic cancer (three markers)

| Predict markers | Cut-off value | Sensitivity (%) | Specificity (%) | Accuracy (%) |
|---|---|---|---|---|
| GHC + GHL + SSEA3C(IgM) | 9.71 | 76.3 | 66.7 | 74.7 |
| GHC(IgM) + GHL(IgM) + GHL(IgG) | 4.02 | 89.1 | 57.1 | 82.6 |
| GHC(IgM) + GHL(IgM) + SSEA4L(IgG) | 4.43 | 83.6 | 50.0 | 76.8 |
| GHC(IgM) + SSEA3C(IgM) + GHL(IgG) | 6.07 | 83.6 | 57.9 | 77.0 |
| GHC(IgM) + SSEA3C(IgM) + SSEA4L(IgG) | 5.56 | 87.3 | 47.4 | 77.0 |

TABLE 5-continued

Comparison the sensitivity, specificity, and accuracy of glycan-linked surfaces in the detection of pancreatic cancer (three markers)

| Predict markers | Cut-off value | Sensitivity (%) | Specificity (%) | Accuracy (%) |
| --- | --- | --- | --- | --- |
| GHL(IgM) + SSEA3C(IgM) + GHL(IgG) | 7.03 | 83.6 | 57.1 | 78.3 |
| GHL(IgM) + SSEA3C(IgM) + SSEA4L(IgG) | 6.70 | 85.5 | 50.0 | 78.3 |
| GHL(IgG) + SSEA3C(IgM) + SSEA4L(IgG) | 4.32 | 81.8 | 526 | 74.3 |

*GHC: Globo H-ceramide/GHL: Globo H-lipid 1/SSEA3C: SSEA3-ceramide/SSEA4L: SSEA4-lipid 1

Glycan Array Analysis (Secondary Test)

The reagents, equipment and assay procedures were totally the same as primary test. However, the intensity of array was converted into "Ab level (µg/mL)" based on following calculation which is relative to Anti-human Globo H IgG.

The internal curve of each chip was using linear regression to calculate slope and intercept. In certain examples, the Ab level (µg/mL)=[(raw data-intercept)/slope]×0.1. The internal curve was performed using 0.0625, 0.125, 0.25, 0.5, 0.75, and 1 µg/mL of human IgM.

(1) Pancreatic Cancer

Figure 11A:
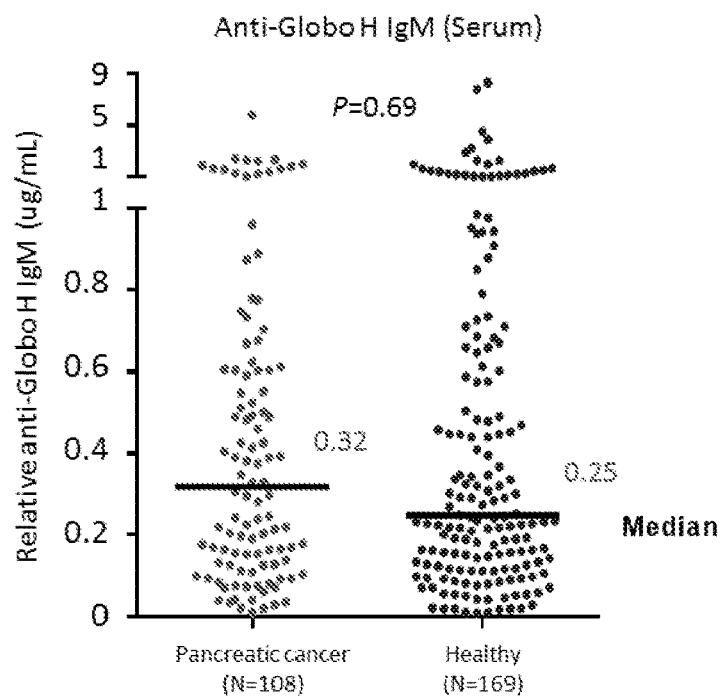
FIG. 11A, FIG. 11B, FIG. 11C, and FIG. 11D. Comparison of Human IgM level of glycan-lipid using pancreatic cancer clinical samples.
Figure 11B:
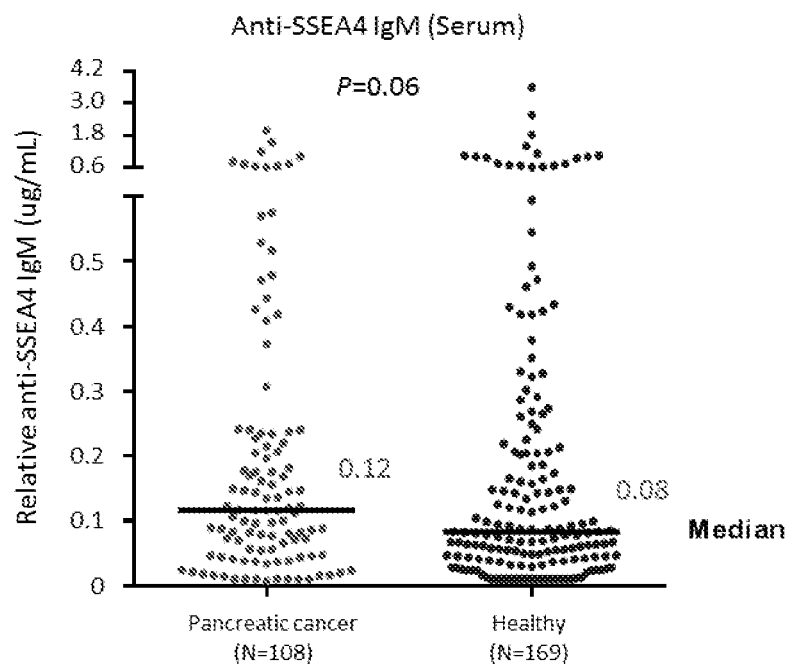
Figure 11C:
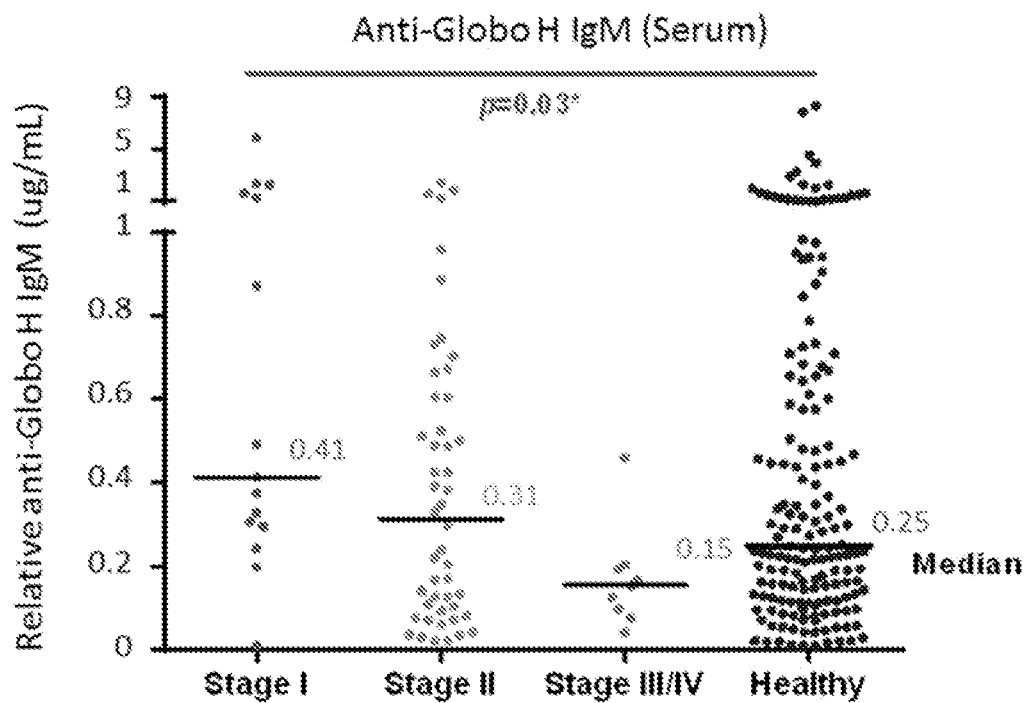
Figure 11D:
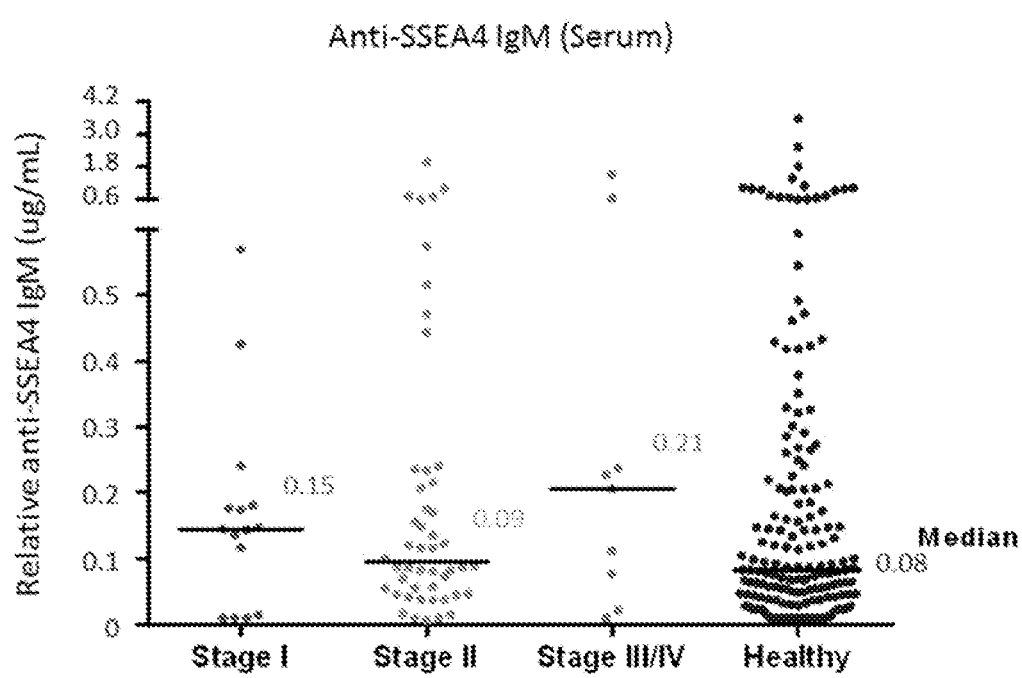

Relative Anti-glycan Human IgM: There were total 277 clinical samples (108 pancreatic cancer and 169 healthy serum) performed using Globo H-lipid 1 and SSEA-4-lipid 1 immobilized arrays. The binding patterns of IgM from the sample to the glycan-lipids of the array were reported in FIG. 11. The median values of Globo H-lipid 1 IgM test were 0.32 (pancreatic cancer) and 0.25 (healthy) [FIG. 11A]. The median values of SSEA-4-lipid 1 IgM test were 0.12 (pancreatic cancer) and 0.08 (healthy) [FIG. 11B]. In addition, both Globo H-lipid 1 (FIG. 11C) and SSEA-4-lipid 1 (FIG. 11D) immobilized arrays could detect Stage I and Stage II pancreatic cancers.

(2) Lung Cancer

Figure 12A:
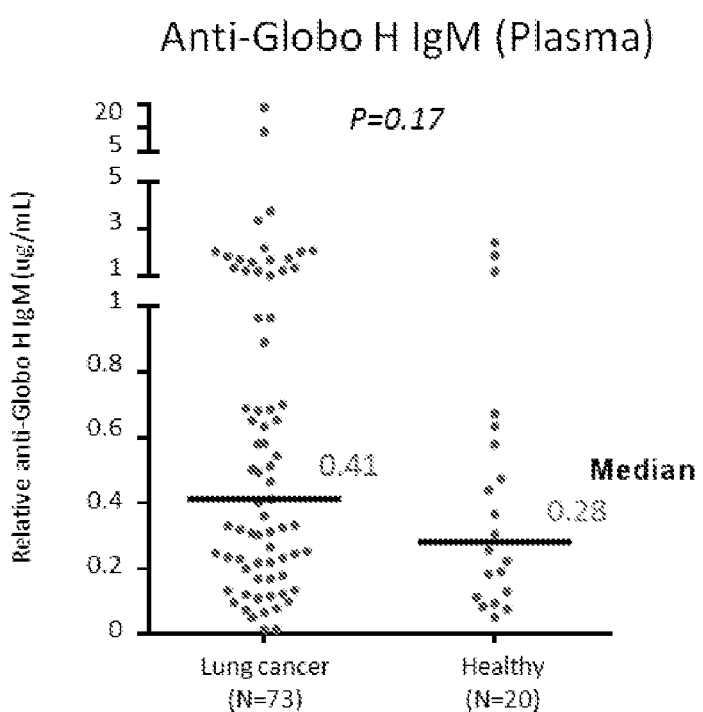
FIG. 12A, FIG. 12B, FIG. 12C, FIG. 12D, FIG. 12E and FIG. 12F. Comparison of Human IgM level of glycan-lipid using lung cancer clinical samples.
Figure 12B:
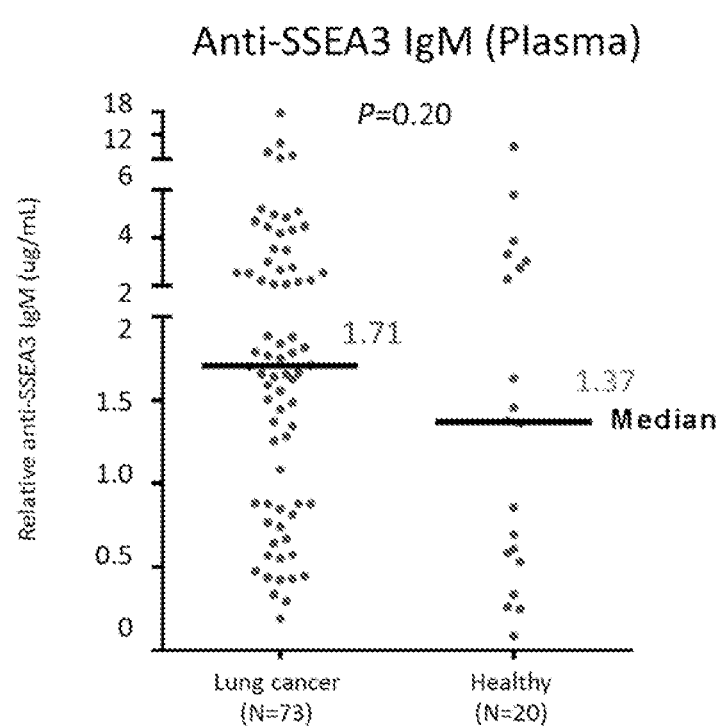
Figure 12C:
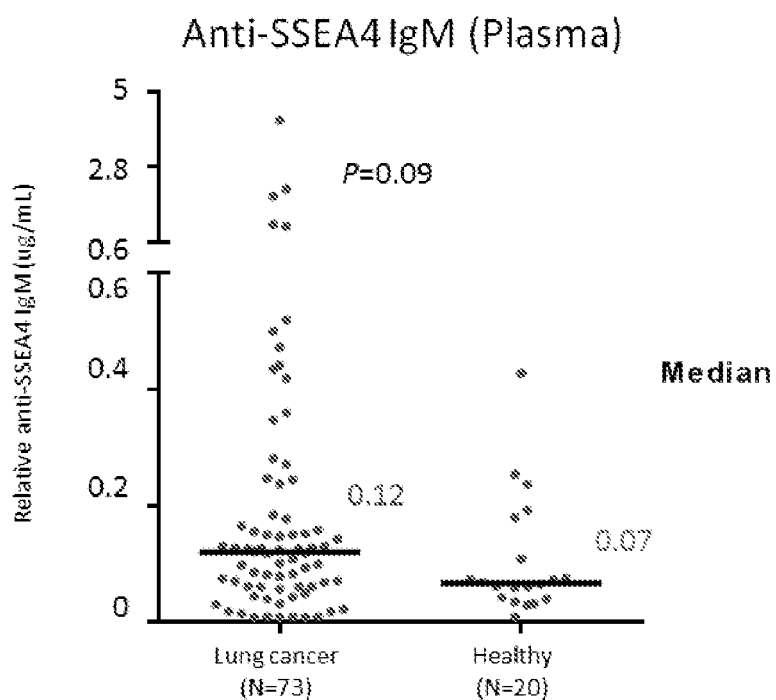
Figure 12D:
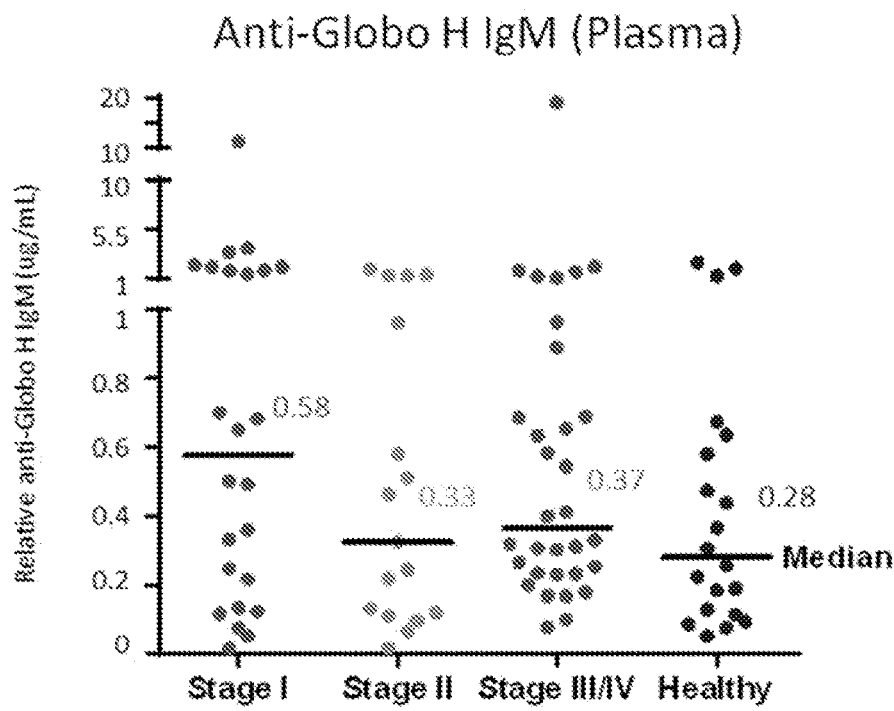
Figure 12E:
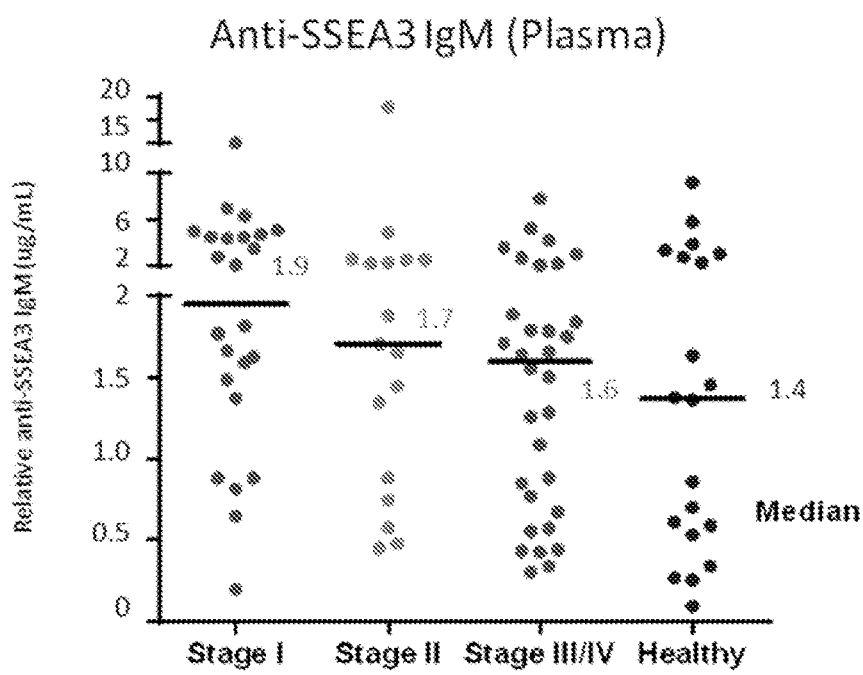
Figure 12F:
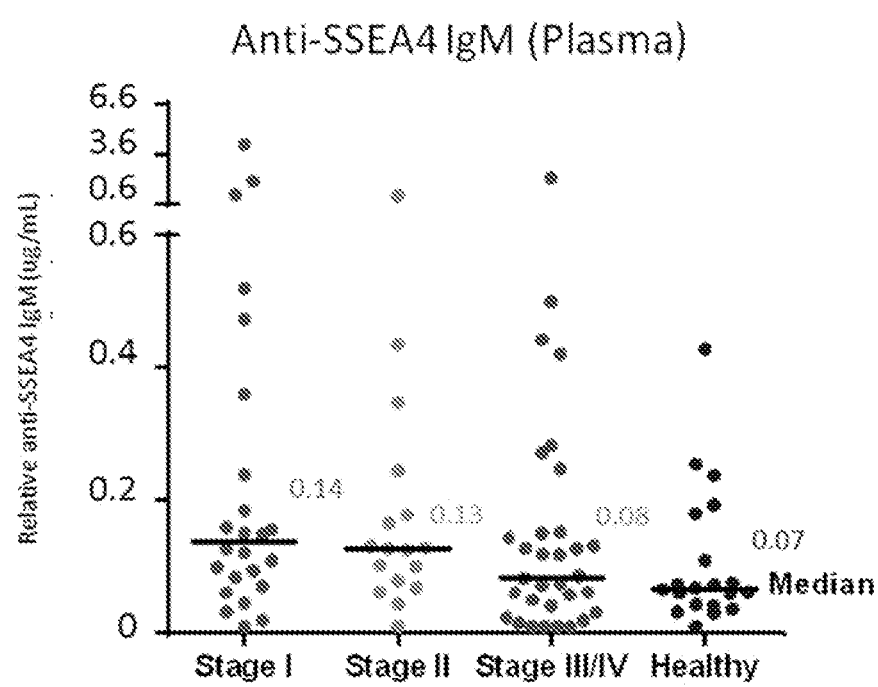

Relative Anti-glycan Human IgM: There were total 93 clinical samples (73 lung cancer and 20 healthy plasma) performed using Globo H-lipid 1, SSEA-3-lipid 1 and SSEA-4-lipid 1 immobilized arrays. The binding patterns of glycan-lipid were listed in FIG. 12. The median values of Globo H-lipid 1 IgM test were 0.41 (lung cancer) and 0.28 (healthy) [FIG. 12A]. The median values of SSEA-3-lipid 1 IgM test were 1.71 (lung cancer) and 1.37 (healthy) [FIG. 12B]. The median values of SSEA-4-lipid 1 IgM test were 0.12 (lung cancer) and 0.07 (healthy) [FIG. 12C]. In addition, no matter Globo H-lipid 1 (FIG. 12D), SSEA-3-lipid 1 (FIG. 12E) or SSEA-4-lipid 1 (FIG. 12F) immobilized arrays could detect Stage I, Stage II and Stage III/IV lung cancers.

Unless defined otherwise, all technical and scientific terms and any acronyms used herein have the same meanings as commonly understood by one of ordinary skill in the art in the field of this invention. Although any compositions, methods, kits, and means for communicating information similar or equivalent to those described herein can be used to practice this invention, the preferred compositions, methods, kits, and means for communicating information are described herein.

All references cited herein are incorporated herein by reference to the full extent allowed by law. The discussion of those references is intended merely to summarize the assertions made by their authors. No admission is made that any reference (or a portion of any reference) is relevant prior art. Applicants reserve the right to challenge the accuracy and pertinence of any cited reference.

What is claimed is:

1. An array of carbohydrates moieties immobilized on a substrate, the array comprising:
   a plurality of G-A-Z carbohydrates, each G-A-Z moiety deposited at a discrete location on the substrate,
   wherein G is one or more tumor associated carbohydrate antigens (TACAs) comprises Globo H, Stage-specific embryonic antigen 3 (SSEA-3) or Stage-specific embryonic antigen 4 (SSEA-4);
   A is a moiety comprising an alkyl, ester or amide; and
   Z is one or a plurality of lipid chains, or one or a plurality of a spacer group with lipid chains;
   wherein one of the G-A-Z carbohydrates is a compound having Formula 2

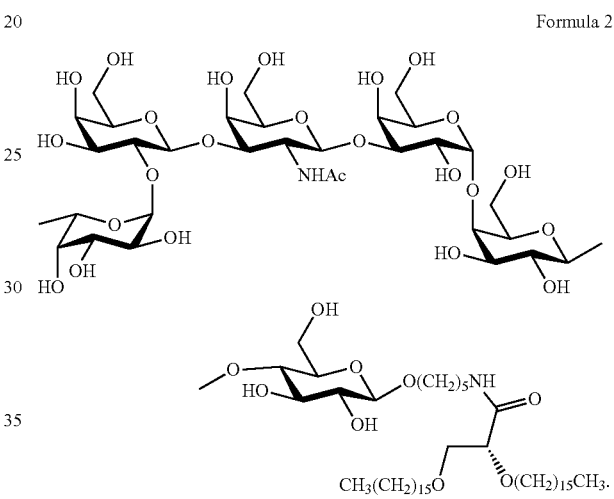

Formula 2

2. The array of claim 1, wherein the substrate is selected from a surface, a solid surface, a non-transparent solid, a solid transparent to selected wavelengths of visible or non-visible light, a particle, a microbubble, or a bead.

3. The array of claim 1, wherein the substrate is nitrocellulose.

4. The array of claim 1, wherein the plurality of GAZ carbohydrates moieties are coated on the substrate.

5. The array of claim 4, wherein the Z moieties in the plurality of GAZ carbohydrates are adhered to the substrate by van der Waals interactions or hydrophobic interactions.

6. An array of carbohydrates immobilized on a substrate for use in detecting complexes, disease diagnosis, treatment monitoring or recurrence monitoring, wherein the array is fabricated by a method comprising:
   (a) providing a substrate;
   (b) coating the substrate with nitrocellulose; and
   (c) immobilizing a plurality of G-A-Z moieties at discrete locations on the surface of the substrate;
   wherein G is one or more tumor associated carbohydrate antigens (TACAs) comprises Globo H, Stage-specific embryonic antigen 3 (SSEA-3) or Stage-specific embryonic antigen 4 (SSEA-4);
   A is a moiety comprising an alkyl, ester or amide; and
   Z is one or a plurality of lipid chains, or one or a plurality of a spacer group with lipid
   chains; wherein one of the G-A-Z moieties is a compound having Formula 2

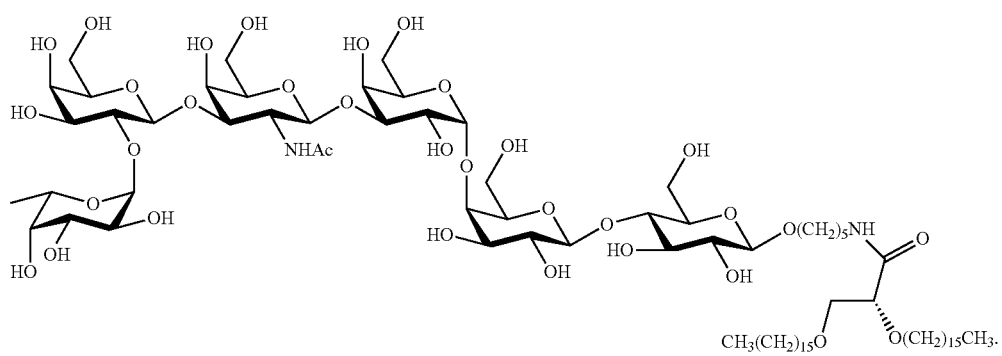

Formula 2

7. A method of characterizing the array of claim 6, comprising contacting the immobilized G-A-Z moieties with a labeled antibody to the TACAs, forming complexes between the antibody and the glycan, and detecting the complexes formed between the antibody and the glycan.

8. The method of claim 7 wherein the labeled antibody comprises a label comprising an enzyme, fluorescent label, a chemiluminescent label, a nanoparticle label.

9. The method of claim 8, wherein the enzyme is alkaline phosphatase (AP) or horseradish peroxidase (HRP).

10. The compound having the formula:
G-A-Z—X Formula 1
wherein:
G is a glycan comprises Globo H, Stage-specific embryonic antigen 3 (SSEA-3) or Stage-specific embryonic antigen 4 (SSEA-4);
A is a moiety comprising an ester or an amide;
X is a substrate, solid surface, coated surface, polymer surface, nitrocellulose-coated surface, or bead surface; a spacer group attached to a surface or a spacer group with a group for adhering a linker to a surface; and
Z is one or a plurality of lipid chains, or one or a plurality of a spacer group with lipid chains; wherein the G-A-Z moiety of G-A-Z—X is a compound having Formula 2

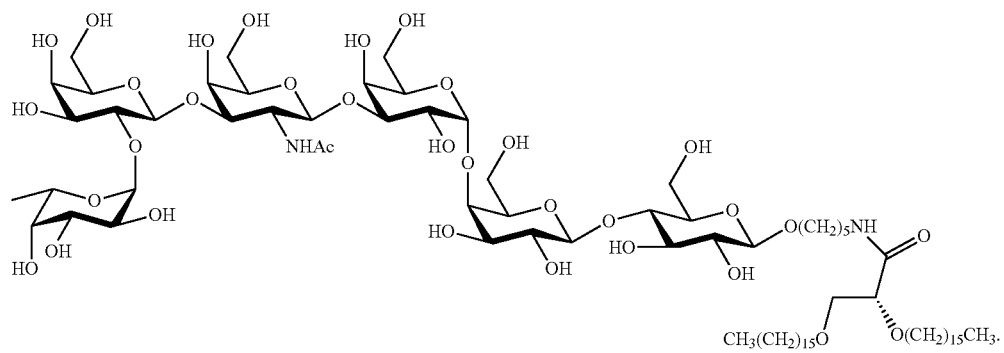

Formula 2

11. The compound having the formula:

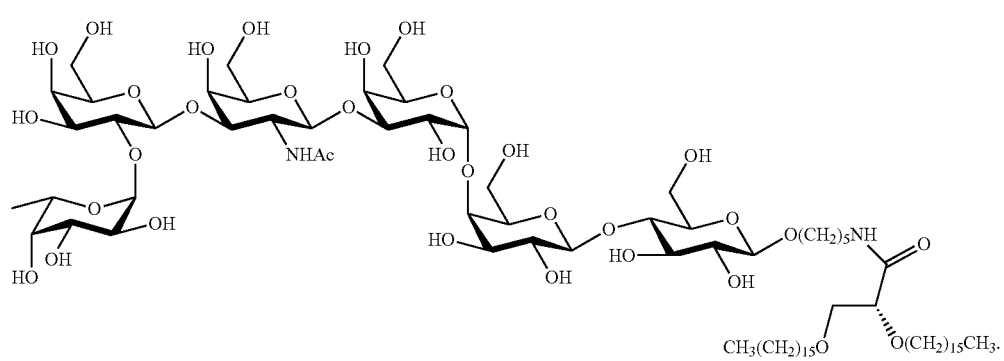

Formula 2

12. A method of improving the sensitivity in an array using a compound having Formula 2

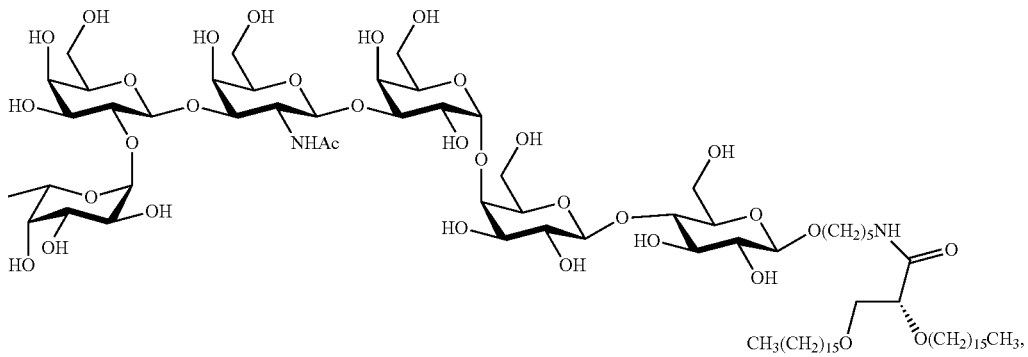

wherein the method comprising:
(a) providing a substrate;
(b) coating the substrate with nitrocellulose; and
(c) immobilizing a plurality of G-A-Z moieties at discrete locations on the surface of the substrate
wherein one the G-A-Z moieties is formula 2.

13. A method for disease diagnosis, treatment monitoring or recurrence monitoring of a subject in need thereof suspected of having cancer, carcinoma, neoplasm or hyperplasia comprising:
(a) providing a sample containing antibodies from a subject suspected of having cancer;
(b) contacting the sample to allow binding of antibodies in the sample to one or more of G-A-Z moieties;
(c) detecting the amount of one or more bound antibodies; and
(d) determining the disease state of the subject based on the amounts of said bound antibodies wherein the disease state is indicated based on the relative antibody binding levels as compared with that of a disease-free subject;
wherein the G-A-Z moieties is a compound having Formula 2

Formula 2

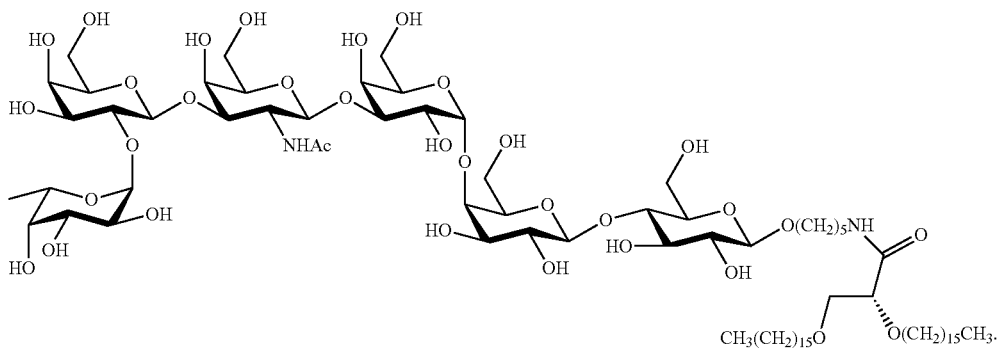

14. A method for detecting a complex, the method comprising:
(a) providing a sample containing antibodies from a subject suspected of having cancer, carcinoma, neoplasm or hyperplasia;
(b) contacting the sample to allow binding of antibodies in the sample to one or more G-A-Z moieties;
(c) detecting the amount of one or more bound antibodies; and
(d) ascertaining the relative antibody binding levels as compared with that of a disease-free subject;
wherein the G-A-Z moieties is a compound having Formula 2

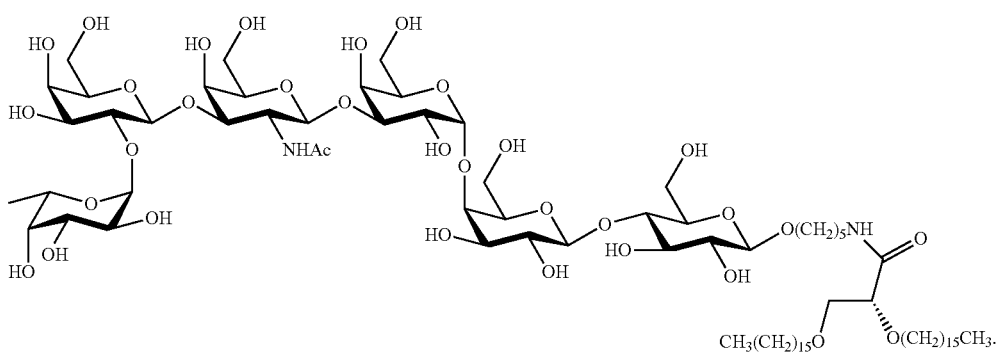

Formula 2

15. The method of claim 13 or 14, wherein the sample consists of serum, blood, plasma, cells, cell medium, saliva, urine, or lymph node fluid.

16. The method of claim 13 or 14, wherein the subject is a human.

17. The method of claim 13 or 14, wherein the cancer is selected from the group consisting of sarcoma, skin cancer, leukemia, lymphoma, brain cancer, glioblastoma, lung cancer, breast cancer, oral cancer, head-and-neck cancer, nasopharyngeal cancer, esophagal cancer, stomach cancer, liver cancer, bile duct cancer, gallbladder cancer, bladder cancer, pancreatic cancer, intestinal cancer, colorectal cancer, kidney cancer, cervix cancer, endometrial cancer, ovarian cancer, testical cancer, buccal cancer, oropharyngeal cancer, laryngeal cancer and prostate cancer.

18. A method for determining the therapeutic efficacy of an antineoplastic agent for cancer treatment of a subject in need thereof, comprising:
    (a) providing a sample from a subject;
    (b) contacting an array comprising one or more tumor associated antigens (TACAs) with the sample;
    (c) detecting the binding of one or more tumor associated antigens (TACAs) or antibodies bound to a compound having Formula 2

21. The method of claim 18, wherein the antineoplastic agent comprises a vaccine composed of a carbohydrate antigen or its immunogenic fragment conjugated with a carrier protein.

22. The method of claim 21, wherein the carbohydrate antigen or its immunogenic fragment comprises Globo H, Stage-specific embryonic antigen 3 (SSEA-3) or Stage-specific embryonic antigen 4 (SSEA-4).

23. The method of claim 21, wherein the carrier protein comprises KLH (Keyhole limpet hemocyanin), DT-CRM 197 (diphtheria toxin cross-reacting material 197), diphtheria toxoid or tetanus toxoid.

24. The method of claim 21, wherein the vaccine is provided as a pharmaceutical composition.

25. The method of claim 24, wherein the pharmaceutical composition comprises Globo H-KLH and an additional adjuvant.

26. The method of claim 25, wherein the additional adjuvant is selected from saponin, Freund's adjuvant or α-galactosyl-ceramide (α-GalCer) adjuvant.

27. The method of claim 24, wherein the pharmaceutical composition comprises OBI-822/OBI-821.

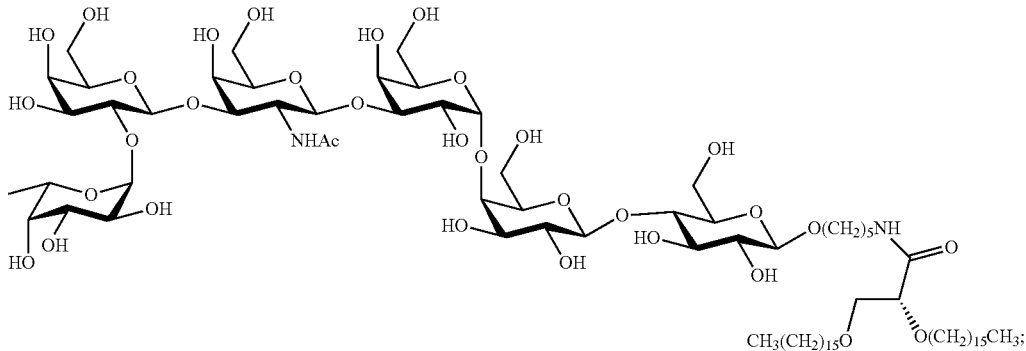

and
    (d) determining the therapeutic effect of an antineoplastic agent in treatment for neoplasm based on the assayed value of glycan detection.

19. The method of claim 18, wherein the sample consists of serum, blood, plasma, cells, cell medium, saliva, urine, lymph node fluid, tumor biopsy or tissue culture.

20. The method of claim 18, wherein the subject is a human.

28. The method of claim 18, wherein the antineoplastic agent comprises an antibody or an antigen-binding portion thereof capable of binding one or more carbohydrate antigens.

29. The method of claim 18, wherein the cancer is selected from the group consisting of sarcoma, skin cancer, leukemia, lymphoma, brain cancer, glioblastoma, lung cancer, breast cancer, oral cancer, head-and-neck cancer, nasopharyngeal cancer, esophagal cancer, stomach cancer, liver cancer, bile duct cancer, gallbladder cancer, bladder cancer, pancreatic cancer, intestinal cancer, colorectal cancer, kidney cancer, cervix cancer, endometrial cancer, ovarian cancer, testical cancer, buccal cancer, oropharyngeal cancer, laryngeal cancer and prostate cancer.

* * * * *